(12) United States Patent
Saunders et al.

(10) Patent No.: US 10,695,465 B2
(45) Date of Patent: Jun. 30, 2020

(54) MICROGEL COMPOSITIONS

(71) Applicant: Gelmetix Limited, Cheshire (GB)

(72) Inventors: Brian Saunders, Manchester (GB);
Amir Hossein Milani, Manchester (GB); Ruixue Liu, Manchester (GB);
Anthony Freemont, Manchester (GB)

(73) Assignee: Gelmetix Limited, Cheshire (GB)

( * ) Notice: Subject to any disclaimer, the term of this patent is extended or adjusted under 35 U.S.C. 154(b) by 0 days.

(21) Appl. No.: 16/253,707

(22) Filed: Jan. 22, 2019

(65) Prior Publication Data

US 2019/0151512 A1 May 23, 2019

Related U.S. Application Data

(62) Division of application No. 13/579,809, filed as application No. PCT/GB2011/050329 on Feb. 18, 2011.

(30) Foreign Application Priority Data

Feb. 19, 2010 (GB) .................................. 1002862.9

(51) Int. Cl.
| | | |
|---|---|---|
| *A61K 31/74* | (2006.01) | |
| *A61L 27/52* | (2006.01) | |
| *A61L 27/00* | (2006.01) | |
| *C08F 299/02* | (2006.01) | |
| *C08L 33/06* | (2006.01) | |
| *C08L 51/00* | (2006.01) | |

(52) U.S. Cl.
CPC ................ *A61L 27/52* (2013.01); *A61L 27/00* (2013.01); *C08F 299/024* (2013.01); *C08L 33/064* (2013.01); *C08L 51/003* (2013.01); *A61L 2300/62* (2013.01); *A61L 2430/38* (2013.01); *C08L 2205/04* (2013.01)

(58) Field of Classification Search
None
See application file for complete search history.

(56) References Cited

U.S. PATENT DOCUMENTS

| | | |
|---|---|---|
| 5,508,325 A | 4/1996 | Craun et al. |
| 6,428,576 B1 | 8/2002 | Haldimann |
| 6,608,134 B1 | 8/2003 | Tobing et al. |
| 2008/0254133 A1 | 10/2008 | Saunders et al. |

FOREIGN PATENT DOCUMENTS

| | | |
|---|---|---|
| WO | WO200068316 A1 | 11/2000 |
| WO | WO2007060424 A2 | 5/2007 |
| WO | WO2011009867 A2 | 1/2011 |
| WO | WO2011101684 A1 | 8/2011 |

OTHER PUBLICATIONS

Cho et al., Nano Letters, 2008; 8(1): 168-172, Supporting Information, pp. 1-4.
Saunders et al., Doubly crosslinked pH-responsive microgels prepared by particle inter-penetration: swelling and mechanical properties, Soft Matter, 2011, 7: 4696-4704.

*Primary Examiner* — David Browe
(74) *Attorney, Agent, or Firm* — Burns & Levinson LLP; Shawn P. Foley

(57) ABSTRACT

This invention relates to a method of treating a subject suffering from a condition characterized by damaged or degenerated soft tissue (such as, for example, intervertebral discs) by injecting swellable microgel particles to a location within the subject containing the damaged or degenerated soft tissue, after which said microgel particles covalently bind together in vivo to form a doubly cross-linked gel.

20 Claims, 69 Drawing Sheets

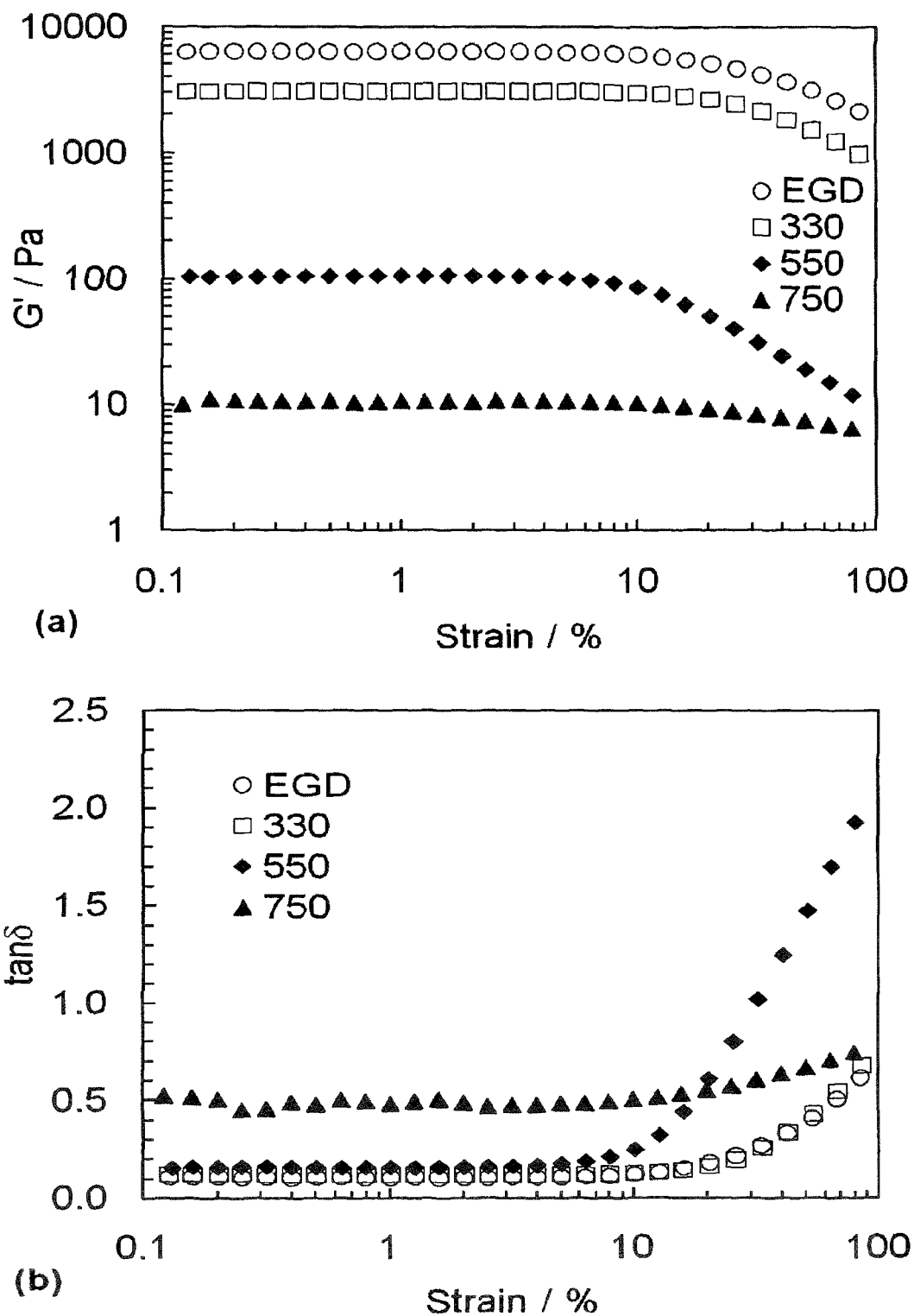
Figure 6C (a) and (b)

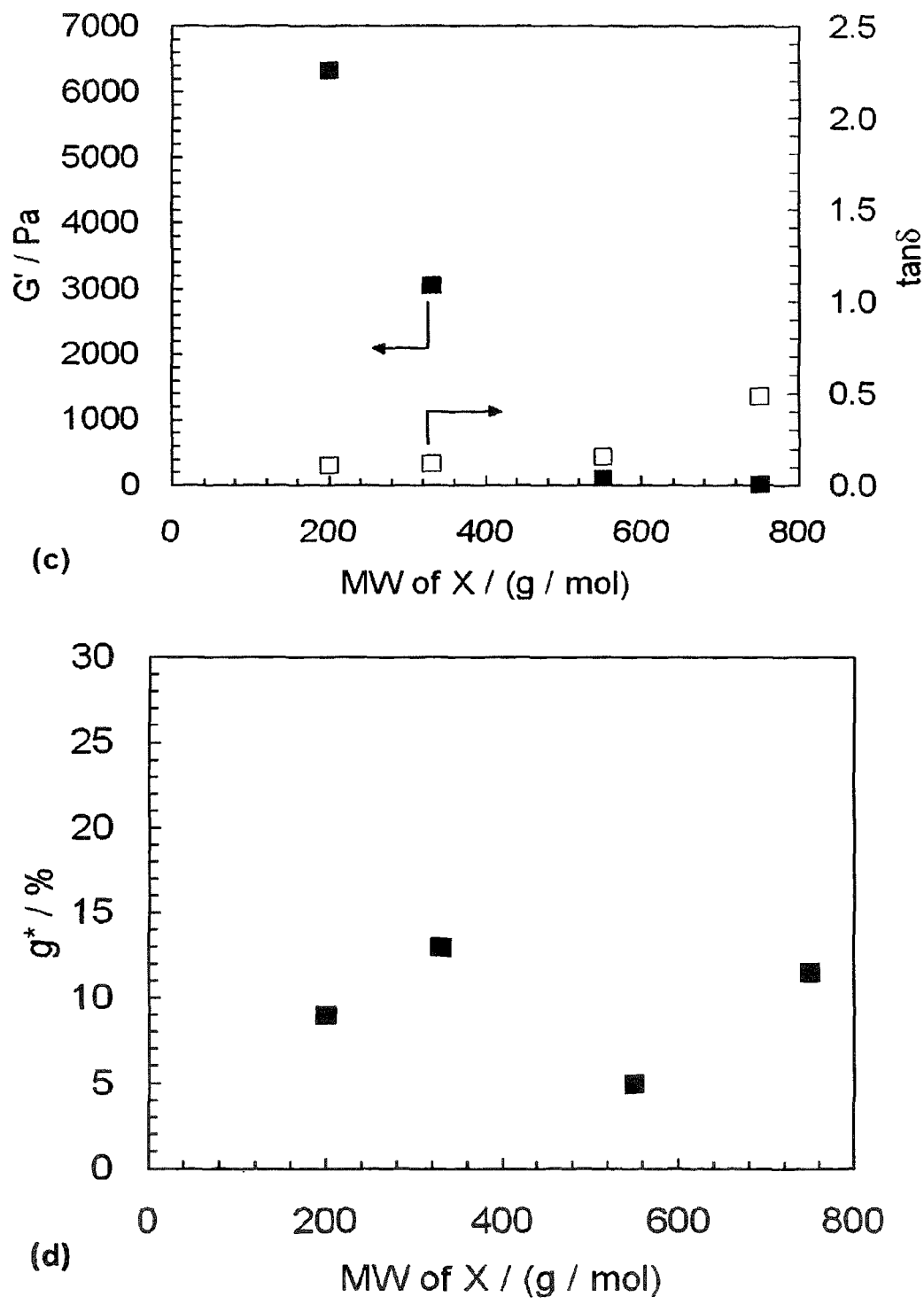
Figure 6C (c) and (d)

(a)

(b)

(a)

(b)

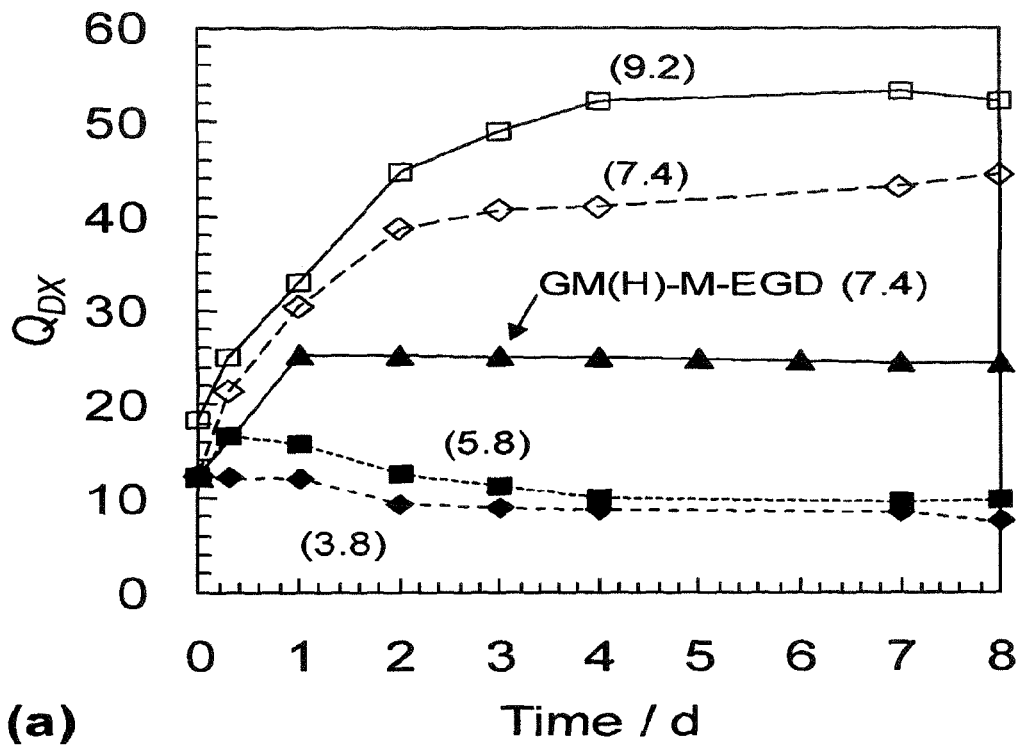
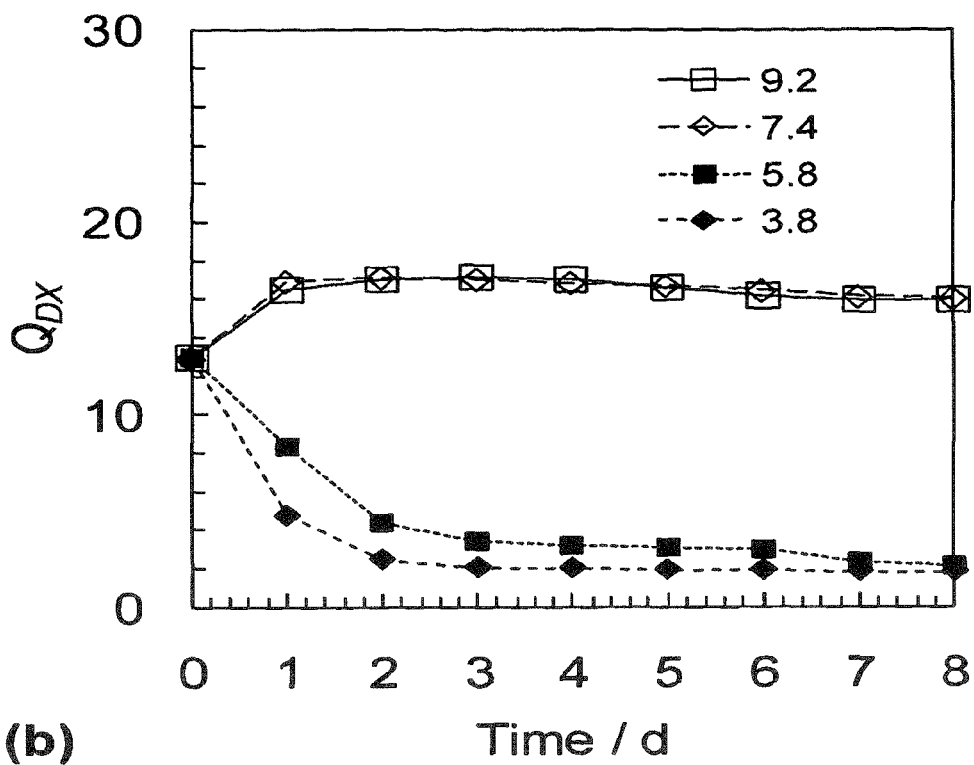
Figure 12A.1

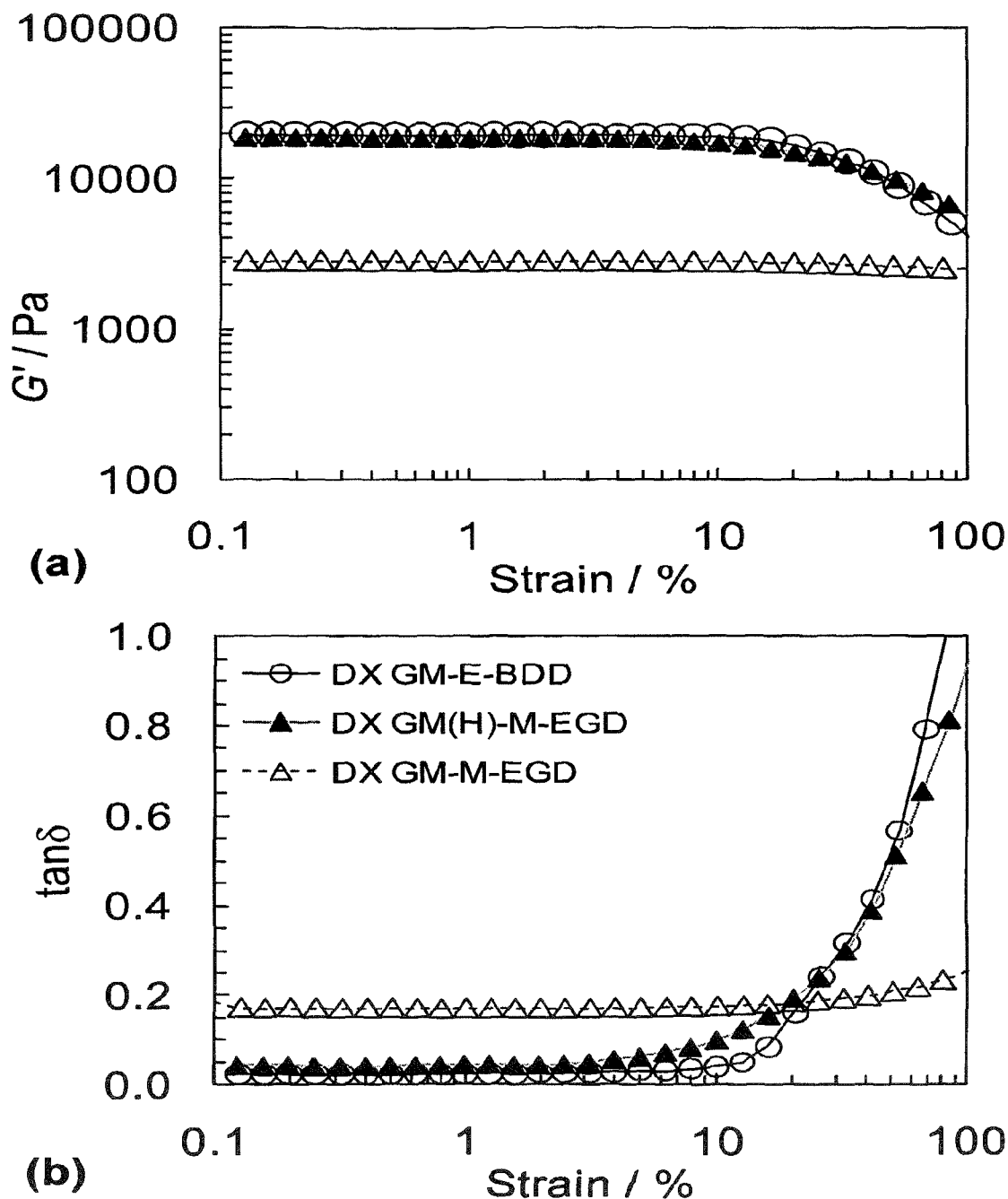
Figure 14A-1.1

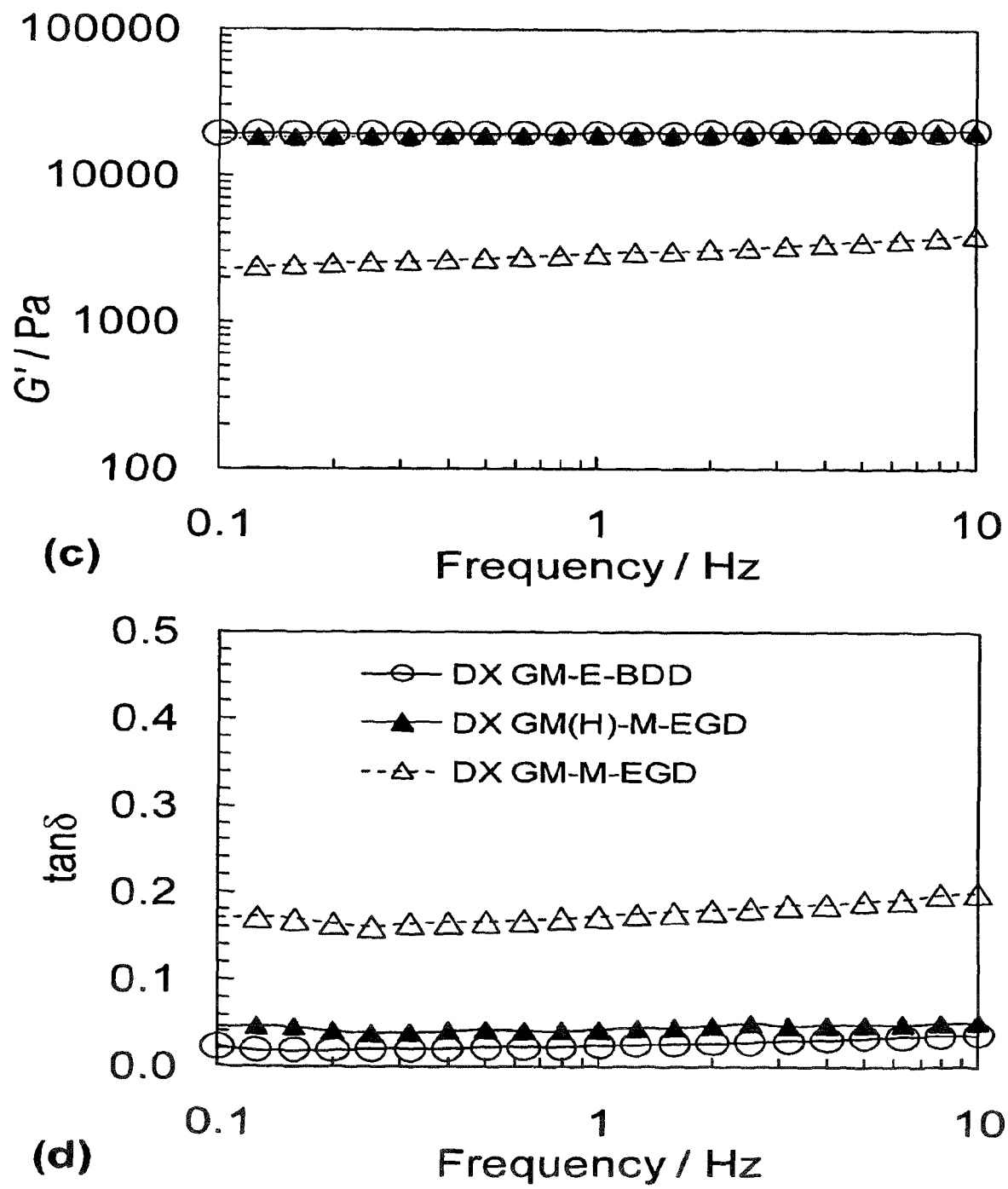
Figure 14A-1.1

(a)

(b)

MICROGEL COMPOSITIONS

CROSS-REFERENCE TO RELATED APPLICATIONS

This application is a divisional application of co-pending U.S. application Ser. No. 13/579,809 filed on Aug. 17, 2012, which claims priority to and the benefit of a '371 of international Application No. PCT/GB2011/050329 filed on Feb. 18, 2011, which claims priority of 1002862.9 filed on Feb. 19, 2010 in Great Britain. The entire contents of each of the above applications are incorporated herein in their entirety by reference for all purposes.

This invention relates to microgel compositions, and in particular, to gel compositions formed by binding a plurality of individual microgel particles together. The present invention also relates to processes for the preparation of these compositions and to their use for particular applications, especially medical applications such as the repair of damaged, degenerated or inappropriately formed load-bearing tissue (such as, for example, intervertebral discs).

BACKGROUND

Microgel particles, which are nanoscopic or microscopic colloidal particles of cross-linked polymer, have been investigated for a number of different potential applications. Particular examples include their use as micro-reactors for the template synthesis of inorganic nanoparticles, as optically active materials including lenses and photonic crystals, and as drug delivery systems (Das et al. Annual Reviews of Materials Research, 2006, Vol. 36: 117-142).

Microgel particles have also been used for the preparation of photonic hydrogels, especially photonic hydrogels capable of manipulating photons in the visible and near-infrared spectrum (see Cai et al. Macromolecules, 2008, Vol. 41: 9508-9512). More specifically, Cai et al. describe photonic hydrogels derived from thermally-responsive, vinyl functionalized microgel particles. The microgel particles, which are formed from PEG-polymers, are cross-linked by interlinking polymer chains formed by the polymerization of ethyleneglycolacrylate (PEGA) and/or acrylamide monomers. Upon photo-initiation, the ethyleneglycolacrylate (PEGA) or acrylamide monomers react with the vinyl groups present on the microgel particles and polymerise to form interlinking poly(PEGA) or poly(acrylamide) polymer chains. The result is a hydrogel composed of microgel particles connected together by interlinking polymer chains of varying length.

One particular application of biocompatible microgel particles is their potential utility for the replacement or repair of injured, degenerated or inappropriately formed load-bearing soft tissues, such as, for example, intervertebral discs and the tissues found in articular joints (such as the elbow, knee, hip, wrist, shoulder and ankle). These soft tissues need to be able to bear significant loads and changes in pressure. For example, the pressures experienced within human intervertebral discs can vary from about 0.5 MPa when sitting to about 2.3 MPa when lifting a 20 kg weight. Consequently, the ability of soft tissues, such as intervertebral discs, to bear varying biomechanical loads is essential for the normal operation of the body.

The principle load-bearing tissue of the intervertebral disc is the disc-shaped nucleus pulposus, which forms the centre of an intervertebral disc. The nucleus pulposus consists of chondrocytes (cartilage producing cells) within a matrix of collagen and proteoglycans. Articular cartilage, which is the tissue covering bony ends of articular joints, has a similar composition to that found in the nucleus pulposus. The proteoglycans have a high negative charge density and are responsible for the high swelling pressure of the nucleus pulposus. The nucleus pulposus is a natural ionic hydrogel and contains about 75% water in adults. The proteoglycan content gradually decreases with age due to natural degeneration, and this can result in the formation of three dimensional channels known as "clefts". The formation of clefts provides weak points or voids in the structure of the disc, which can eventually become detrimental to the overall shape, form, dimensions and performance of the disc, particularly when a pressure is applied.

Any injury, degeneration or malformation in load bearing tissues can result in significant pain and lack of mobility. A major proportion of all intervertebral discs in the lower part of the spine show signs of degeneration by the age of 50. This can result in chronic back pain, which is a major cause of morbidity and absence from work.

The treatment of damaged load-bearing soft tissues, such as intervertebral discs or articular joints, is usually directed at symptomatic relief of the pain. In severe cases, surgical intervention may be necessary to remove some of the damaged tissue and insert a prosthetic replacement. Surgical intervention is effective in relieving pain, but it can result in the damage of adjacent tissues and alterations in the biomechanical/load-bearing properties of the tissue concerned. In addition, surgical intervention may require a protracted stay in hospital and significant morbidity for the patient concerned.

A material science approach to address the problem of degenerating intervertebral discs and other load bearing tissues involves injecting molecules that polymerise at the site of injection. The polymer deposit formed provides additional mechanical strength to the bolster the remaining tissue. One particular example described in WO2000/062832 is the in situ polymerisation of poly(ethylene glycol) tetra-acrylate in the nucleus pulposus of the intervertebral disc. Another example involves the injection of chitosan into the nucleus pulposus and allowing it to polymerise. Chitosan is a positively charged polysaccharide that is soluble in water at low pH. It undergoes a solution-to-gel transition when the pH is increased. It has therefore been contemplated that chitosan may be injected as a low pH solution and then allowed to form a gel when it is exposed to a higher pH in vivo. The gel that forms in vivo is uncharged and forms a polymer network that occupies the whole volume of the injected solution. Hence, it becomes a macrogel through in situ polymerisation.

The provision of injectable materials that can be used to treat damaged or degenerated load-bearing tissues, such as intervertebral discs, is a major challenge. It should also be appreciated that a key criterion for such materials is that their mechanical properties replicate that of the normal healthy load-bearing tissue as closely as possible.

WO2007/060424, the entire contents of which are incorporated herein by reference, describes the use of pH-responsive microgel particles for this particular application. The use of biocompatible pH-responsive microgel particles provides many attractions. In particular, the microgel particles can be injected in a compacted (or "non-swollen") configuration by controlling the pH of the injection medium. However, once present in the body, the pH will typically adjust to the normal physiological pH of the tissue due to the natural buffers present in physiological fluids. At physiological pH values, the polymer that forms the pH-responsive microgel particles undergoes a conformational change, which causes the microgel particles to hydrate and swell. The swollen microparticles then provide a gelatinous mass which fills any regions of degenerated tissue and provides additional mechanical support to the tissue concerned.

However, despite the attractions of this approach, the mechanical properties of the gel is not optimal and there is a tendency for the microgel particles to dissipate/migrate away from the injection site, so there still remains a need for alternative injectables that are capable of providing further improved biomechanical support for the treatment or replacement of damaged or degenerated load-bearing tissues.

It is therefore an object of the present invention to obviate or mitigate one or more of the problems of the prior art, whether identified herein or elsewhere. In particular, it is an object of the present invention to provide a further improved method for repairing damaged and degenerated load-bearing tissue.

BRIEF SUMMARY OF THE DISCLOSURE

The present invention provides novel microgel compositions having improved mechanical properties that enable them to be used for the repair and/or replacement of damage soft tissue, such as intervertebral discs, as well as for other applications.

In its broadest terms, the present invention provides a composition comprising a plurality of microgel particles, wherein adjacent microgel particles are bound together by either
  (i) covalent cross-links formed by the reaction of vinyl-containing moieties grafted onto the surfaces of the microgel particles; and/or
  (ii) by a cross-linked polymer network that interpenetrates adjacent microgel particles and thereby binds the particles together, wherein the vinyl polymer network is formed by the polymerisation of a water soluble cross-linking monomer comprising two or more vinyl groups.

The compositions of the present invention possess advantageous mechanical properties, particularly in terms of their ability to support loads. The mechanical properties of these compositions can be readily and advantageously fine tuned and controlled in order to optimise the mechanical properties of the resultant hydrogel composition for load-bearing applications. The mechanical properties can be altered by, for example, modifying the preparation conditions of the composition, varying the parent microgel particles, modifying the cross-linking reaction conditions, altering the pH of the composition or the concentration of the microgel particles.

In particular, the mechanical properties of the compositions of the invention can substantially replicate those of normal healthy load-bearing tissue, such as, for example, intervertebral discs, and thus allow for the provision of hydrogel compositions materials that can be used to treat damaged or degenerated load-bearing tissues. Moreover, the compositions of the invention can advantageously be formed in situ at the desired target site. This enables the precursor materials (including, inter alia, the microgel particles, cross-linking monomers and/or other required reactants) to be administered in a convenient form (e.g. by liquid injection) to a target site (e.g. in vivo) before the hydrogel compositions and/or doubly cross-linked (DX) microgels are duly formed and molded in situ within the desired target site.

Compositions of the present invention also provide for a more consistent physical form, which is particularly advantageous for in vivo applications where predictability of the final form is crucial. Such compositions are also stable and robust, having high critical strains, and have a low propensity to migrate or redisperse when serving a load-supporting function, especially in vivo. In particular, such compositions have a reduced propensity to redisperse in aqueous alkaline or acidic environments.

The compositions of the present invention have the further advantage that they can be formed from their conveniently administrable precursors using either temperature of pH-triggered swelling of the microgel particles. This enables the precursor components required to form the compositions of the invention to be effectively stored for long periods before administration and composition formation. This is particularly advantageous for medical applications where the administrable form of the composition must satisfy regulations and requirements for manufacture, transport, and storage of the administrable form. Moreover, for in vivo applications, the properties of the compositions can be modified to allow a physiological pH to provide the pH-triggered swelling of the microgel particles. For example, physiological pH-triggered swelling of the microgel particles can cause adjacent microgel particles to enlarge and inter-penetrate with their neighbouring precursor microgel particles and facilitates the cross-linking of adjacent microgel particles to form the compositions of the invention. This is advantageous because particles maintain a 3-dimensional connected (non-porous) structure with maximised load distribution within the gel.

Advantages of the DX microgels over singly cross-linked (SX) microgels include higher elastic modulus values, higher yield strains, and swelling in aqueous solutions without any re-dispersion.

Although DX microgels resemble a hydrogel in that they are macroscopic, they are also very different because DX microgels are composed of inter-linked nanometer (or sometimes micrometer)-sized microgel particles. This means that there mechanical and swelling properties can be altered at the size scale of the microgel particles. This offers new possibilities to tune the mechanical properties, construct hybrids and blends, that do not exist for conventional macromolecular hydrogels. The term macromolecular hydrogel refers to hydrogels formed by covalently linking molecules—conventional hydrogels.

A particular advantage of the DX microgel preparation methods of the present invention is that the microgel particles inter-penetrate prior to double crosslinking. That means that there is an efficient, three-dimensional, network in place for distributing stress once the material is formed. As such, modulus values are higher than those of the precursor SX physical gels.

Thus, in a particular aspect, the present invention provides a composition comprising a plurality of microgel particles, wherein adjacent microgel particles are covalently bound together by covalent cross-links formed by the reaction of vinyl-containing moieties grafted onto the surfaces of the microgel particles. In this aspect of the invention, vinyl functionalized microgel particles are directly cross-linked to each other without any intervening cross-linker(s). This can be advantageous because the cross-linking chemistry is simple and requires fewer reagents. The resultant hydrogel compositions also possess a more consistent physical form, which is generally more robust with a lower propensity for migration and/or re-dispersement when supporting loads (e.g. in vivo). Moreover, administration of compositions of the present invention is particularly convenient (especially when forming the composition in vivo). These compositions also possess advantageous mechanical properties, particularly advantageous elastic properties. These compositions also display excellent gel rheology with low viscosity, making them ideal for soft tissue repair. Moreover, the mechanical properties of the compositions can be readily fine tuned and controlled by merely altering the degree of vinyl functionalisation of the microgel particles, and also the concentration of the microgel particles used during composition preparation. As such, compositions can be tailored for a variety of specific applications.

In a further aspect the present invention provides a process for the preparation of a composition comprising a plurality of microgel particles, wherein adjacent microgel particles are bound together by covalent cross-links formed by the reaction of vinyl-containing moieties grafted onto the surfaces of the microgel particles, the process comprising:
  (i) providing, in an aqueous medium, a plurality of microgel particles comprising functional vinyl-containing moieties grafted onto the surfaces of the microgel particles; and
  (ii) causing the microgel particles to swell so that adjacent microgel particles are brought into contact with one another and facilitating the free radical coupling of the vinyl groups to covalently bind adjacent microgel particles together.

In a further aspect the present invention provides a microgel particle comprising a plurality of vinyl-containing moieties grafted onto the surface of the microgel particle.

In a further aspect the present invention provides a process of preparing a microgel particle comprising a plurality of vinyl-containing moieties grafted onto the surface of the microgel particle, the process comprising reacting a microgel particle with a compound of the formula:

Z-L-B wherein Z, L and B are as defined herein.

In a further particular aspect, the present invention provides a composition comprising a plurality of microgel particles that are bound together by a cross-linked polymer network that interpenetrates adjacent microgel particles, wherein the vinyl polymer network is formed by the polymerisation of a water soluble cross-linking monomer comprising two or more vinyl groups. The compositions of this particular aspect of the invention have the advantage that compositions with highly desirable mechanical properties, particularly those suitable for soft tissue repair, can be formed without the need to pre-functionalise the microgel particles with vinyl-containing moieties. This can simplify the composition formation process for certain applications, and potentially simplifies the manufacture of the administrable form of the compositions, especially where in vivo applications are intended. Moreover, such compositions still allow for temperature and/or pH-triggered swelling, the advantages of which are outlined above, particularly with respect to in vivo applications. The properties of such compositions can also be readily controlled and fine tuned by varying the molecular weight of the cross-linking monomer.

In an embodiment, the composition is substantially free of any direct cross-linking between the microgel particles (i.e. there are no direct covalent cross-links formed between the polymer chains making up adjacent microgel particles).

Alternatively, the compositions of this aspect of the invention may further comprise covalent cross-links formed by the reaction of vinyl-containing moieties grafted onto the surfaces of adjacent microgel particles. These covalent cross-links may suitably be in addition to the cross-linked polymer network that interpenetrates adjacent microgel particles. As such, the composition may comprise microgels that are bound by both direct cross-linking and a separately interpenetrating polymer network.

Alternatively or additionally, the composition may comprise a degree of indirect cross-linking between microgel particles, for instance, where the microgel particles pre-functionalised with cross-linkable vinyl moieties are cross-linked via the cross-linking monomer (i.e. one of the vinyl groups of the cross-linking monomer reacts with a vinyl group on one microgel particle whilst another of the vinyl groups of the cross-linking monomer reacts with a vinyl group on another microgel particle). The use of a cross-linking monomer comprising two or more vinyl groups, e.g. a bi-vinyl cross-linking monomer, is advantageous over the use of cross-linking monomers comprising only a single vinyl group because the chain length of any indirect cross-links are generally better regulated, thus the composition's properties are more easily controlled and fine tuned through selection of the appropriate cross-linking monomer. Where, as in the case Cai et al. (Macromolecules, 2008, Vol. 41: 9508-9512), a cross-linking monomer comprises only a single vinyl group, cross-links between microgels are formed with varying chain lengths (following the propagated polymerization of the cross-linking monomers themselves), which effects control of the properties of the resulting composition.

In a further aspect, the present invention provides a process for the preparation of a composition comprising a plurality of microgel particles that are bound together by a cross-linked polymer network that interpenetrates adjacent microgel particles and thereby binds the particles together, wherein the vinyl polymer network is formed by the polymerisation of a water soluble cross-linking monomer comprising two or more vinyl groups, the process comprising:
  (i) providing, in an aqueous medium, a plurality of microgel particles; and
  (ii) causing the microgel particles to swell in the presence of a water soluble cross-linking monomer comprising two or more vinyl groups such that adjacent microgel particles are brought into contact with one another and facilitating the polymerisation of the cross-linking monomer to form a cross-linked polymer network that interpenetrates the particles and binds adjacent microgel particles together.

In a further particular aspect, the present invention provides a composition comprising a plurality of microgel particles, wherein adjacent microgel particles are bound together by a combination of:
  (i) covalent cross-links formed by the reaction of vinyl-containing moieties grafted onto the surfaces of the microgel particles; and
  (ii) by a cross-linked polymer network that interpenetrates adjacent microgel particles and thereby binds the particles together, wherein the vinyl polymer network is formed by the polymerisation of a water soluble cross-linking monomer comprising two or more vinyl groups.

In a further aspect the present invention provides a composition obtainable by any one of the processes defined herein.

In a further aspect, the present invention provides a precursor composition for forming a composition of the invention as defined herein, the precursor composition comprising a plurality of microgel particles together with one or more additional cross-linking reactants or reagents (e.g. cross-linking monomers, vinyl polymerisation initiators etc.). Suitably, the microgel particles are in a non-swollen configuration in the precursor composition, thereby enabling them to be conveniently stored and administered to the target site for in situ formation of the composition of the invention.

In a further aspect, the present invention provides a method of treating a subject suffering from a condition characterised by damaged or degenerated soft tissue, the method comprising administering to a subject in need of such treatment, a therapeutically effective amount of a composition as defined herein.

In a further aspect, the present invention provides a composition as defined herein for use in the treatment of a condition characterised by damaged or degenerated soft tissue.

In a further aspect, the present invention provides a method of treating a subject suffering from a condition characterised by damaged or degenerated soft tissue, the method comprising forming a composition as defined herein in situ within the body.

In a further aspect, the present invention provides a composition as defined herein for use in the treatment of a condition characterised by damaged or degenerated soft tissue, wherein said composition is formed in situ within the body.

In a further aspect, the present invention provides a method of treating a subject suffering from a condition characterised by damaged or degenerated soft tissue, the method comprising administering a precursor composition as defined herein which reacts to form a composition as defined herein in situ within the body.

In a further aspect, the present invention provides a precursor composition as defined herein for use in the treatment of a condition characterised by damaged or degenerated soft tissue, wherein said composition forms a composition of the invention as defined herein in situ within the body.

The above and further aspects of the invention are described in further detail herein.

BRIEF DESCRIPTION OF THE DRAWINGS

Particular embodiments of the invention are further described hereinafter with reference to the accompanying drawings, in which.

DETAILED DESCRIPTION

Microgel Compositions

Figure 1:
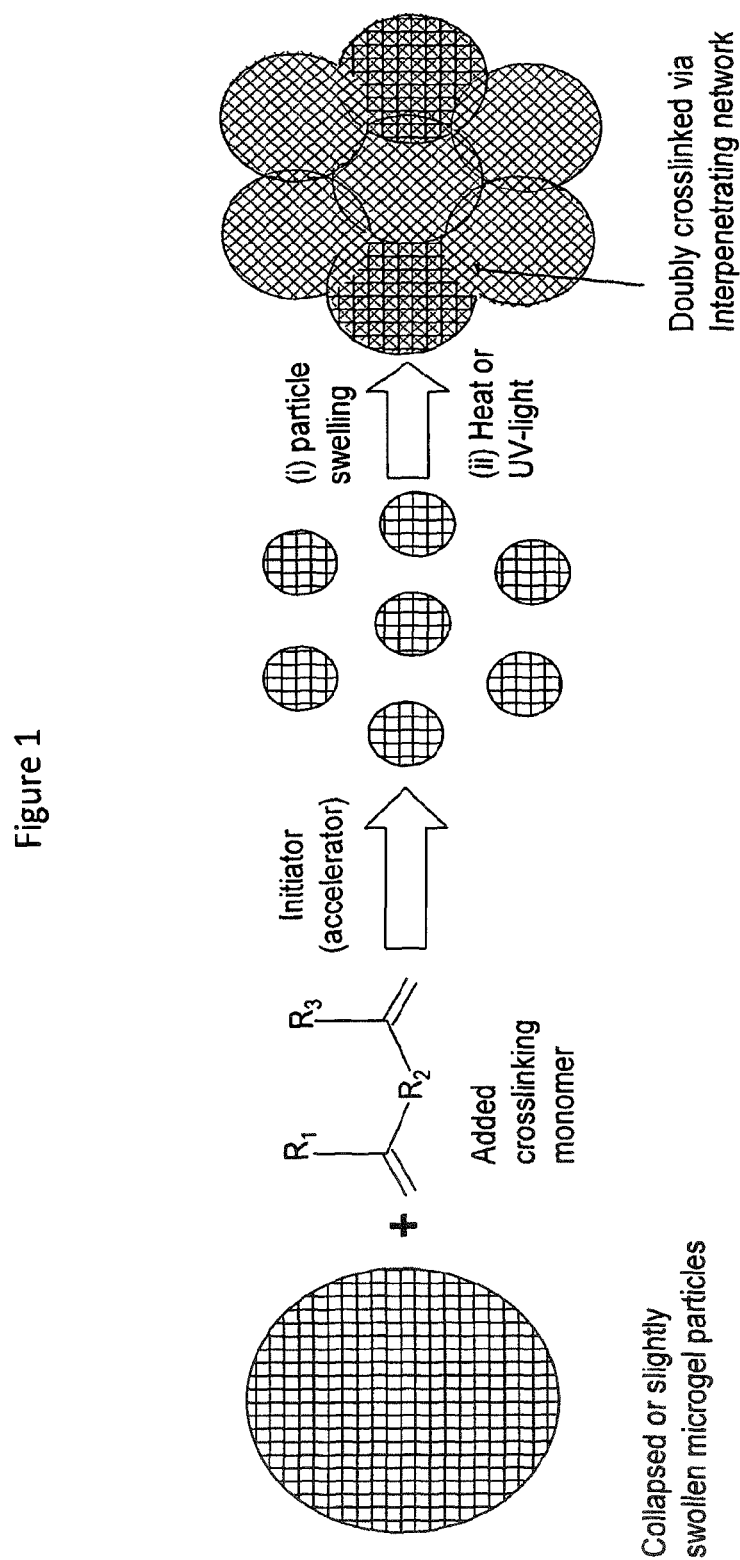
FIG. 1 is a scheme showing a first method for preparing a cross-linked microgel particle composition of the present invention.

The present invention provides microgel compositions that possess particularly advantageous mechanical properties that render them suitable for a number of applications, including the repair of damaged or degenerated soft tissue.

The compositions of the invention comprise microgel particles that are either bound together by covalent cross-links formed by the reaction of vinyl containing moieties grafted onto the surface of the microgel particles; and/or by a cross-linked polymer network that interpenetrates adjacent microgel particles and thereby binds the particles together, wherein the polymer network is formed by the polymerisation of a water soluble cross-linking monomer comprising two or more vinyl groups.

In a further aspect, the present invention provides a precursor composition for forming a composition of the invention as defined herein, the precursor composition comprising a plurality of microgel particles together with one or more additional cross-linking reactants or reagents (e.g. cross-linking monomers, vinyl polymerisation initiators etc.). Suitably, the microgel particles are in a non-swollen configuration in the precursor composition, thereby enabling them to be conveniently stored and administered to the target site for in situ formation of the composition of the invention.

The present invention further provides a composition obtainable by any one of the processes defined herein.

In addition, the present invention further provides a composition obtained by any one of the processes defined herein.

The present invention also provides a composition directly obtained by any one of the processes defined herein.

As discussed in further detail below, the approaches to bind the microgel particles together rely on free-radical chemistry to induce the coupling of vinyl groups (whether it is the free radical polymerisation of the cross-linking monomers comprising two or more vinyl groups or the vinyl containing moieties grafted onto the surface of the microgel particles, or a combination thereof).

Microgel Particles

The compositions of the present invention are macrogel hydrogel compositions that are formed by binding together a plurality of microgel particles.

By the term "microgel particle", we mean a hydrogel particle having a size within the range of 1 nm to 100 μm and which comprises a cross-linked polymer formed by the polymerisation of a plurality of cross-linked co-monomers.

The microgel particle itself may be considered as being one macromolecule (i.e. the cross-linked polymer) comprising a molar mass of between about $10^6$ and $10^{10}$ Da. (e.g. between $10^6$ and $10^9$ Da). However, the individual co-monomers that were used during the preparation of the microgel particles may comprise a molar mass of between about 5 Da and 5,000 Da, more preferably, between about 10 Da and 1,000 Da, even more preferably, between about 50 Da and 500 Da, and most preferably, between about 75 Da and 400 Da. In a most preferred embodiment, the co-monomers used in the polymerisation reaction comprise a molar mass of between about 100 Da and 300 Da.

The microgel particle is suitably a cross-linked co-polymer particle that is pH and/or temperature responsive. By "pH and/or temperature responsive" we mean that the polymer that forms the microgel particles can undergo a pH and/or temperature dependent conformational change, which has a consequential effect on the hydration of the particle. This means that by varying the pH and/or temperature, the microgel particles can transition between a collapsed configuration, in which the particle is in a compact configuration, to a swollen configuration in which the particle is in the form of a highly hydrated gel (or microgel).

By the term "collapsed configuration", we mean the particle is substantially reduced in size and has a smaller average diameter than in the swollen configuration. In this state, the polymer present in the microgel particles adopts a configuration which does not favour the ingress of water into the particle. The limit of the collapsed configuration is when the particle contains virtually no water. Hence, the microgel particle preferably comprises less than about 70% (w/w) water, more preferably, less than about 50% (w/w) water, preferably, less than about 30% (w/w) water, and even more preferably, less than about 20% (w/w) water, and most preferably, less than about 10% (w/w) water in the collapsed configuration. In a particular embodiment, the particles comprise a minor proportion of water (less than about 40% w/w) in the collapsed configuration. It will be appreciated that this water content is a reference to the water present within the particle.

It will be appreciated that the diameter of the microgel particles will depend upon the hydration (water content) thereof which is in turn dependent upon the configuration of the polymer. The diameter of the microgel particle in the collapsed configuration is typically less than about 100 µm, more typically, less than about 50 µm, and even more typically, less than about 20 µm. However, in a preferred embodiment, it is preferred that the diameter of the microgel particle in the collapsed configuration is less than about 10 µm, more preferably, less than about 5 µm, and even more preferably less than about 1 µm. Most preferred particles are on the nanometer scale, i.e. the average diameter of the microgel particle in the collapsed configuration is preferably between about 1 nm and 1000 nm, more preferably, between about 10 nm and 750 nm, even more preferably, between about 20-500 nm, and most preferably, between about 50 and 100 nm in diameter.

By the term "swollen configuration", we mean the microgel particle is substantially hydrated and enlarged, and therefore has a greater average diameter than the when the particle is in the collapsed configuration. It will be appreciated that this swelling is caused by a flow of water into the particle. In the swollen configuration, the microgel particle preferably comprises at least about 70% (w/w) water, more preferably, at least about 85% (w/w) water, preferably, at least about 90% (w/w) water, even more preferably, at least about 95% (w/w) water, and most preferably, at least about 99% (w/w) water. It will be appreciated that the amount of water in the particle will depend on the temperature and/or pH as well as the properties of the polymer making up the microgel particle (e.g. charge density). Suitably, the average diameter of the microgel particle is adapted to increase by at least 20%, more suitably, by at least 50%, more suitably by at least 100%, even more suitably, by at least 200% as it transitions from a collapsed to a swollen configuration in response to a change in the pH and/or temperature.

In an embodiment, the diameter of the microgel particles in the swollen configuration is about 5 nm to 100 µm, suitably about 5 nm to 10 µm, and preferably 50 nm to 1 µm.

For concentrated dispersions of microgel particles (e.g. concentrations greater than 2 wt. %), the transition from a collapsed configuration to a swollen configuration can be referred to as a pH or temperature dependent macrogelation step. The conformational change of the polymer causes solvent in the surrounding medium to ingress into the particle and cause it to swell. Thus, in the collapsed configuration the particles are dispersed in a substantially fluid medium, which has a low viscosity and can flow. Thus, in this configuration, the microgel particles can be easily transported to the desired location, for example, by injecting the particles to the desired location in the body. However, in the swollen configuration, the microgel particles form a gelled mass having a higher viscosity and a physical gel of higher viscosity.

For the particular application whereby the compositions of the invention are used for the treatment of damaged or degenerated load-bearing tissue, the polymer that makes up the microgel particle can be selected so that it transitions to a swollen configuration at physiological pH or temperature.

This means that the pH or temperature of the injection medium can be manipulated so that the microgel particles are in their compact configuration at the point of administration, thereby enabling them to be easily administered to the desired location by injection. The subsequent change in temperature and/or pH in the body will then cause the microgel particles to swell so that they contact adjacent microgel particles. The swollen microgel particles can then be bound together by the reaction between the vinyl groups provided on or proximate to the surface of the adjacent swollen microgel particles and/or by the formation of a cross-linked polymer network within the swollen microgel matrix. The result is a cohesive macrogel composition having advantageous mechanical properties.

In order for the microgel particles to swell, they need to be dispersed in a suitable aqueous medium. Water, buffer or physiological fluids are preferred.

The plurality of microgel particles used to form the compositions of the present invention may all possess the same polymeric composition, i.e. the same co-monomers are used to form the polymers that make up the microgel particles. However, in certain embodiments of the invention, the plurality of microgel particles may comprise two or more different types of microgel particle formed from polymers that are made up of different co-monomeric components or with different ratios of the same co-monomeric components.

A microgel dispersion is different to a hydrogel because it has the ability to flow and exist in the fluid state. A hydrogel cannot do that because it is a macroscopic (e.g., millimeter or centimeter sized material). The microgel dispersion consists of microgel particles dispersed within an (aqueous) solution. Because there is space between the particles they can flow and it is a fluid. However, using the pH-responsive microgel particles of the present invention, pH is used to trigger an increase in the size of the microgel particle so that they occupy the whole volume of the fluid. This causes formation of a (singly crosslinked) physical gel. In this state the peripheries of the microgel particles inter-penetrate.

The new method for DX microgel formation takes advantage of this by covalently coupling the peripheries of inter-penetrating vinyl-functionalised microgels. This gives a second level of crosslinking (double crosslinked) that links the microgel particles together.

pH-Responsive Microgel Particles

In a particular embodiment, the microgel particles are pH responsive. Any suitable pH-responsive microgel particles may be used to form the compositions of the present invention.

In a particular embodiment, the pH-responsive polymer is a polymer defined in WO2007/060424, the entire contents of which are incorporated herein by reference. In particular, suitable polymers for forming pH responsive microgel particles are defined at page 12/line 21 to page 22/line 17, and page 26/line 20 to page 28/line 22, of WO2007/060424. The microgel particles may be made by any suitable methods known in the art. Suitable initiators to use in the formation of such pH-responsive microgel particles are defined at page 22/line 19 to page 24/line 3 of WO2007/060424. Suitable surfactants that may also be used are defined at page 24/line 5 through to page 26/line 11.

For the compositions of the present invention, it is preferred that the microgel particle comprises a hydrophobic co-monomer. Hence, it is preferred that the microgel particle comprises a co-polymerised polymer particle, which may be defined by the following formula I:

Poly(B-co-P-co-X)     (I)

wherein:
P is a pH-responsive co-monomer;
X is a functional cross-linking co-monomer; and
B is a hydrophobic co-monomer.

These particular microgel polymers are described at page 19/line 21 through to page 22/line 8 of WO2007/060424, the relevant contents of which are incorporated herein by reference.

In a preferred embodiment, the microgel particle comprises ethylacrylate (i.e. EA, which is the hydrophobic co-monomer, B), methacrylic acid (i.e. MAA, which is the pH responsive co-monomer, P), and 1,4-butanediol diacrylate (i.e. BDDA, which is the functional cross-linking co-monomer, X). Accordingly, a preferred microgel particle comprises poly(EA/MAA/BDDA).

The poly(EA/MAA/BDDA) used to form the microgel particle may comprise a maximum mass % EA (hydrophobic monomer) of about 95%, a minimum mass % MAA (pH-responsive monomer) of about 5%, and a minimum mass % BDDA (cross-linking monomer) of about 0.1%. Suitably the mass % of BDDA is within the range of 0.1 to 2%.

In a particular embodiment, the poly(EA/MAA/BDDA) microgel particles comprise about 65.9% EA, about 33.1% MAA and about 1.0% BDDA based on the total monomer mass. This may be defined as a mass ratio of EA/MAA/BDDA as 65.9/33.1/1.0, or as a mole ratio of EA/MAA/BDDA is 130.4/76.0/1.0.

In another preferred embodiment, the microgel particle comprises methylmethacrylate (i.e., MMA, which is the hydrophobic co-monomer, B), methacrylic acid (i.e., MAA, which is the pH-responsive co-monomer, P) and ethyleneglycol dimethacrylate (i.e., EGDMA, which is the functional cross-linking co-monomer, X). Accordingly another preferred microgel particle comprises poly(MMA/MAA/EGDMA).

The poly(MMA/MAA/EGDMA) used to form the microgel particle may comprise a maximum mass % MMA (hydrophobic monomer) of about 95%, a minimum mass % MAA (pH-responsive monomer) of about 5%, and a minimum mass % EGDMA (cross-linking monomer) of about 0.1%. Suitably the mass % of EGDMA is within the range of 0.1 to 2%.

In a particular embodiment, the poly(MMA/MAA/EGDMA) of the microgel particles comprises about 66.8% MMA, about 32.8% MAA and about 0.4% EGDMA based on the total monomer mass. This may be defined as a mass ratio of MMA/MAA/EGDMA of 167/82/1.0, or as a mole ratio of MMA/MAA/EGDMA is 320/185/1.0.

In a particular embodiment, the composition or precursor composition as defined herein comprises microgel particles which swell or collapse as a consequence of a change in the pH of the surrounding environment. In a particular embodiment, the composition or precursor composition has a storage state and/or administration state having a pH environment which is different from the pH environment of the target site (e.g. physiological pH). In the storage or administration state, the microgel particles suitably exist in a substantially non-swollen state. The difference between the pH environment of the storage and/or administration state and the pH environment of the target site is suitably sufficient to cause the microgel particles to swell such that their hydrodynamic diameter ($d_h$) increases. Suitably, the pH at the target site causes the hydrodynamic diameter ($d_h$) of the microgel particles to increase relative to the storage or administration state by at least 10%, more suitably by at least 25%, even more suitably by at least 50%, and most suitably by at least 100%. The target site may suitably be in vivo, having a physiological pH environment.

Suitable pH-responsive microgel particles can be sourced commercially or prepared using methodology well known in the art.

Temperature-Responsive Microgel Particles

The microgel particles of the present invention may also be temperature responsive. Any suitable temperature-responsive microgel particles may be used to form the compositions of the present invention.

The term "temperature-responsive" is used herein to refer to polymers that undergo a temperature dependent change in hydration. The temperature at which a substantial change in polymeric hydration occurs is known as the critical solution temperature (CST). The lower critical solution temperature (LCST) is the critical temperature below which the co-polymer becomes highly miscible with water. Accordingly, above the LCST the co-polymer is highly dehydrated and below the LOST the co-polymer is highly hydrated. Suitable polymers of the present invention have an LCST within the range of 20° C. to 40° C. The desirable LOST will be dictated ultimately by the intended application of the microgel composition. For example, for in vivo application, it will be desirable to have a LOST above 37° C. For other applications, for example the provision of a temperature responsive microgel film for cell culture applications, a LOST of, for example, 30 to 34° C. may be required. An example of a polymer having a lower LOST of approximately 32° C. is Poly(N-isopropylacrylamide). The term "temperature-responsive" is also used herein to refer to monomers which, when polymerised, form temperature-responsive polymers that undergo a temperature dependent change in hydration as discussed above.

In a particular embodiment of the invention, the temperature responsive polymer used to form the microgel particles is a co-polymer of the following formula II:

$$\text{Poly(C-co-Q-co-X)} \qquad (II)$$

wherein:
C is a temperature responsive monomer;
Q is a monomer containing a hydroxyl group or a pH-responsive co-monomer P as defined hereinbefore; and
X is a cross-linking co-monomer as defined in WO2007/060424.

Any suitable temperature-responsive monomer (component C) may be used. Suitable examples of the temperature—responsive monomer C include N-isopropylacrylamide and vinylcaprolactone. Suitably, C constitutes 40 to 98 mol. % of the temperature responsive polymer.

A suitable example of Q is hydroxy ethyl methacrylate, vinyl alcohol, ethylene glycol methacrylate, or poly(ethylene glycol) methacrylate. Suitably, C constitutes 1 to 55 mol. % of the temperature responsive polymer.

As above, X suitably constitutes 0.01 to 2 mol. % of the temperature-responsive polymer.

The polymers used to prepare the microgel particles of the present invention may further comprise a monomer comprising a vinyl-containing side chain (in place of, or in addition to, the cross-linking monomer X). The vinyl containing side chain provides functional vinyl groups, at least a proportion of which will be on or proximate to the surface of the microgel particle and will therefore provide a means by which the microgel particles can react and bind to one another. A suitable example of such a monomer would be allyl methacrylate (AM). A suitable example of a polymer comprising allyl methacrylate is poly(EA/MAA/AM) as defined in Dalmont et al. (Langmuir, 2008, 24, 2834-2840).

Grafting of Vinyl-Containing Moieties

In a particular embodiment, the present invention provides a composition comprising a plurality of microgel particles, wherein adjacent microgel particles are covalently bound together by cross-linking groups formed by the reaction of vinyl-containing moieties grafted onto the microgel particles. As such, the precursor composition may suitably comprise microgel particles with vinyl-containing moieties grafted thereon.

It is predicted that the vinyl-containing moieties will be predominantly grafted on to the surface of the microgel particle, or proximate thereto.

The grafting of vinyl-containing moieties onto the preformed microgel particles provides a plurality of vinyl-containing moieties that can be subsequently reacted to form covalent cross-links between adjacent microgel particles.

Any suitable vinyl-containing moiety that can be grafted onto the microgel particle may be used for this purpose. Suitably, the vinyl-containing moiety is water soluble.

In an embodiment, the vinyl containing moiety is provided by reacting a microgel particle with a water soluble compound of the formula (III):

wherein:
Z is a reactive group;
L is a bond or linking group between Z and B; and
B is a group comprising a vinyl functional group.

Z may be any suitable reactive group. The purpose of the group Z is to react with a functional group present on the microgel particle and thereby graft the -L-B portion of the compound of formula III onto the particle surface to provide the vinyl-containing moiety. Thus, the selection of a suitable functional group Z will be dictated by the nature of the microgel particle concerned. A skilled chemist would be readily able to select suitable groups. For example, if the microgel particle comprises a carboxylic acid groups, then Z could be any group that will react to form an ester with the carboxylic acid group, such as, for example, a halogen, hydroxyl, amino or an epoxide group. Similarly, if the microgel particle comprises an amino group, then Z could be a group that reacts with the amine to form an amide bond (for example, Z could be a group —C(O)M, where M is a leaving group, e.g. a halogen such as chloro), or a group that reacts to form a sulfonamide linkage (e.g. Z is a group such as —S(O)$_2$Cl).

Alternatively, if the microgel particle comprises a carboxylic acid group (or groups), Z may suitably be an amino group, such as amino ethylmethacrylate (or salt thereof), and coupling may suitably lead to an acid amide. In such cases, compound III may suitably be coupled to the carboxylic acid group(s) following preactivation of the carboxylic acid group(s) (e.g. via the formation of an acyl-chloride) or using a coupling agent (e.g. 1-ethyl-3-(3-dimethylaminopropyl) carbodiimide (EDC), carbonyldiimidazole (CDl)). Z may suitably be alkylamino (or a salt thereof), for example ethylamine hydrochloride.

In a particular embodiment, Z is an epoxide group.

L may be bond or any suitable linker group, such as, for example, a functionalised alkylene chain optionally comprising one or more functional groups selected from —O—, —C(O)—, —C(O)O—, —OC(O)—, —NR$^a$—, —NR$^a$—C(O)—, or —C(O)—NR$^a$—, wherein R$^a$ is H or (1-2C)alkyl or L may be —(OCH$_2$CH$_2$)$_n$—, where n is 1 to 50 (inclusive). The alkylene chain may be a short (1-3 carbon atom) group comprising one or more of these functional groups defined above.

B may be any suitable vinyl-containing group. In a particular embodiment, B is a group —CR$_1$═CR$_2$R$_3$, i.e. the vinyl-containing moiety is a compound of structural formula IV shown below:

wherein Z and L are as defined above; and R$_1$, R$_2$ and R$_3$ are selected from H or (1-3C)alkyl.

R$_1$, R$_2$ and R$_3$ are suitably selected from H, methyl or ethyl, especially H or methyl.

In an embodiment of the invention, the compound of formula III or IV is selected from glycidyl methacrylate, glycidylacrylate or other functionalised glycyidylacrylates. Such compounds can be coupled to carboxylic acid, amine or hydroxyl groups on the microgel particle surface.

In a particular embodiment, the compound of formula III or IV is glycidyl methacrylate.

In an alternative embodiment, the compound of formula III or IV is allylamine, which can be covalently linked to carboxylic acid groups on the microgel particle surface using water-soluble carbodiimide chemistry.

In an alternative embodiment, the compound of formula III or IV is aminoethyl methacrylate hydrochloride (AEM-HCl). Such compounds may suitably be coupled to a carboxylic acid group(s) upon the microgel particles through a coupling reaction involving EDC.

A person skilled in the art will be able to select suitable experimental conditions to graft the vinyl-containing moiety onto the microgel particle.

Suitably, the reaction will be carried out in the aqueous solvent at a pH of between 2 and 7, and preferably at a pH of between 2 and 4.

Suitably, the concentration of the microgel particles in the aqueous solvent is between 0.05 and 20 wt. %.

Suitably, the concentration of the vinyl-containing group (e.g. glycidyl methacrylate, glycidylacrylate or other functionalised glycyidylacrylates) is between 10$^{-3}$ and 10 Mol dm$^{-3}$, and preferably between 0.1 and 5 Mol dm$^{-3}$.

A suitable temperature for the grafting reaction is between 0 and 100° C., and preferably between 40 and 70° C. The reaction may proceed for between 0.5 and 48 hours, and preferably between 4 and 12 hours.

Suitably the vinyl-containing moiety should correspond to a concentration of between 0.1 and 60 mol. % with respect to all of the co-monomers present in the gel. Preferably, the concentration of the vinyl-containing moiety should be between 10 and 30 mol. % with respect to all of the co-monomers present in the gel.

Cross-Linking of the Vinyl-Grafted Microgel Particles

The vinyl-containing moieties grafted onto the surface of the microgel particles may undergo a free-radical coupling reaction directly with the vinyl-containing moieties grafted onto the surfaces of adjacent microgel particles to form a direct covalent bond therebetween.

Figure 2:
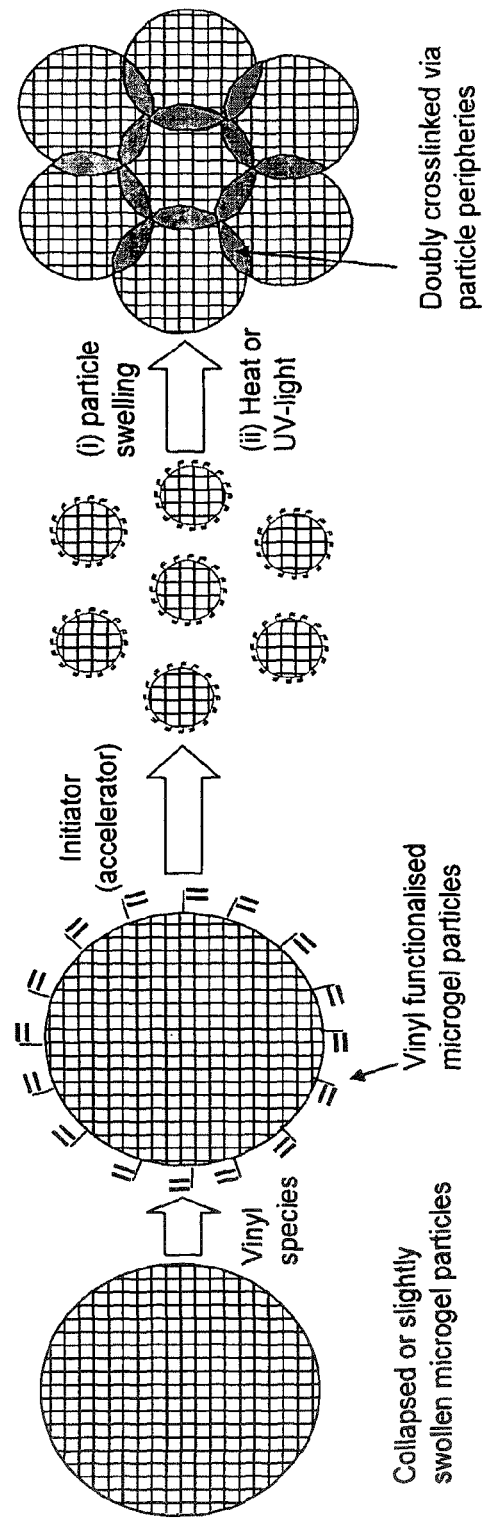
FIG. 2 is a scheme showing a second method for preparing a cross-linked microgel particle composition of the present invention.

This particular reaction is shown schematically in FIG. 2. The first step of the reaction involves providing microgel particles that have vinyl-containing moieties grafted on to their surfaces. The next step involves bringing the surfaces of the adjacent particles into contact with one another. This can be achieved by causing the responsive microgel particles to swell by varying the temperature or pH (as described hereinbefore). The swelling of the microgel particles as they hydrate causes the surfaces of adjacent particles to contact one another and even overlap to form interpenetrating regions of gelled polymer. This disposes the surface grafted vinyl-containing moieties of adjacent microparticles in close proximity to one another to facilitate the free-radical coupling of the vinyl moieties, as discussed further below.

The reaction between the vinyl-containing moieties grafted onto the surface of adjacent microgel particles is achieved by free-radical chemistry using techniques well known in the art. A key feature of the present invention is that the reaction must take place in the aqueous medium, so suitably water soluble reactants need to be used. For in vivo applications it is also preferred that the any reactants used possess little or no toxicity to the subject.

Suitably, the reaction is conducted in the presence of a free radical initiator (hereinafter referred to as an initiator), which is water soluble. Suitably, the initiator is responsive to temperature or ultraviolet radiation.

Suitable water soluble initiators include:

Anionic Initiators:

initiators of the general formula $[M]S_2O_8^{2-}$, wherein M is a cation such as $K^+$, $Na^+$ or $NH_4^+$, or a divalent cation. Ammonium persulfate, $(NR_4^+)_2S_2O_8^{2-}$, is a specific example.

an organic anionic azo initiator of formula V:

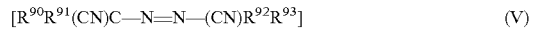

$$[R^{90}R^{91}(CN)C-N=N-(CN)R^{92}R^{93}] \quad (V)$$

wherein:

$R^{90}$ and $R^{92}$ may be independently selected from a group consisting of H; $CH_3$; a linear or branched (1-10C)alkyl group; or a —NH-(1-10C)alkyl or —N[(1-10C)alkyl]$_2$ group; and $R^{91}$ and $R^{93}$ may be $CR^{94}COOH$ (wherein $R^{94}$ may be —CH$_2$—, —CH$_2$CH$_2$— or a linear, or branched (1-20C)alkylene chain) or phenyl which is optionally substituted (for example, by one to three substituent groups selected from halo, (1-6C)alkyl, amido, amino, hydroxy, nitro, and (1-6C)alkoxy).

A particularly suitable initiator belonging to this group is azobiscyanopentanoic acid (also known as 4,4'-azobis (4-cyanovaleric acid)).

Cationic Initiators:

a cationic amine initiator of structural formula VI:

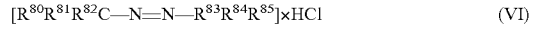

$$[R^{80}R^{81}R^{82}C-N=N-R^{83}R^{84}R^{85}] \times HCl \quad (VI)$$

wherein $R^{80}$, $R^{81}$, $R^{83}$ and $R^{84}$ may be independently selected from a group consisting of H; $CH_3$; a linear or branched (1-10C)alkyl group; a —NH-(1-10C) alkyl or —N[(1-10C)alkyl]$_2$ group; and wherein $R^{82}$ and $R^{85}$ may be C(=NR$^{86}$)NH$_2$ wherein $R^{86}$ may be independently selected from a group consisting of H; $CH_3$; a linear or branched (1-10C)alkyl group.

For example, a specific example is propanimidamide, 2,2'-azobis[2-methyl-, dihydrochloride]. This initiator is also known as V50.

Peroxide Initiators:

a peroxide initiator defined by the structural formula VII:

$$R^{70}-O-O-R^{71} \quad (VII)$$

wherein $R^{70}$ or $R^{71}$ may be independently selected from a group consisting of H; $CH_3$; a linear or branched (1-10C)alkyl group; a —NH-(1-10C)alkyl or —N[(1-10C)alkyl]$_2$ group; or phenyl which is optionally substituted (for example, by one to three substituent groups selected from halo, (1-6C)alkyl, amido, amino, hydroxy, nitro, and (1-6C)alkoxy).

Suitable water soluble ultraviolet photoinitiators are of the formula VIII:

$$R^{52}\text{-ph-}R^{53} \quad (VIII)$$

where $R^{52}$ is HO—(CH$_2$)$_2$— and $R^{53}$ is —C(O)C(OH) (CH$_3$)$_2$ and ph represents a phenyl ring.

A particular initiator according to this formula is known as Irgacure 2959.

The free-radical coupling reaction may also be conducted in the presence of a suitable water soluble accelerator. Suitable examples of such accelerators include TEMED (1,2-bis(dimethylamino)ethane, N,N,N',N'-Tetramethylethylenediamine) and ascorbic acid (also known as DL-ascorbic acid).

A skilled chemist will be able to select appropriate experimental conditions in order to carry out the vinyl coupling reactions.

The swelling of the microgel particles can be initiated by varying the temperature and/or pH. The temperature and/or pH required will depend on the polymeric components of the microgel particles. Typically all temperature responsive microgel particles will swell within a temperature range of 0 to 100° C., and suitably within the range of 20 to 80° C. For in vivo applications where the in situ cross-linking of the microgel particles may be required, it is preferred that the microgel particles swell at body temperature and/or the pH of the target tissue.

The vinyl coupling reaction may proceed at any suitable temperature. Temperatures ranging from 0 to 100° C., and suitably from 20 to 80° C. may be used. Again, for in vivo applications where the in situ cross-linking of the microgel particles may be required, it is preferred that the cross-linking reaction proceeds at normal body temperature.

The quantity of the microgel particles required for the vinyl coupling reaction is suitably 1 to 60 wt. %, and preferably from 10 to 20 wt. %, of the reaction medium.

The concentration of initiators should be in the range of 0.01 to 10 wt. % with respect to water. The preferred concentration is 0.1 to 2 wt. % with respect to water.

Any suitable pH range may be used for the vinyl-coupling reaction. The pH range should include the $pK_a$ for the microgel polymer if it is a pH-responsive microgel particle. Again, for in vivo applications where the in situ cross-linking of the microgel particles may be required, it is preferred that the vinyl-coupling reaction proceeds at physiological pH. The pH range used during the binding of the microgel particles for poly(MMA/MAA/EGDMA) microgel particles is 6.0 to 9.0, and is preferably 7.0 to 8.0.

The swelling ratio ($q=V/V_{coll}$) defines the degree of swelling of the microgel particles. V is the microgel particle volume measured in a partially swollen or fully swollen configuration. $V_{coll}$ is the volume of the non-swollen, collapsed configuration of the microgel particles. The value for q during vinyl-coupling reaction should be 1.1-500. Preferably, the value for q should be 3-100.

If ultraviolet photoinitiation is being used, then the intensity of UV-irradiation required is, for example, half a minute to 2 hours of exposure under a UV lamp providing a light intensity in the range of 0.1-100 mW/cm$^2$. In a particular embodiment, the exposure is for 3 minutes.

Cross-Linking of Microgel Particles by Forming an Interpenetrating Polymer Network An alternative approach to bind the microgel particles together is shown schematically in FIG. 1. The first step of the reaction involves providing the microgel particles (without any vinyl-containing moieties grafted onto the particles). The next step involves bringing the surfaces of the adjacent particles into contact with one another in the presence of a cross-linking monomer comprising two or more vinyl groups. This can be achieved by causing the responsive microgel particles to swell (by varying the temperature or pH as described hereinbefore) in the presence of the cross-linking monomer. The hydration and swelling of the microgel particles causes the surfaces of adjacent particles to contact one another and overlap to form interpenetrating regions of gelled polymer. The free-radical initiated polymerisation of the vinyl-containing cross-linking monomer can then be initiated. The result is the formation of a cross-linked interpenetrating polymer network within the swollen microgel particles. This network binds the microgel particles together to form a cohesive gel structure.

By "interpenetrating polymer network" we mean that the polymer network is formed within the swollen microgel particles and extends from one microgel particle to another. The polymer network is formed in situ and between the swollen particles by the polymerisation of the water soluble monomers that diffuse into the swollen microgel particles as they hydrate.

An advantage of this method is that the addition of the water-soluble crosslinking monomer provides a useful tool for tuning the mechanical properties of the precursor. For instance, a low molar mass crosslinker (e.g., EGDMA) may be absorbed into the inter-penetrating microgels, and thereby links them together. The precursor microgel dispersion in that case is a physical gel.

A higher molar mass crosslinker (e.g., PEGDMA550) may be excluded from the microgel particle interior and, as such, an osmotic deswelling mechanism may be responsible for partially de-swelling the microgel particles. In that case the precursor dispersion is a fluid (even when the pH has been increased). Crosslinking may result in formation of a hydrogel matrix that encapsulates the microgel particles. This network may to some extent inter-penetrate the peripheries of the microgel particles.

It can be seen that the molar mass of the added water-soluble polymer plays a major role in the physical properties of the microgel dispersion precursor and also the mechanical properties of the final DX microgels.

The vinyl polymerisation reaction can be carried out using the water-soluble initiator as described above.

A water soluble accelerator as described herein may also be present.

Suitable reactions conditions for the polymerisation reaction will be well known to those skilled in the art and reference is also made to the general conditions described hereinbefore for the vinyl-coupling reactions.

Any suitable water-soluble cross-linking monomer may be used to form the interpenetrating polymer network that binds the microgel particles together. For in vivo applications, it is necessary that the monomers (and the resultant interpenetrating polymer network formed) are biocompatible. To be water-soluble a crosslinker may suitably have some water solubility, for instance, ranging from $10^{-6}$ to 100 wt. % with respect to the water phase. In particularly embodiments, the crosslinker has a water solubility of at least 0.1 wt %, suitably at least 1 wt %, or suitably at least 10 wt %.

Suitably, the cross-linking monomer will comprise two or more vinyl groups to enable a highly cross-linked interpenetrating polymer network to be formed.

In an embodiment, the molar mass of the cross-linking monomer is suitably 220 to 750 g/mol, suitably 350 to 600 g/mol, or more suitably 500 to 600 g/mol.

Suitably, the vinyl cross-linking monomer has the following formula:—

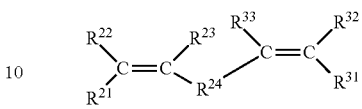

wherein:
(a) $R^{21}$, $R^{22}$, $R^{23}$, $R^{31}$, $R^{32}$ and $R^{33}$ may be independently selected from a group consisting of H; $CH_3$; a linear or branched alkyl group; or a N-alkyl group of up to 10 C units; and
wherein (b) $R^{24}$ may be independently selected from a group consisting of:—
(i) —C(=O)—O—$R^{34}$—O—C(=O)—, wherein $R^{34}$ may comprise —$CH_2$—, —$CH_2CH_2$— or a linear or branched alkyl group, such as a methylene chain, which may be up to 20 C chains in length; or —$C_6H_4$—; or $C_6H_3R^{35}$, wherein $R^{35}$ comprises substituents such alkyl, for example, $CH_3$; a halogen group; or an amide group; or other di- or tri-substituted phenyl groups containing more than one of these substitutents;
(ii) —C(=O)—O—$R^{36}$—C(=O)—, wherein $R^{36}$ may be —$(CH_2CH_2O)_n$—wherein n may be from 1 to 30;
(iii) —C(=O)—O—$R^{37}R^{38}R^{37}$—, wherein $R^{37}$ may comprise degradable ester linkages, for example lactone, —$[(CH_2)_5C(=O)—O]_m$—, lactide, —$[CH(CH_3)C(=O)—O]_m$—, glycolide, —$[CH_2C(=O)—O]_m$—, wherein m may be from 1 to 50, and wherein $R^{38}$ may be —$(CH_2CH_2O)_m$—, wherein n may be from 1 to 30;
(iv) —C(=O)—O—$R^{39}$—, wherein $R^{39}$ may comprise degradable ester linkages, for example lactone, $[(CH_2)_5C(=O)—O]_m$—, lactide, $[CH(CH_3)C(=O)—O]_m$—, glycolide, $[CH_2C(=O)—O]_m$—, wherein m is between 1 to 100;
(v) allylacrylates, for example —C(=O)—O—$R^{40}$—, wherein $R^{40}$ may be —$CH_2$—, —$CH_2CH_2$— or a linear, or branched, methylene chain up to 20 C chains in length, or —$C_6H_4$—, $C_6H_3R^{41}$, wherein $R^{41}$ may comprise substituents, such as alkyl, $CH_3$, a halogen or an amide group or other di- or tri-substituted phenyl groups containing more than one of these substitutents;
(vi) vinylbenzenes, for example $C_6H_4$ or $C_6H_3R^{42}$ wherein $R^{42}$ comprises substituents, such as alkyl; $CH_3$; a halogen or an amide group (see (iii) above); or other substituted phenyl groups containing more than one of these substitutents;
(vii) acrylamides, for example C(=O)—$NR^{43}$—$R^{44}$—$NR^{45}C(=O)$—, wherein $R^{43}$ and $R^{44}$ may be independently selected from a group consisting of H; $CH_3$; a linear or branched alkyl group; a dialkyl group; a N-alkylgroup, of up to 10 C units; and wherein $R^{44}$ may comprise —$CH_2$-, —$CH_2CH_2$— or a linear, or branched, methylene chain up to 20 C chains in length; or —$C_6H_4$—, $C_6H_3R^{41}$ wherein $R^{41}$ comprises substituents, such as alkyl; $CH_3$; a halogen or an amide group or other di- or tri-substituted phenyl groups containing more than one of these substitutents;
(viii) trifunctional cross-linking monomers, wherein $R^{24}$ comprises any of the groups listed in (b), as well as $R^{21}R^{22}C=CR^{23}$, where $R^{21}$, $R^{22}$ and $R^{23}$ are described in (a);

(ix) tetrafunctional cross-linking monomers, wherein $R^{24}$ comprises any of the groups listed in (b), as well as $R^{21}R^{22}C=CR^{23}$ and $R^{31}R^{32}C=CR^{33}$, wherein $R^{21}$, $R^{22}$, $R^{23}$, $R^{31}$, $R^{32}$ and $R^{33}$ are described in (a); and (x) wherein $R^{24}$ may contain any combination of the groups listed in (b).

However, it is preferred that the monomer comprises a further functional (preferably, a di- or a higher functionality) cross-linking monomer such as, for example, a substituted functional acrylate. Hence, the monomer may comprise allylmethacrylate or divinylbenzene. Hence, the monomer may comprise butanediol diacrylate. However, preferably, the monomer comprises ethyleneglycol dimethacrylate.

The functional cross-linking co-monomer may have other groups in between the terminal vinyl groups, for example poly(ethyleneglycol)dimethacrylate (PEGDMA).

The preferred vinyl cross-linking monomer from the point of view of intervertebral disc repair is PEGDMA with a molar mass in the range of 200 to 1000 g/mol. Preferably, the molar mass should be between 220 and 750 g/mol, more preferably 300 and 600 g/mol. The most preferred vinyl cross-linking monomer is EGDMA.

Figure 3:
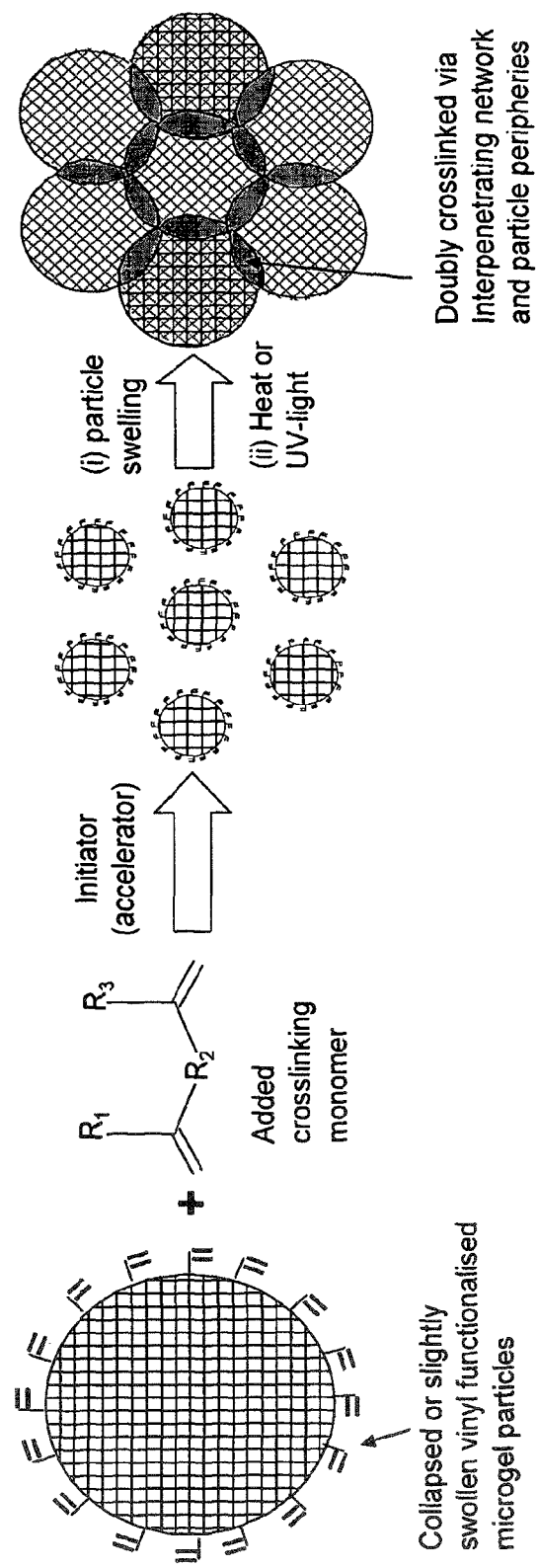
FIG. 3 is a scheme showing a third method for preparing a cross-linked microgel particle composition of the present invention.

Cross-Linking of the Vinyl-Grafted Microgel Particles Combined with the Formation of an Inter-Penetrating Polymer Network FIG. 3 shows a further alternative embodiment of the present invention which is a combination of the approaches shown in FIGS. 1 and 2.

Thus, the compositions formed by this approach comprise a plurality of microgel particles bound together by the reaction of vinyl-containing moieties grafted onto the surfaces of the microgel particles and by a cross-linked polymer network that interpenetrates adjacent microgel particles (and thereby further binds the particles together), wherein the polymer network is formed by the polymerisation of a water soluble cross-linking monomer comprising two or more vinyl groups.

In a particular embodiment, the microgel particles are formed from poly(MMA/MAA/EGDMA) and glycidyl-methacrylate is grafted onto the surface to provide the functional vinyl groups. These "functionalized" microgel particles are then subject to a vinyl coupling reaction as defined herein in the presence of a cross-linking monomer, such as PEGDMA having a molar mass in the range of 300 to 600 g/mol.

This method combines the benefits of directly cross-linking the vinyl-grafted microgel particles and cross-linking of microgel particles by forming an interpenetrating polymer network. The interpenetrating network may be considered a reinforcement of the directly doubly-cross-linked microgel, but also provides a further means to tune the mechanical properties of the precursor dispersion and DX microgel properties using the molar mass of the water soluble crosslinker.

Properties of the Bound Microgel Particle Compositions of the Invention

The microgel compositions of the present invention belong to the class of materials known as hydrogels. They differ from conventional hydrogels because they are composed of bound or linked microgel particles.

The elastic modulus (G') of the compositions of the invention will be dependent on the method used for their preparation. The values for G, as measured by dynamic rheology, will typically be greater than 10 Pa (without any upper limit). The values for the loss modulus (G") will be less than the elastic modulus for each composition of the invention because of their classification as hydrogels.

The swelling characteristics of the compositions of the invention can again be defined by the swelling ratio (as defined hereinbefore). The value for q will typically be between 1.2 and 500. For the specific application of intervertebral disc repair, the swelling ratio is preferred to be between 3 and 200.

The compositions of the invention, like the component microgel particles, will be temperature and/or pH-responsive. Temperature-responsive compositions will be in the swollen configuration at temperatures below the LCST and in the collapsed configuration at temperatures above the LOST. The q value for such compositions will typically be between 1.2 and 200. The elastic moduli will have the same minimum values as specified above.

For pH-responsive compositions of the invention comprising microgel particles composed of acidic monomers, the particles will be in a swollen configuration at pH values greater than the $pK_a$ of the acidic monomers and in the collapsed configuration at pH values less than the $pK_a$ value of the acidic monomers. The $pK_a$ values may be in the range of 1 to 13. The preferred range for the intervertebral disc application is 5.0 to 8.0.

For pH-responsive compositions of the invention comprising microgel particles composed of basic co-monomers, the particles will be in the swollen configuration at pH values less than the $pK_a$ of the conjugate acid of the basic monomers and in the collapsed configuration at pH values greater than this $pK_a$ value. The $pK_a$ values may be in the range of 1 to 13.

The microgel compositions of the present invention suitably have significant critical strain values ($\gamma^*$). The critical strain value is the value for the strain, measured by a rheometer, at which the elastic modulus (G') first reaches a value of 95% of that measured when $\gamma=1.0\%$. The preferred range for $\gamma^*$ for the compositions of the invention is 2 to 500%, more preferred is 5 to 300%, and even more preferred is 5 to 200%.

Applications

The compositions (including precursor compositions) of the present invention may be used for a variety of different applications, including applications in drug delivery, photonics, catalysis, information storage, or they may be used as absorbent materials.

It is envisaged that compositions (or precursor compositions) of the present invention will be particularly suitable for medical applications. It is particularly envisaged that compositions of the present invention may be used to repair damaged or degenerated soft tissue in a subject.

Thus, the present invention provides a composition (or precursor composition) as defined herein for use in the treatment of damaged or degenerated tissue, especially damaged or degenerated load-bearing tissues.

In a further aspect, the present invention provides a method of treating damaged or degenerated tissue, especially damaged or degenerated load-bearing tissues, in a subject in need of such treatment, the method comprising administering a therapeutically effective amount of a composition (or precursor composition) as defined herein.

Suitably, a composition of the invention is formed in situ within the body (e.g. from a precursor composition). Therefore, the microgel particles are administered together with any other materials required to bind the microgel particles together (e.g. reactants required for the vinyl coupling reactions) and thereby form a composition of the present invention in situ within the body. By "together with" we mean that one or more of the reactants are either co-administered with the microgel particles, administered before the microgel particles or administered after the microgel particles.

Thus, in one embodiment, the microgel particles having vinyl-containing moieties grafted onto their surfaces are administered together with a water soluble initiator and, optionally, a water soluble accelerator.

In another embodiment, microgel particles (without vinyl-containing moieties grafted onto the surface) are administered together with the cross-linking monomer (that forms an interpenetrating polymer network following polymerisation) and a water soluble initiator and, optionally, a water soluble accelerator.

In a further embodiment, microgel particles having vinyl-containing moieties grafted onto their surfaces are administered together with a vinyl cross-linking monomer (that forms an interpenetrating polymer network) and a water soluble initiator and, optionally, a water soluble accelerator.

Additional components, such as a suitable vehicle, buffering agents, acids, bases, or other pharmaceutically acceptable excipients may also be administered together with the microgel particles and any other reactants.

In one embodiment, the microgel particles are administered in the collapsed or substantially collapsed configuration, which makes the particle composition more fluid and therefore easier administer by, for example, injection. When the microgel particles in the collapsed configuration reach the intended site, the particles preferably swell as a consequence of a change in the pH and/or temperature, and the vinyl coupling reaction can then be initiated to form a composition of the present invention in which the microgel particles are bound together.

In a particular embodiment, the microgel particles are pH-responsive and are adapted to be in a swollen or substantially swollen configuration at the physiological pH of the target tissue. The pH of the administered composition can then be manipulated so that the particles are in a collapsed configuration at the time of administration, but then swell within the target tissue. The rate of swelling may be increased by the administration of a physiologically acceptable acid, base or buffer solution, either with or after the administration of the microgel particles.

For example, if the microgel particles are being administered to an IVD in a subject, it is known that the average pH of the IVD is about 7.5. Microgel particles that are in a swollen or substantially swollen configuration at a pH of between 6.5 and 8, more preferably between 6.6 and 7.5, would be particularly suitable for administration to an IVD. The pH of the microgel particle composition administered to the subject could then be manipulated so that the microgel particles are in the collapsed or substantially collapsed configuration at the point of administration. In an embodiment, the microgel particles are maintained at a pH of less than 6.6, such that upon administration into the IVD, the particles will swell and cause gelation of the composition. In such an embodiment, the particles may be maintained in the collapsed configuration at a pH of between about 5.0 to 6.6, more preferably between about 5.5 to 6.6, and even more preferably between about 6.0 to 6.6 before administration. At these pH values, the diameter of the microgel particles is suitably between about 50-200 nm, and most preferably, about 80 to 150 nm (as measured by Scanning Electron Microscopy). Accordingly, the increase in pH from less than 6.6 to about 7.5 in vivo causes water to enter the particles such that they swell. When administered to a damaged or degenerated IVD, the swelling and in situ cross-linking of the microgel particles provides a composition of the invention which provides additional load bearing support to the IVD.

In an alternative embodiment, the microgel particles are administered in a swollen or substantially swollen configuration. Suitably, the microgel particles are caused to swell just prior to administration. An advantage of this approach is that the microgel particles arrive at the target tissue in swollen form that is suitable for rapid cross-linking to form a composition of the invention. For example, pH-responsive microgel particles may be administered in a swollen or substantially swollen configuration at a pH of, for example, 7.5 to 7.8.

In a particular embodiment, the microgel particles are administered in the collapsed or substantially collapsed configuration, and allowed to swell in situ. The cross-linking reactants (the initiator and, optionally an accelerator and a cross-linking monomer (if an interpenetrating polymer network is to be formed)) are added once the microgel particles are sufficiently swollen for cross-linking to occur.

In a preferred embodiment, the microgel particles are administered in the swollen or substantially swollen configuration and the cross-linking reactants (the initiator and, optionally an accelerator and a cross-linking monomer (if an interpenetrating polymer network is to be formed)) are co-administered or administered immediately after the administration of the microgel particles.

It may be preferred to contact the composition comprising the microgel particle with a physiologically acceptable acid, base (e.g. NaOH or KOH) or buffer to facilitate a change in the pH and thereby accelerating gelation in vivo. It will be appreciated that a physiologically acceptable acid, base or buffer may be administered to the target tissue either before or after the composition comprising the microgel particle has been administered. Alternatively, a co-administration procedure may be used where both the composition comprising the microgel particles, and a physiologically acceptable buffer are administered substantially at the same time. This may be achieved for example through a specially constructed syringe needle.

Suitably the reaction vinyl cross-linking reaction occurs promptly after the administration (before the initiator and optionally the accelerator diffuse away from the site of administration). It is therefore preferred that the initiator and optionally the accelerator are either co-administered with the microgel particles or administered immediately after the microgel particles. Any cross-linking monomer that reacts to form an interpenetrating polymer network to bind the particles together may be co-administered with the microgel particles or administered prior to or after the administration of the microgel particles.

As a result of the in situ formation of the composition of the invention within a subject, there is preferably, an increase in disc height and also the Young's Modulus of the IVD as the composition forms, and the mechanical strength is effectively restored. Advantageously, this provides a minimally invasive method that can fill the interior of any irregularly shaped clefts in the IVD. Hence, this minimally invasive method does not involve any major surgical intervention, thereby meaning the subject being treated is likely to have a much curtailed recovery time.

Another advantage of the method is that it does not require removal of any healthy tissue. This is in direct contrast to nucleus replacement technologies which involve microdiscectomy and removal of nucleus pulposus tissue.

In another embodiment, the composition administered to form the composition of the invention may comprise at least one nucleus pulposus cell and/or at least one stem cell and/or at least one mammalian cell.

Examples of suitable mammalian cells, which may be added to the composition include chondrocytes (e.g. autologous or autogenous). Examples of suitable stem cells, which may be added to the composition include mesenchymal, haematopoeic etc., including embryonic and cloned stem cells. In addition, the composition administered may further comprise collagen and/or proteoglycans. It will be expected that adding nucleus pulposus cells to the composition will increase the rate of recovery of the subject. Hence, a further advantage of the method according to the invention is that it allows mixing of living cells (e.g, NP cells or stem cells) with the composition comprising the microgel particle dispersion in order to facilitate re-growth of NP tissue. Thus, the method according to the invention is amenable to combining mechanical support with a biological repair system.

Examples of suitable soft tissues which may be treated include skin, muscle, ligament, or adipose tissue. Such damaged or degenerated soft tissue may comprise a wound, which may be either acute or chronic. However, it is preferred that the soft tissue being treated comprises damaged or degenerated load-bearing tissue such as, for example, intervertebral discs and the tissues found in articular joints (such as the elbow, knee, hip, wrist, shoulder and ankle). In addition, the compositions of the invention may be used to treat low-load bearing joints, such as, for example, the joints present in a finger or a thumb.

It is most preferred that the compositions of the present invention are used to treat damaged or degenerated vertebral, or intervertebral discs (IVDs). Preferably, the method of the second aspect comprises administering the composition directly into the IVD, and preferably into the nucleus pulposus (NP) thereof. Hence, advantageously, no surgery is required using this approach. More preferably, the composition may be administered directly into clefts within the NP, which form when the proteoglycan content in the IVD decreases with age. Furthermore, it is preferred that the components required to form the composition of the invention are administered by injection into the target tissue.

Disease conditions, which may be treated with the medicament of the first aspect or the method according to the second aspect include arthritis, intervertebral disc degeneration, back pain, low back pain, sciatica, cervical, spondylosis, neck pain, kyphosis, scoliosis, degenerative joint disease, osteoarthritis, spondylolysis, spondylolisthesis, prolapsed intervertebral disc, failed spine surgery, and spinal instability. The disease condition may be chronic or acute, for example, chronic or acute back pain.

In a particular embodiment, the composition of the invention is used for the treatment of osteoarthritic conditions in joints as an alternative to cartilage replacement. In such embodiments, the composition of the invention is formed by in situ within the joint by injecting the components required to form the composition of the invention into the joint capsule of an osteoarthritic joint. The composition of the invention would then provide a means of keeping the bone ends apart.

The swelling pressure of the gels of the present invention can be adjusted using pH and/or temperature in order to increase the effective Young's Modulus of the microgel-loaded soft tissue. Furthermore, the inventors believe it should be possible to adjust the pKa of these microgels by varying the chemical composition of the particles, which will allow fine-tuning of the load-bearing properties of these materials at the pH of the damaged load-bearing tissue.

It will be appreciated that the composition according to the present invention may be used in a monotherapy (i.e. use of the composition according to the invention alone to prevent and/or treat diseases characterised by damaged or degenerated soft tissue, and preferably, load-bearing tissue). Alternatively, the microgel particle according to the invention may be used as an adjunct, or in combination with other known therapies.

Compositions comprising the microgel particle according to the invention may be used in a number of ways. Preferably, the composition may be administered by injection.

The therapy may be given as a single administration (e.g. a single injection). Alternatively, the composition used may require repeated administration at predetermined intervals.

The invention further provides a pharmaceutical composition comprising a therapeutically effective amount of a microgel particle together with reactants to form the composition of the invention in situ within the body. A "therapeutically effective amount" is any amount of a microgel particle according to the invention which, when administered to a subject forms a composition of the invention that prevents and/or treats a disease characterised by damaged or degenerated soft tissue.

In a further aspect, the present invention provides a kit of parts comprising microgel particles as defined herein (optionally in the presence of a suitable vehicle/dispersion medium) and one or more cross-linking reactants as defined herein. The reactants suitable comprise an initiator as hereinbefore defined, and may further comprise an accelerator and/or a cross-linking monomer as hereinbefore defined. Suitably, the kit further comprises instructions explaining how to administered the contents for in situ gel formation.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

EXAMPLES

The invention will now be described in more detail in relation to the following illustrative examples.

Physical Measurements

Unless stated otherwise, the following methodology was used to obtain physical measurements.

Titration measurements were performed using a Mettler titration unit in the presence of a supporting electrolyte (0.1 M NaCl). Photon correlation spectroscopy measurements were performed using dispersions containing $\phi_p = 3 \times 10^{-4}$ microgel. The measurements were conducted using a BI-9000 Brookhaven light scattering apparatus (Brookhaven Instrument Cooperation), fitted with a 20 mW HeNe and the detector was set at 90° scattering angle. The extent of particle swelling is characterised in terms of the estimated swelling ratio, Q. This is given by the following equation.

$$Q = \left(\frac{d}{d_{coll}}\right)^3 \quad (1)$$

For equation (1) d and $d_{coll}$ are the diameters of the measured using photon correlation spectroscopy (PCS) at a given pH and the collapsed particle size, respectively. In this work the values for $d_{coll}$ were those obtained at pH=4 unless otherwise stated. SEM measurements were obtained using a Philips FEGSEM instrument. Samples were dried at room temperature or by freeze drying. At least 100 particles were counted for particle size estimations. Dynamic rheology measurements were performed using a TA instrument AR G2 temperature-controlled rheometer with an environmental chamber. A 20 mm diameter plate geometry with a solvent trap was used. The gap was 1000 nm.

Swelling experiments for the DX (cross-linked) microgels of the present invention were performed by placing samples in buffer and then allowing the sample to equilibrate with gentle agitation for a period of at 8 days. The buffer was regularly changed. Periodically, the sample was removed, patted dry with paper towel, weighed and then immediately returned to the buffer solution. The buffer solutions used were phosphate or phthalate based, had an ionic strength of about 0.1 M, and were prepared as described elsewhere (J. Brandrup, E. H. Immergut, E. A. Grulke, A. Abe, and D. R. Bloch (1999) CRC Polymer Handbook, 4 ed., John Wiley & Sons). The volume swelling ratio for those DX microgels ($Q_{DX}$) were determined gravimetrically and calculated using:

$$Q_{DX} = \rho_p \left( \frac{Q_{DX(m)}}{\rho_s} + \frac{1}{\rho_p} \right) - \frac{\rho_p}{\rho_s} \quad (2)$$

For equation (2) $Q_{DX(m)}$ is the ratio of the swollen gel mass to the dry mass. $\rho_s$ and $\rho_p$ are the densities of the solvent and polymer, respectively. These were taken as 1.2 and 1.0 $gcm^{-3}$.

Method 1—Preparation of Poly(MMA/MAA/EGDMA) Microgel Particles

Poly(MMA/MAA/EGDMA) was prepared using emulsion polymerisation. A water bath was heated to 80° C. 1.8 g sodium dodecylsulfate (SDS) was dissolved in 517.5 g deionised (DI) water. The solution was then filtrated to a four necked flask and nitrogen purged for 30 minutes. The monomer mixture was prepared with following composition: MMA (189.76 g), MAA (94.87 g) and EGDMA (2.882 g). This includes 15% excess in order to account for loss during the feed stage. After SDS dissolution, 31.5 g of monomer mixture (seed) was added, whilst stirring, to the vessel followed immediately by adding respectively $K_2PO_4$ solution (0.2264 g in 2.93 g DI water) and ammonium persulfate (APS) solution (0.2 g in 3.39 g DI water). The mixture was left to stir for a further 30 minutes and temperature was raised to 88° C. The remaining monomer mixture was added over 90 min at a rate of approximately 2.5 ml/min. After the feed was complete an APS solution was added (0.0874 g in 3 g DI water). The dispersion was left to stir at least for 2 hours until no monomers could be detected and then cooled with water and ice mixture while being stirred. The cooled product (a milky dispersion) was filtered. This microgel contained a nominal concentration of 66 wt. % MMA, 33 wt. % MAA and 1 wt. % EGDMA.

Method 1A—Preparation of Poly(MMA/MAA/EGDMA) Microgel Particles

Poly(MMA/MAA/EGDMA) was also prepared using the following method. 1.8 g SDS in 517.5 g DI water was added to a four-necked round bottom equipped with a mechanical stirrer and reflux condenser. The contents were purged with nitrogen for 30 minutes at 80° C. To form the seed, 31.5 g of a solution of MMA (66 wt %), MAA (33 wt %) and EGD (1 wt %) was added to the vessel followed immediately by adding, respectively, $K_2HPO_4$ (3.15 g of 7 wt. % solution) and ammonium persulfate (APS, 3.5 g of 5 wt. % solution). The seed was left to stir for a further 30 minutes and the temperature was raised to 85° C. The remaining 218.5 g of monomer mixture (with same proportions as above) was added uniformly over 90 minutes with rate of approximately 2.43 g/min. After the addition another portion of APS (3.1 g of 3 wt. % solution) was added and the reaction was continued for another 2 hours. The product was cooled in cold water with stirring. After filtration, the microgels were dialysed in DI water for 14 days (DI water was changed twice a day).

Method 2—Preparation of Poly(EA/MAA/BDDA) Microgel Particles

Poly(EA/MAA/BDDA) microgel was prepared using the seed-feed (starved feed) emulsion polymerisation method. A monomer mixture containing EA (Aldrich, 99%, 143.5 g), MAA (Aldrich, 99%, 72.0 g) and BDDA (Aldrich, 98%, 2.2 g) was prepared and 12.5% of the mixture added to a pre-purged, stirred, solution of sodium dodecylsulfate (BDH, 1.75 g in 500 g of water) which had been heated to 80° C. The monomers were passed over an alumina column prior to use to remove the inhibitor. $K_2HPO_4$ (3 g of 7% solution in water) and 2.95 g of a 5% ammonium persulfate solution in water were immediately added whilst maintaining a nitrogen atmosphere. After appearance of a slight blue turbidity, the remaining monomer mixture was added at a continuous rate over a 90 min period. Additional ammonium persulfate (3.3 g of 5% solution in water) was added and the temperature maintained at 80° C. for a further 2 h. The microgel was extensively dialysed against Milli-Q quality water.

Method 2A—Preparation of Poly(EA/MAA/BDDA) Microgel Particles

The poly(MMA/MAA/BDDA) microgel was also prepared using a similar method to Method 1A. However, MMA and EGD were replaced by EA and BDD, respectively, at the same mol. %.

Method 3—GMA Functionalisation of Poly(MMA/MAA/EGDMA) Microgel

Before glycidyl methacrylate (GMA, purum, ≥97.0% (GC)) functionalisation, poly(MMA/MAA/EGDMA) microgel [Method 1] was purified extensively by dialysis with changing the deionised water twice a day for at least two weeks. The purified microgel dispersions was mixed with GMA. This was done at a concentration of 5 times of GMA to the carboxylate concentration present in the microgel. The mixtures were diluted with DI water to microgel concentration 14.87 wt %, and the pH value was adjusted to 3.5 by adding aqueous HCl solution. The system was reacted at 50° C. in a water bath by stirring for 8 h. The reaction mixture was washed by ethyl acetate 4 times to remove most of unreacted GMA, and further dialyzed 3 days to remove any unreacted GMA completely.

Method 3A—GMA Functionalisation of Poly(MMA/MAA/EGDMA) and Poly(EA/MAA/BDDA) Microgel GM-M-EGD and GM-E-BDD refer to the GM-functionalised M-EGD and E-BDD microgels, respectively. The method used for functionalisation of M-EGD is briefly described in the following. The pH of a M-EGD dispersion with a polymer volume fraction ($\Box p$) of 0.15 containing 1.73 M of GM was adjusted to 3.5, and then heated to 50° C. with mechanical stirring for 8 h. The dispersion was washed four times with ethyl acetate and dialysed extensively to obtain the purified GM-M-EGD. A similar procedure was used to prepare GM-E-BDD particles. However, in that case the pH was 5.1 during functionalisation and the particles were washed with chloroform prior to dialysis. A pH of 5.1 was also used for the preparation of a more highly functionalised GM-M-EGD microgel, which is abbreviated here as GM(H)-M-EGD.

Method 3B—AEMHCL Functionalisation of Poly(MMA/MAA/EGDMA) and Poly(EA/MAA/BDDA) Microgel A typical preparation is described as follows for the preparation of AEM-functionalised M-EGD with a [AEM]/[MAA] ratio of 0.40, i.e., AEM40-M-EGD. The concentration ratio of MAA:EDC:NHS:AEM was 1:0.5:0.4:0.4. EDC and NHS are N-(3-dimethylaminopropyl)-N'-ethylcarbodiimide hydrochloride and N-hydroxysuccinimide, respectively. 10.25 g of 29 wt % M-EGD was placed in a 100 ml round bottom flask with magnetic stirrer and diluted by 30 ml of pH=6.6 buffer (0.1 M). Then 0.53 g of NHS was dissolved in 5 ml of buffer, 0.88 g of EDC was dissolved in 5.25 ml of 1M HCl. The solution containing NHS and EDC was then added to the microgel dispersion and allowed to stir for 20 min. Then, 0.76 g of aminoethyl methacrylate hydrochloride (AEMHCl) was dissolved in 5 ml of buffer and added. The final pH was adjusted to 6.5 by further buffer addition. The reaction was allowed to proceed for 1 day at RT. The product was purified by repeated centrifugation and re-dispersion in Milli-Q grade water. The partially aggregated state of the microgels facilitated centrifugation using a conventional high speed centrifuge.

AEM-E-BDD functionalised microgels were prepared in substantially the same manne, except that the pH was adjusted to about 7.0.

Method 4—Calculation of the Mol. % of GMA Grafted on to Poly(MMA/MAA/EGDMA) Microgel Particles in Method 3

These data were obtained by titration of the free carboxylic acid groups on the microgel particles and calculation of the mol. % of those groups reacted. Comparison with the composition of the microgel (Microgel 2B) enabled calculation of the mol. % of GMA incorporated. The results are shown in Table 1 below (see Method 6).

Method 4A—Calculation of the Mol. % of GMA Grafted on to Poly(MMA/MAA/EGDMA) and Poly(EA/MAA/BDDA) Microgel Particles in Method 3A As in Method 4 above, these data were obtained by potentiometric titration. The mol % GMA was determined from the difference in the mol % MAA in the microgel before and after functionalisation. The results are shown in Table A below.

TABLE A

| Code | Mol. % MAA[a] | Mol. % GMA[a] |
| --- | --- | --- |
| M-EGD | 35.9 | — |
| E-BDD | 37.2 | — |
| GM-M-EGD | 34.1 | 1.8 |
| GM(H)-M-EGD | 35.9 | 5.8 |
| GM-E-BDD | 26.5 | 7.8 |

[a]Determined from potentiometric titration data. The mol. % GMA was determined from the difference in the mol. % MAA in the microgel before and after functionalisation.

Method 4B—Calculation of the Mol. % of AEMHCl Grafted on to Poly(MMA/MAA/EGDMA) and Poly(EA/MAA/BDDA) Microgel Particles in Method 3B As per Method 4, these data were obtained by potentiometric titration. The mol % AEMHCL was determined from the difference in the mol % MAA in the microgel before and after functionalisation. The results are shown in Table A below.

TABLE B

| Code | [AEM]/[MAA][a] | Mol. % MAA (exp)[b] | Mol. % AEM (exp)[c] |
| --- | --- | --- | --- |
| M-EGD | — | 42.5 | — |
| AEM5-M-EGD[g] | 0.05 | 38.7 | 3.0 |
| AEM10-M-EGD | 0.10 | 38.5 | 4.1 |
| AEM20-M-EGD[g] | 0.20 | 34.3 | 7.4 |
| AEM30-M-EGD | 0.30 | 31.1 | 11.4 |
| AEM40-M-EGD | 0.40 | 35.1 | 7.4 |
| AEM50-M-EGD | 0.50 | 31.5 | 11.0 |
| E-BDD | — | 37.2 | — |
| AEM20-E-BDD | 0.20 | | |

[a]Concentration ratio of AEMHCl and MAA used to prepare the functionalised microgels.
[b]Mol. % MAA found in the microgels by titration.
[c]AEM contents determined from pH titration data for the microgels using the difference between the MAA contents in the parent microgel and the respective AEM-functionalised microgel.

Potentiometric titration was used to determine the MAA content and the effective $pK_a$ values for all of the microgels studied. See Table B above. These data also enabled calculation of the mol. % of AEM within the functionalised microgels.

Figures 1, 5B:
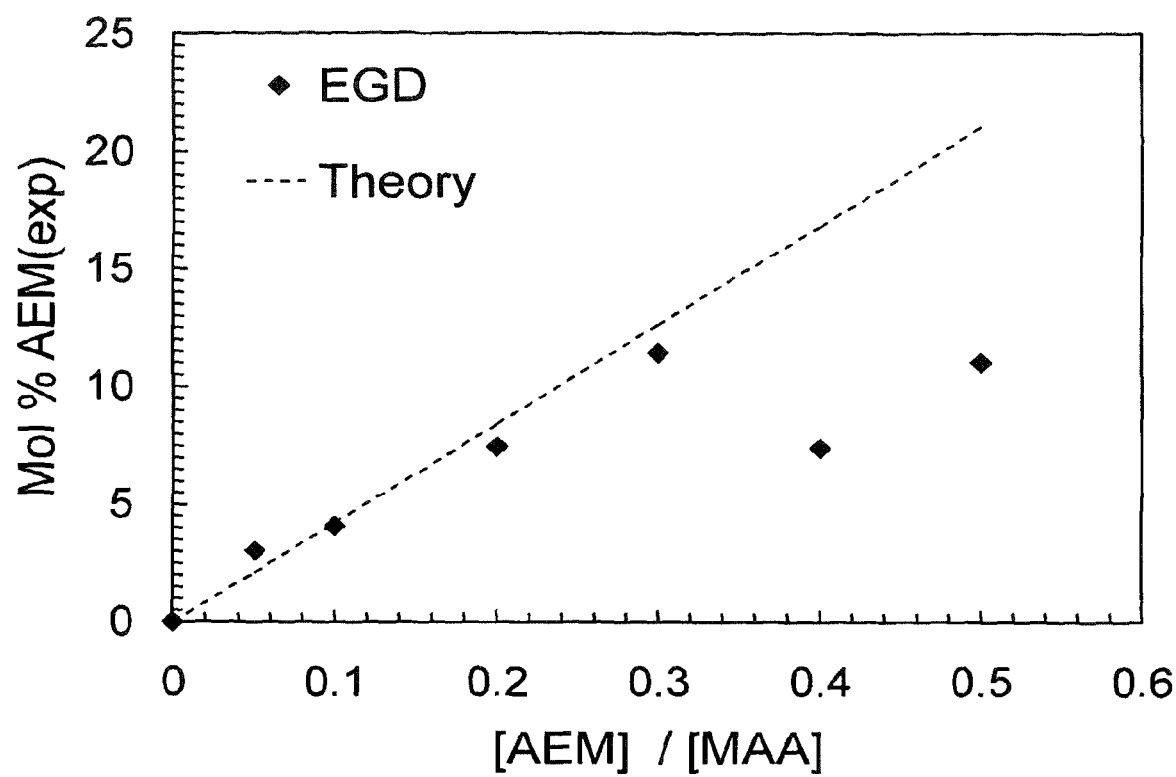
Figures 2, 5B:
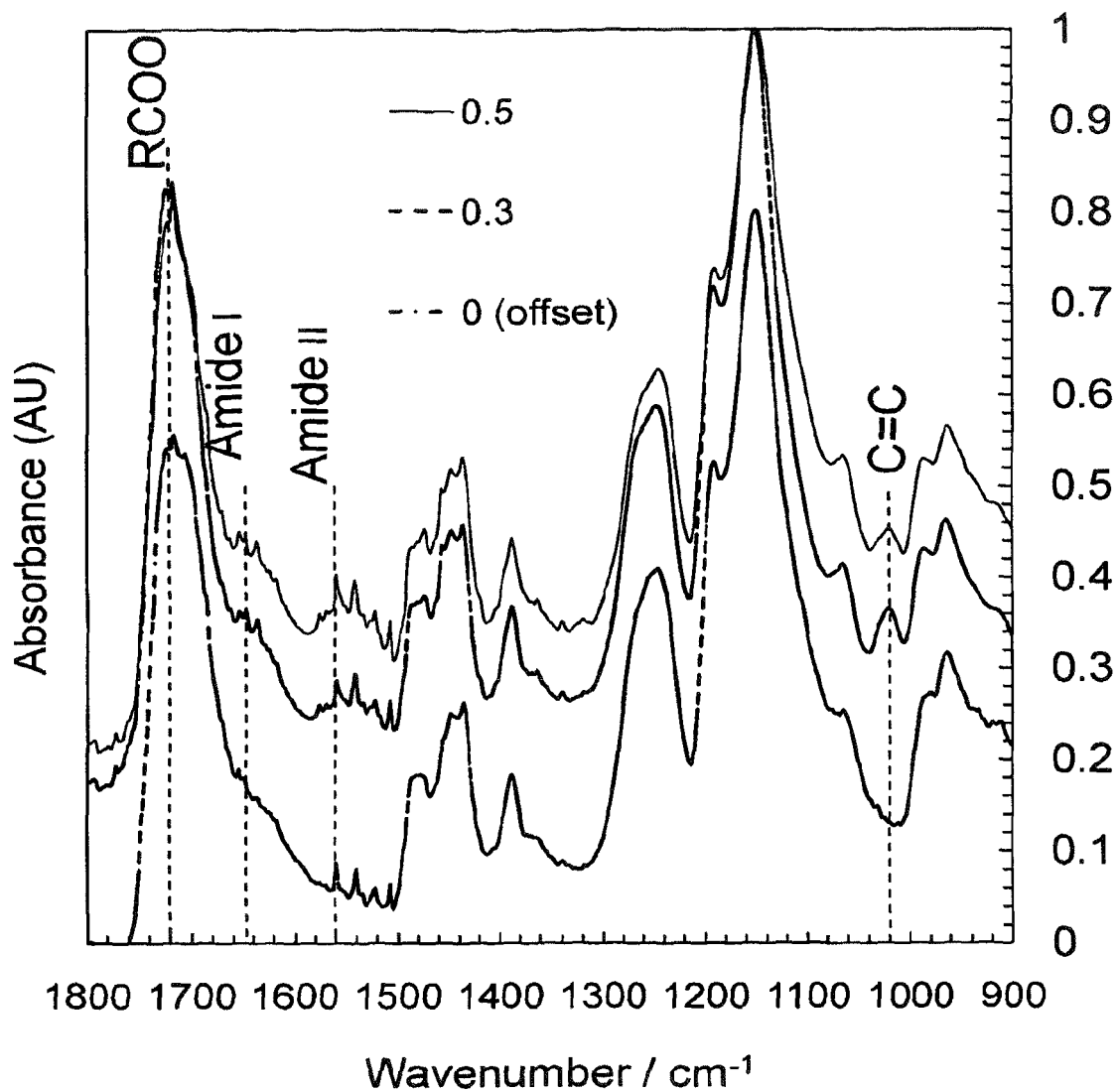
Figures 3, 5B:
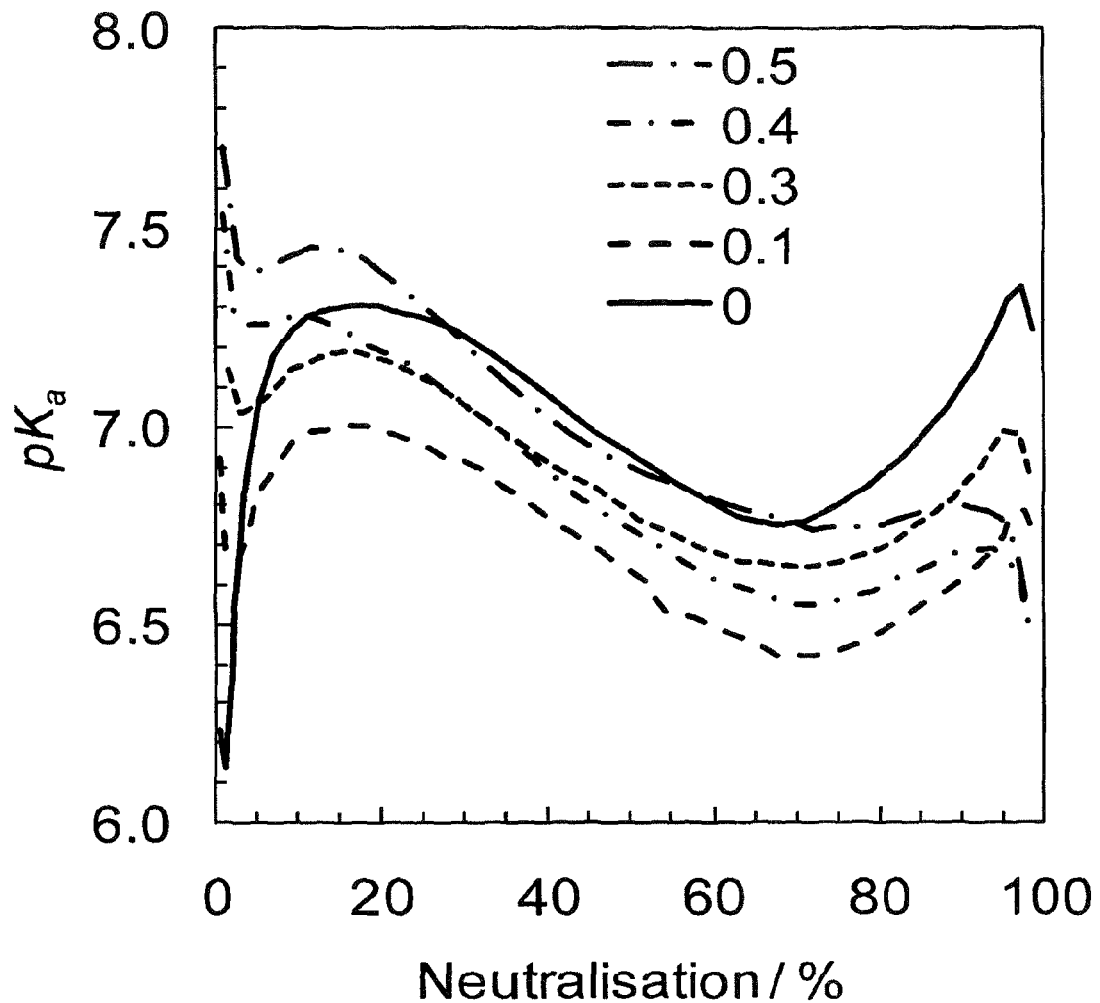

FIG. 5B-1 shows variation of Mol. AEM within the AEM-M-EGD microgels with [AEM]/[MAA]. The broken line represents the theoretical values for 100% efficiency of functionalisation.

It can be seen from FIG. 5B-1 that very good agreement between theory and experiment was observed until [AEM]/[MAA] exceeded 0.30. At higher [AEM]/[MAA] levels a much lower than expected incorporation occurred and the values became more variable. Interestingly, the maximum mol. % of AEM incorporated did not exceed the value determined at the end of the linear region (11.4 mol. %).

FTIR data were obtained for the functionalised microgels (FIG. 5B-2).

FIG. 5B-2 shows selected FTIR spectra for AEM-M-EGD microgels. The legend shows the [AEM]/[MAA] ratios used. The spectra were recorded on dry films and selected bands are labelled.

They show evidence of vinyl group incorporation from a band at 1020 cm$^{-1}$, which is present for the AEM-functionalised microgels but absent in the spectrum for M-EGD. The Amide I (1647 cm$^{-1}$) and Amide II (1560 cm$^{-1}$) bands[17] were also evident upon functionalisation. The spectra support our interpretation that vinyl functionalisation occurred successfully.

The pK$_a$ values for the microgels were calculated at each neutralisation point from the titration data using:

$$pK_a = pH - \log\left(\frac{\alpha}{1-\alpha}\right)$$

where α is the degree of neutralisation. We (and others) have established that as the MAA content in latex particles increases the pK$_a$ decreases. This has been attributed (Pinprayoon, O.; Groves, R.; Saunders, B. R. *J. Coll. Interf. Sci.* 2008, 321, 315) to a decrease in hydrophobic interactions which oppose particle swelling as a result of ionisation.

FIG. 5B-3 shows variation of pK$_a$ with neutralisation for AEM-M-EGD microgels. The legends give the [AEM]/[MAA] ratios used for their preparation. The data show a pronounced increase in the pK$_a$ values for α<20% with increasing [AEM]/[MAA]. This is a strong indication that functionalisation proceeds from the exterior of the microgel inwards. The AEM groups are relatively hydrophobic compared to MAA and this leads to an increase of the local pK$_a$. These data provide evidence of a locally high AEM functionalisation at the microgel periphery. This is consistent with the particles being partially swollen at the initial stages of the functionalisation process. It is likely that the peripheries of the particles close up as the functionalisation proceeds due to an increased hydrophobicity and loss of charge in that region. This would cut off supply of AEM to the inner regions of the microgels.

Method 5—pH-Dependent Particle Size Measurements for Microgels from Methods 1 and 2

The measurements were performed using photon correlation spectroscopy using a particle concentration in the range of 0.001 to 0.1 wt. % Standard buffer solutions were used for these experiments. These measurements were performed using a Brookhaven BI-9000 light scattering apparatus fitted with a 20 mW HeNe laser. The detector was set at a 90° scattering angle.

Figure 4:
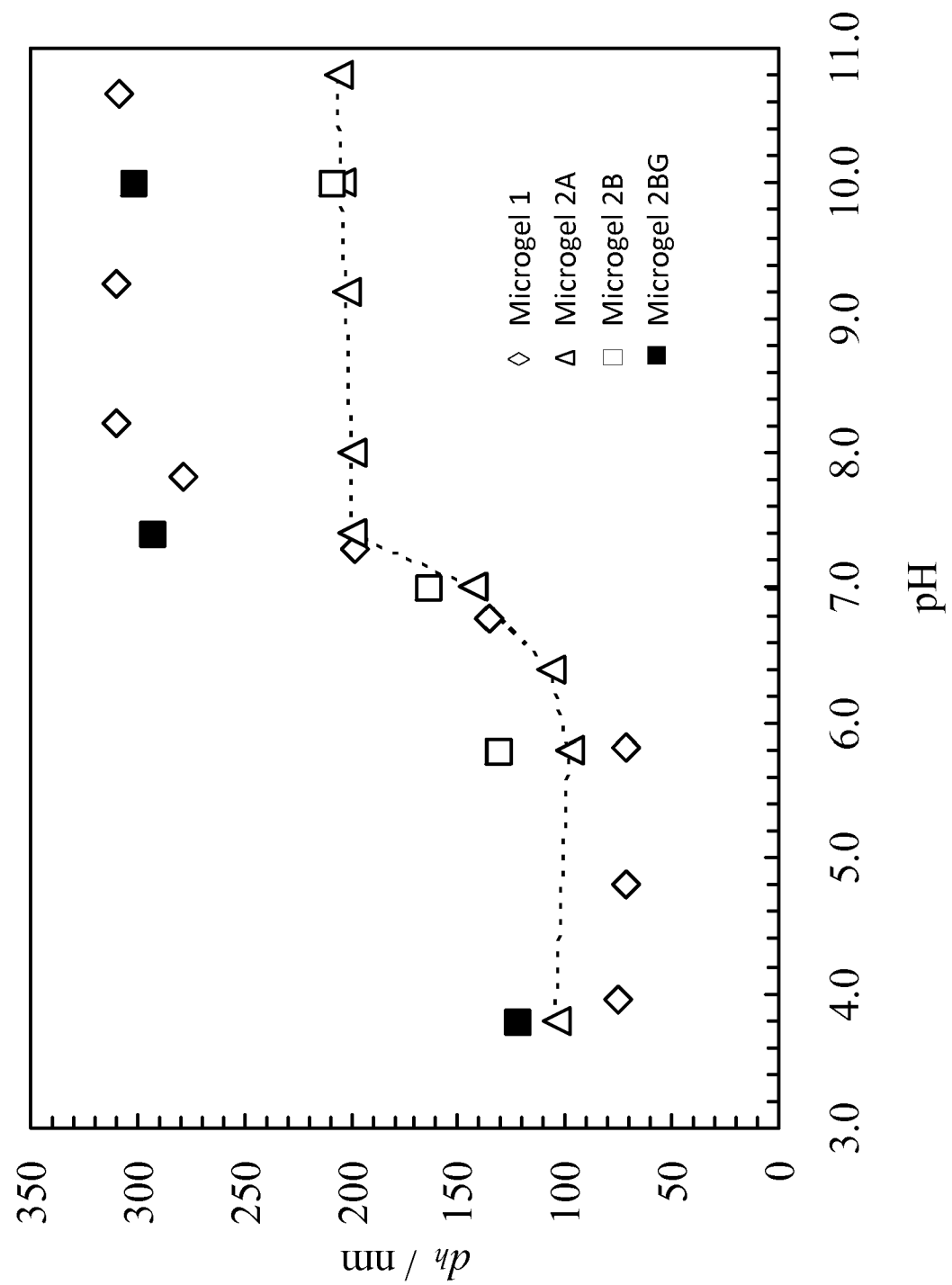
FIGS. 4 to 18 are described in the accompanying examples.

The results are shown in FIG. 4 [Microgel 1 (open diamonds), 2A (open triangles), 2B (open squares), 2BG (closed squares)].

Method 5A—pH-Dependent Particle Size Measurements for Microgels from Methods 1A, 2A and 3A The measurements were performed using photon correlation spectroscopy using dispersions containing $\phi_p=3\times10^{-4}$ microgel. Standard buffer solutions were used for these experiments. These measurements were performed using a Brookhaven BI-9000 light scattering apparatus fitted with a 20 mW HeNe laser. The detector was set at a 90° scattering angle.

Figure 4A:
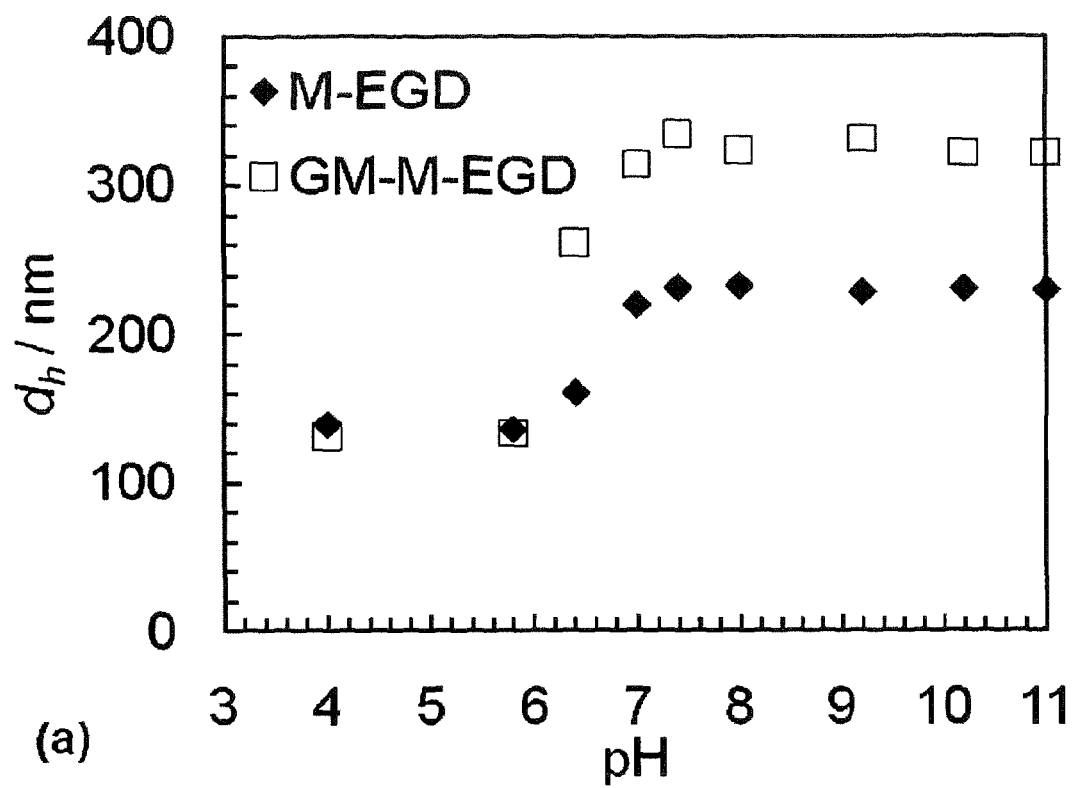
Figure 4A:
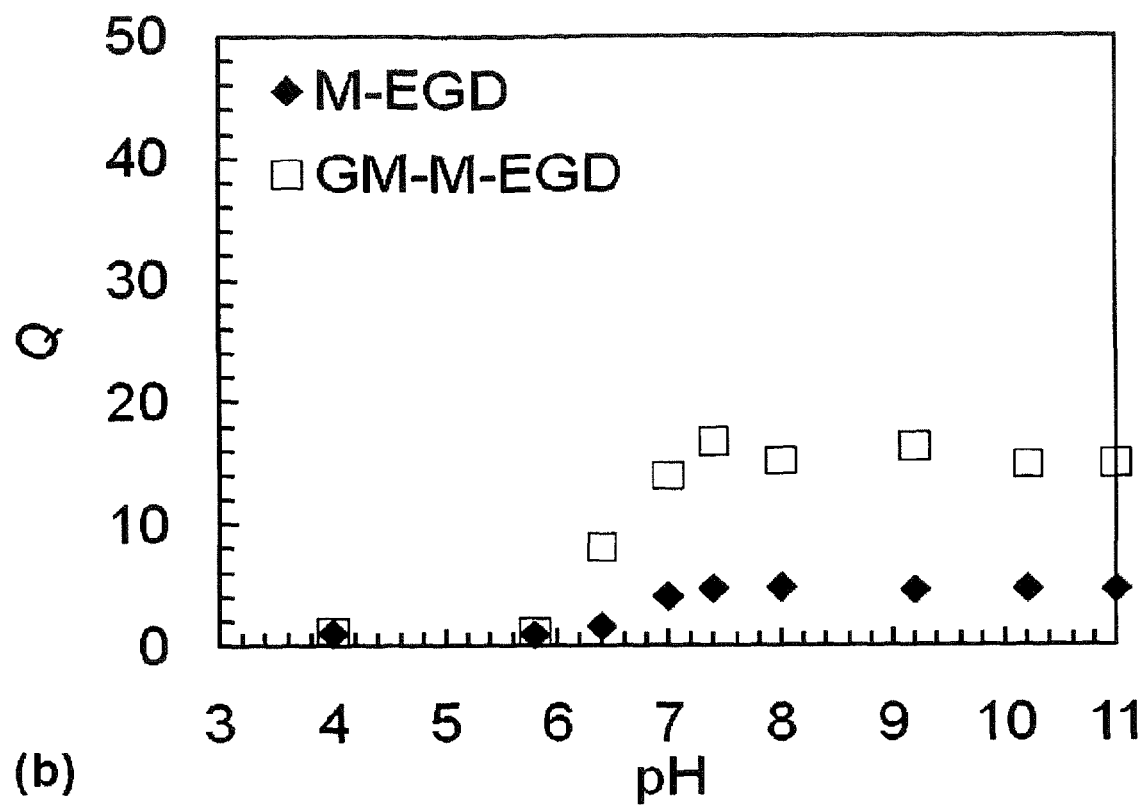
Figure 4A:
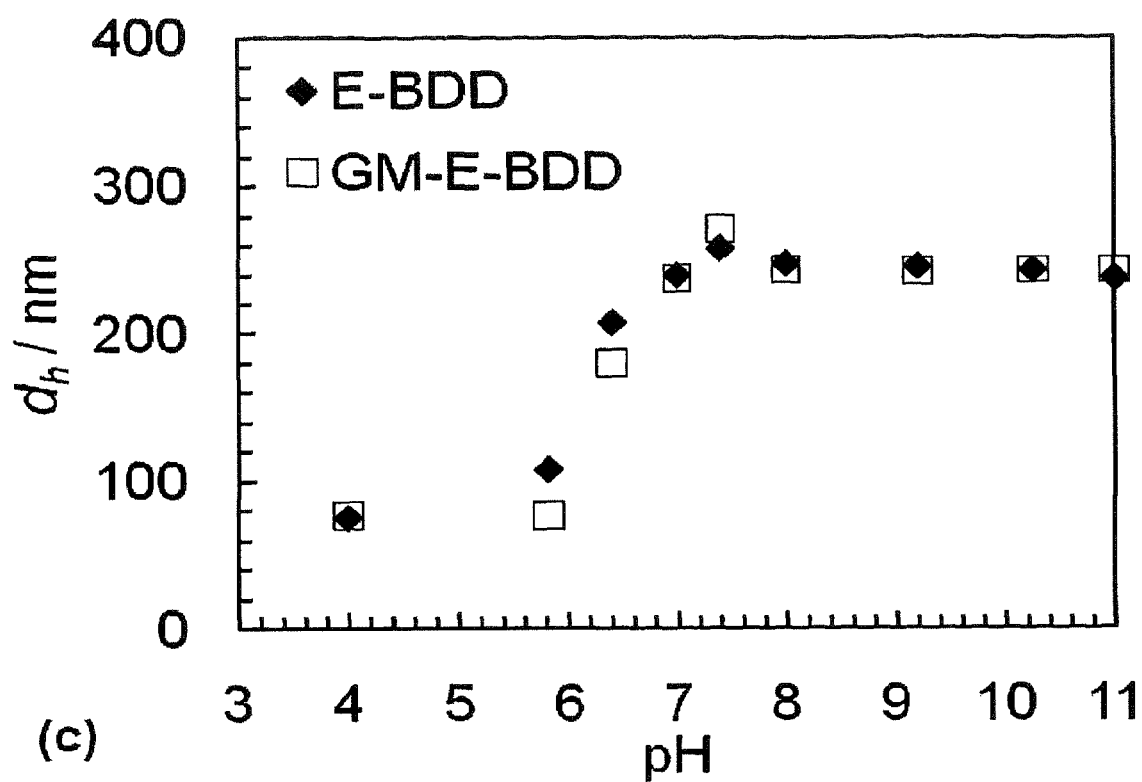
Figure 4A:
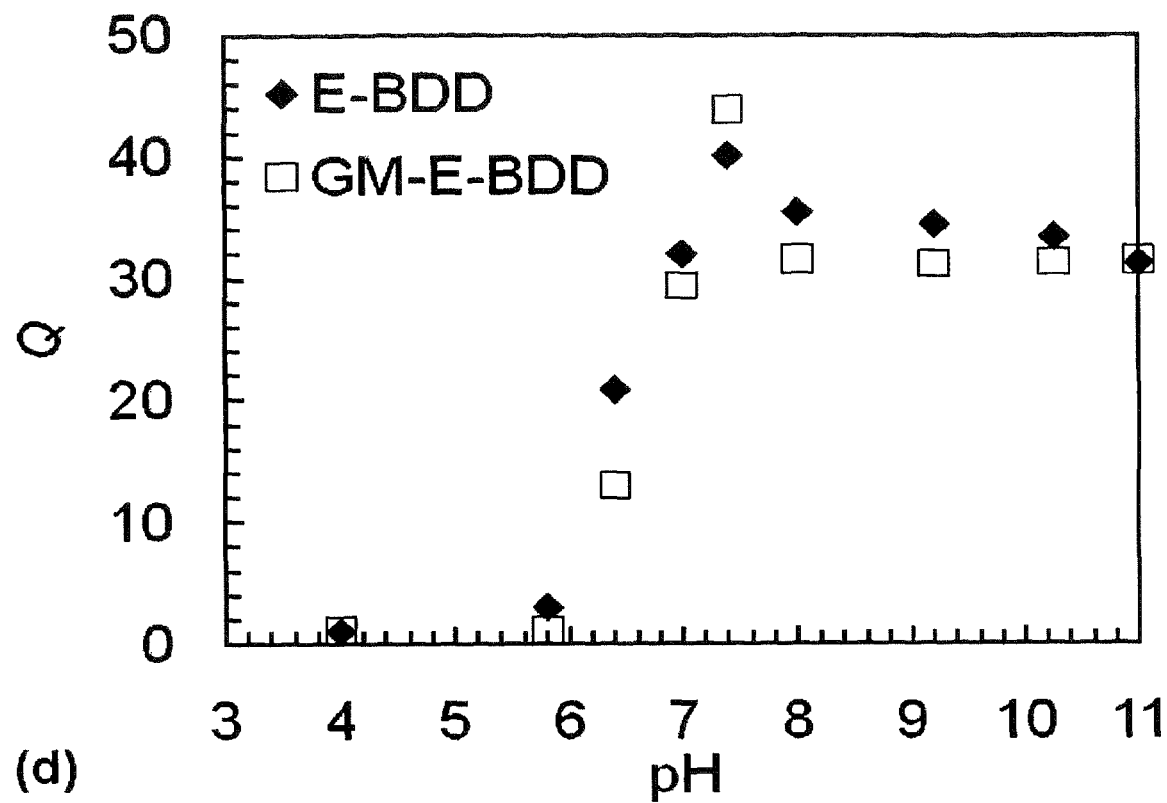
Figures 2, 4A:
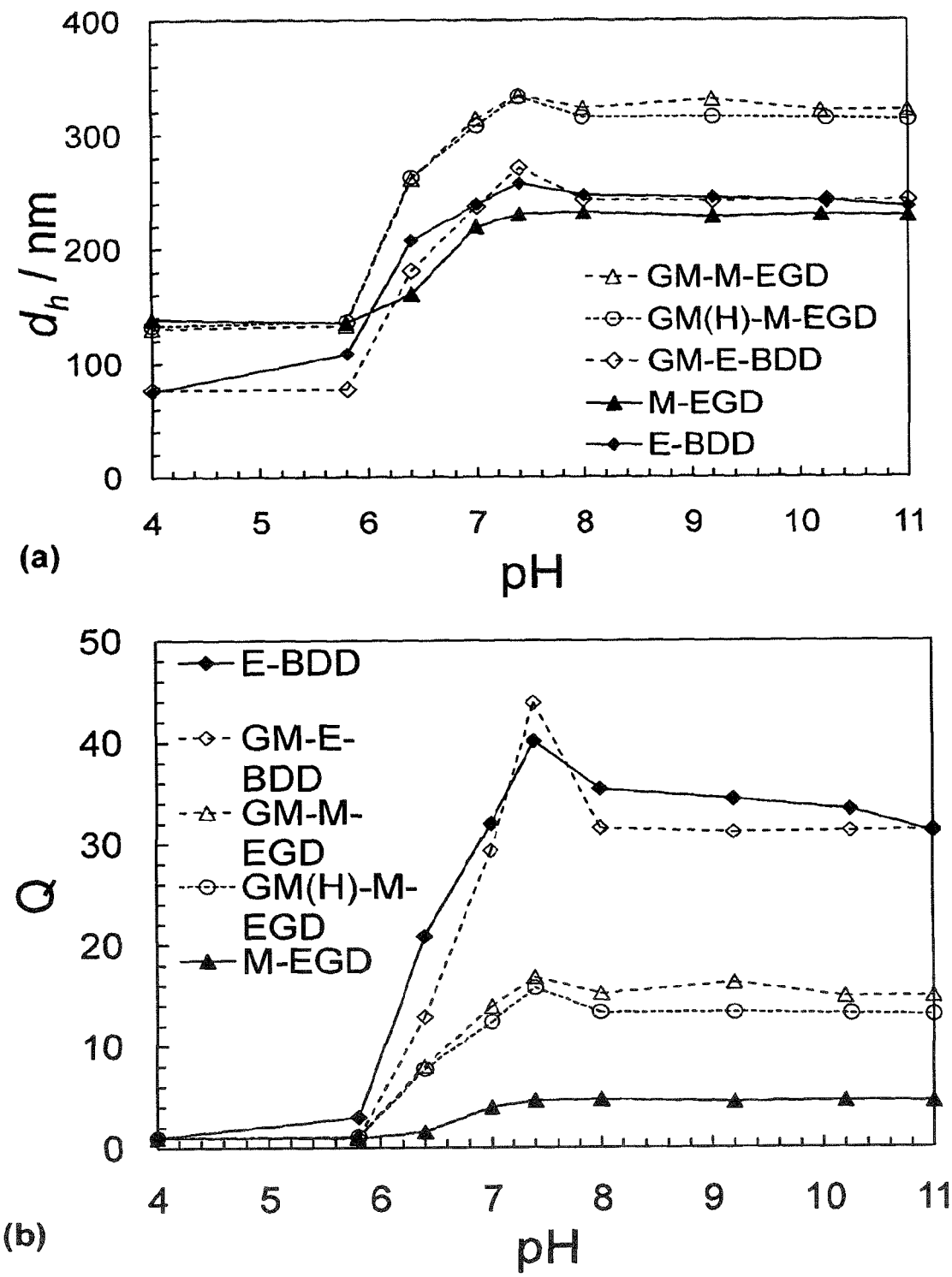

FIG. 4A shows the pH-dependence of the hydrodynamic diameter (d$_h$) and Q values for the microgels: a) and b) [M-EGD (solid diamonds), GM-M-ECD (open squares)]; c) and d) [E-BDD (solid diamonds), GM-E-BDD (open squares)], where GM- prefix refers to a GMA functionalized microgel.

Selected data are also shown in Table 1. The data show pH-triggered swelling at pH of about 6.4. Complete swelling had occurred by pH of about 7.4. The latter corresponds to the pK$_a$ of the microgel. It is noted that there is not perfect agreement between the pK$_a$ values and the particle swelling data (FIG. 4A). The pK$_a$ for polyelectrolyte gels is strongly affected by a number of factors, which includes polymer and electrolyte concentration[18]. Therefore, the differences between the pK$_a$ values and the pH range of strong swelling (FIG. 4A) can be attributed to differences in electrolyte concentration and polymer concentration within the microgel particles for each technique.

Interestingly, it can be seen from FIG. 4A that the GM-M-EGD microgels swell much more than the M-EGD particles. This was suspected to be due to the ethyl acetate washing procedure, which was used to remove residual GMA from the microgels. To test this idea non-functionalised microgel was washed with ethyl acetate. The particle size for M-EGD increased from to 285 nm at pH=8 after ethyl acetate washing (cf. 232 nm in Table 1). This is a new observation for pH-responsive MMA-based microgels and strongly indicates that reversible hydrophobic association restricts the swelling for these microgels. The washing process must remove physical crosslinks, presumably involving MMA groups. The presence of hydrophobic crosslinks could be aided by the low mobility of PMMA chains due to their high T$_g$. Ethyl acetate may act as a plasticiser for the M-EGD particles. In contrast the pH-dependent swelling for the E-BDD and GM-E-BDD microgels were almost identical (FIGS. 4A(b) and 4A(d)). This is probably because the E-BDD microgels is composed of polymer chains with a lower T$_g$ and is less affected by hydrophobic physical crosslinks. This is supported by the higher Q values obtained for the E-BDD microgels (FIG. 4A).

FIG. 4A-2 includes additional data showing the variation of (a) hydrodynamic diameter and (b) swelling ratio with pH for the various microgels, including the highly functionalized GM(H)-M-EGD microgel.

Method 5B—pH-Dependency and Other Dependencies of Particle Size Measurements for Microgels from Methods 1a, 2a and 3B The measurements were performed using photon correlation spectroscopy using dispersions containing $\phi_p=3\times10^{-4}$ microgel. Standard buffer solutions were used for these experiments. These measurements were performed using a Brookhaven BI-9000 light scattering apparatus fitted with a 20 mW HeNe laser. The detector was set at a 90° scattering angle.

Figures 1A, 4B:
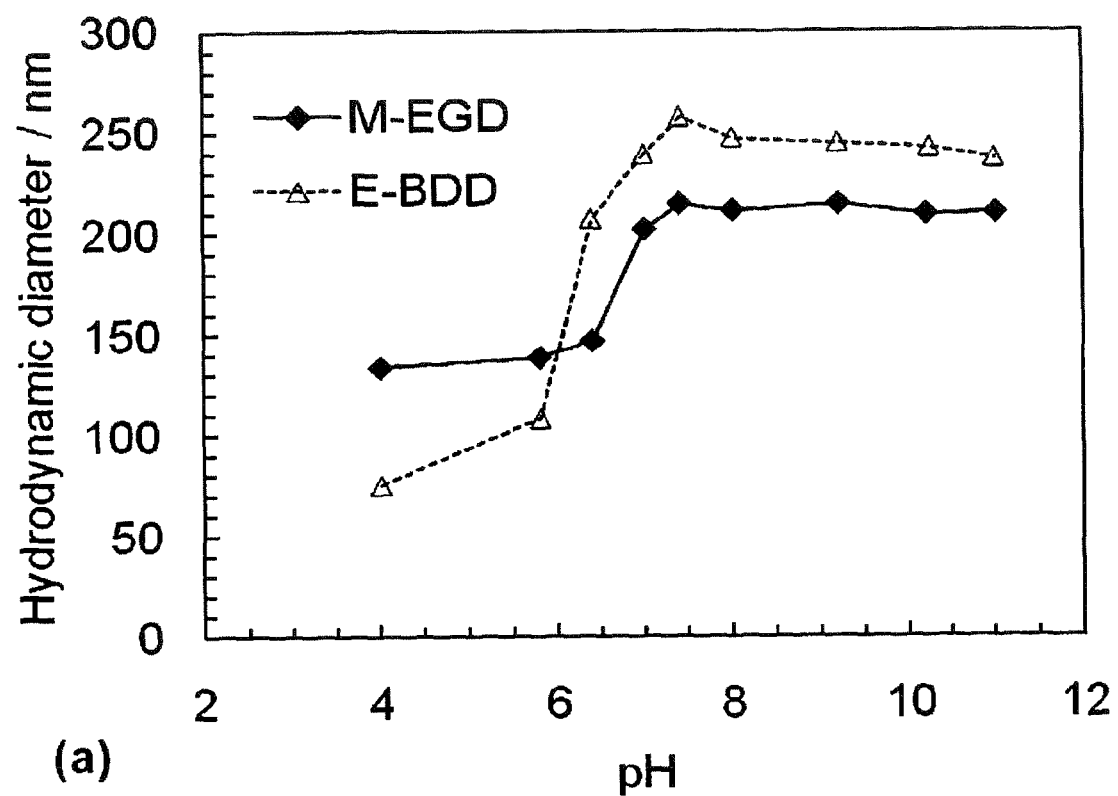
Figures 1B, 4B:
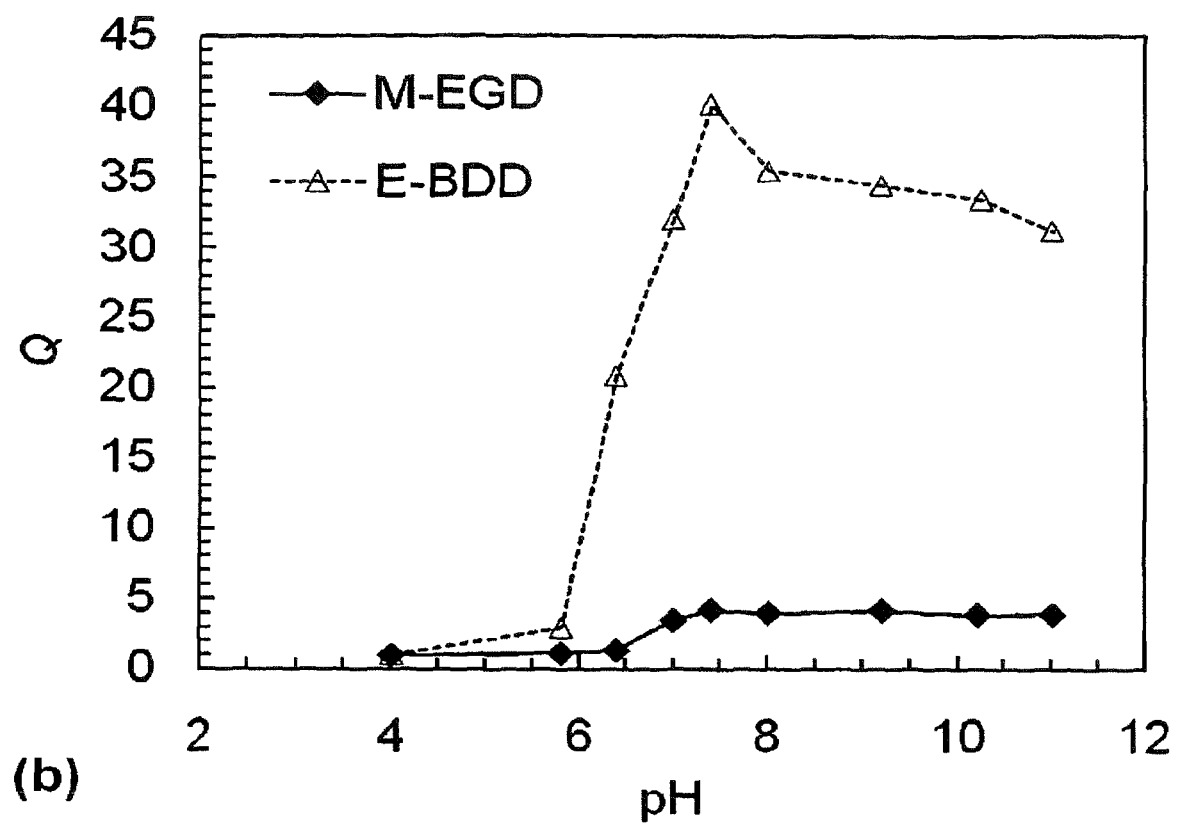

FIG. 4B-1 shows variation of (a) hydrodynamic diameter, (b) swelling ratio and (c) $\phi_p^*$ with pH for the M-EGD (solid diamonds) and E-BDD (open triangles) microgels. The data were measured using 0.1 M buffers.

The microgel particles swell when the pH approaches their respective pK$_a$ values. Using equation (1) the maximum values of Q for M-EGD and E-BDD are 4 and 40, respectively. The E-BDD microgel swell very strongly. The relatively low swelling for the M-EGD microgels is because they have a reversible crosslinking contribution which restricts swelling (Liu, R.; Milani, A. H.; Freemont, T. J.; Saunders, B. R. *Manuscript submitted to Soft Matter* 2011). The swelling can be increased greatly for the M-EGD microgels using ethylacetate washing.

The polymer volume fraction at which neighbouring microgel particles overlap, $\phi_p^*$, because gives an indication of when inter-particle crosslinking may be effective. Also, it will be related to the point at which physical gelation occurs. In recent work (Lally, S.; Cellesi, F.; Freemont, T.; Saunders, B. R. *Coll. Polym. Sci.* 2011, In Press) we found that $\phi_p^*$ could be estimated for E-BDD microgel dispersions as the value of $\phi_p$ which is equal to the internal polymer volume fraction within the (swollen) microgel particles ($\phi_{MG}$). Our approach for microgels draws upon the definition of polymer overlap concentrations for polymer micelles (van Ruymbeke, E.; Pamvouxoglou, A.; Vlassopoulos, D.; Petekidis, G.; Mountrichas, G.; Pispas, S. *Soft Matter* 2010, 6, 881). It assumes that the radial segment distribution within each particle is constant and ignores interstitial voids between the particles, i.e. assumes a packing efficiency of 100%. For hard sphere microgel particles a packing efficiency of less than 100% is expected[3]. However, the precise packing efficiency will be dependent on microgel composition and is not able to be pre-determined. The following equation was used to estimate $\phi_p^*$.

$$\phi_p^* = \frac{1}{Q} \quad (3)$$

Figures 1C, 4B:
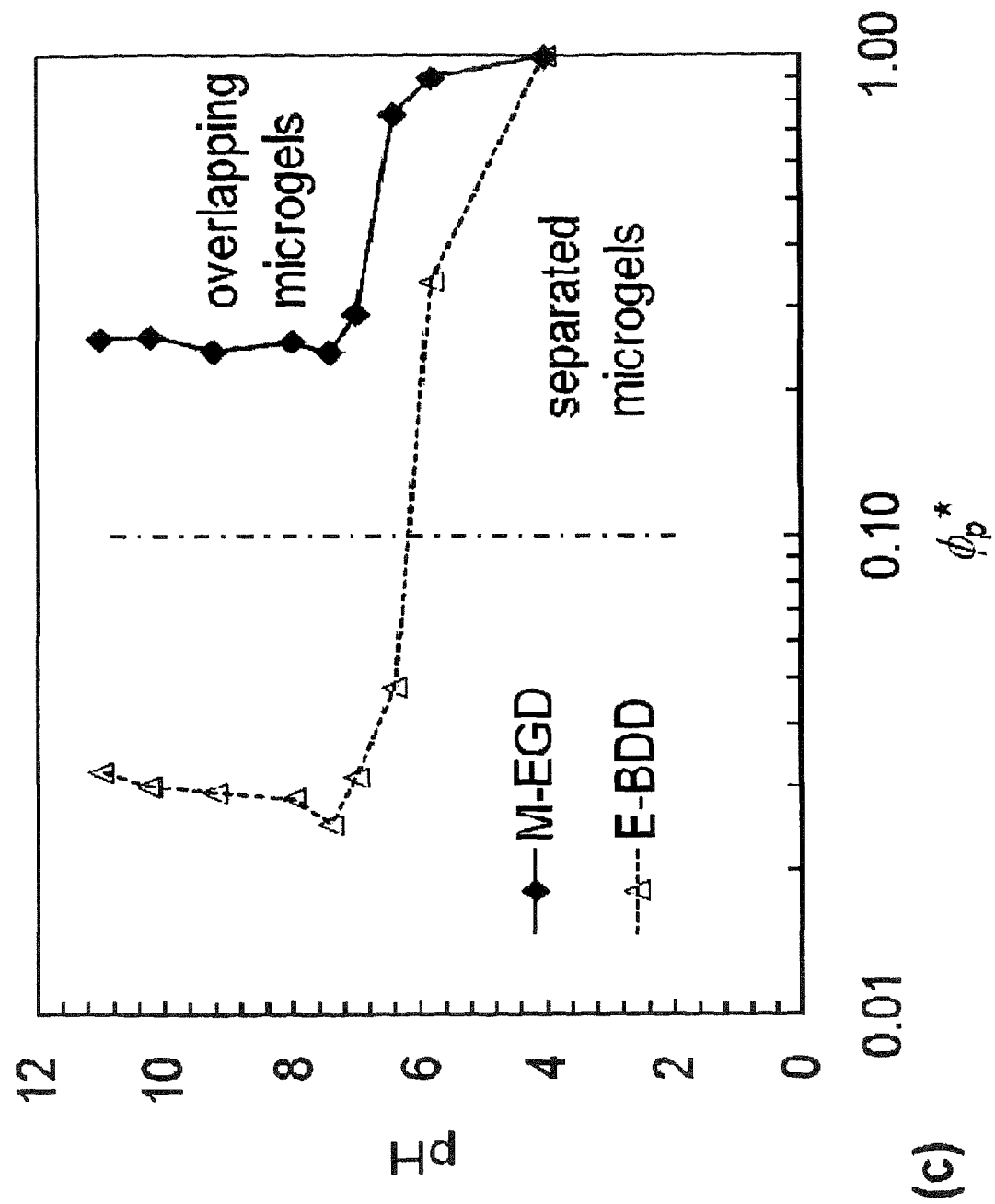
Figures 2, 4B:
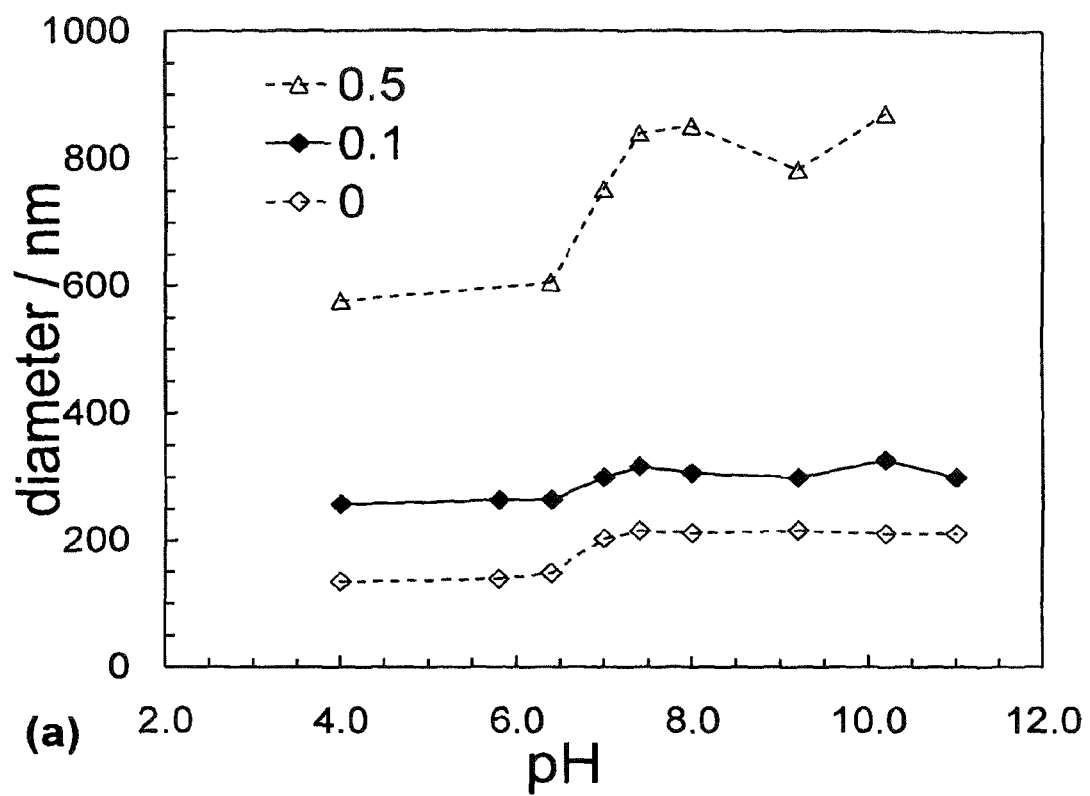
Figures 2, 4B:
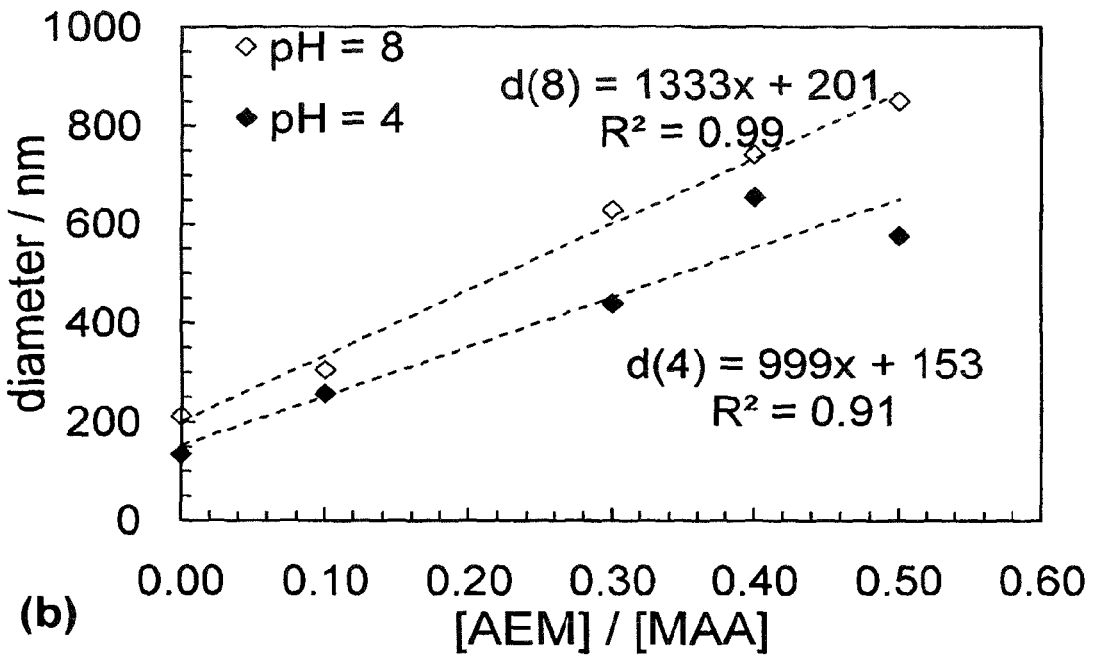
Figures 2, 4B:
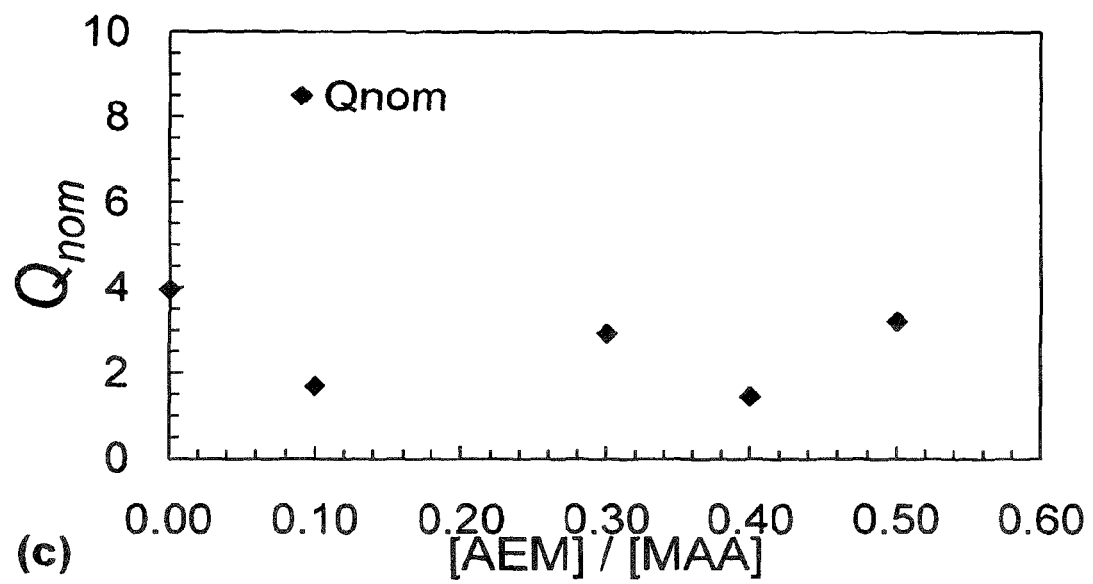
Figures 3, 4B:
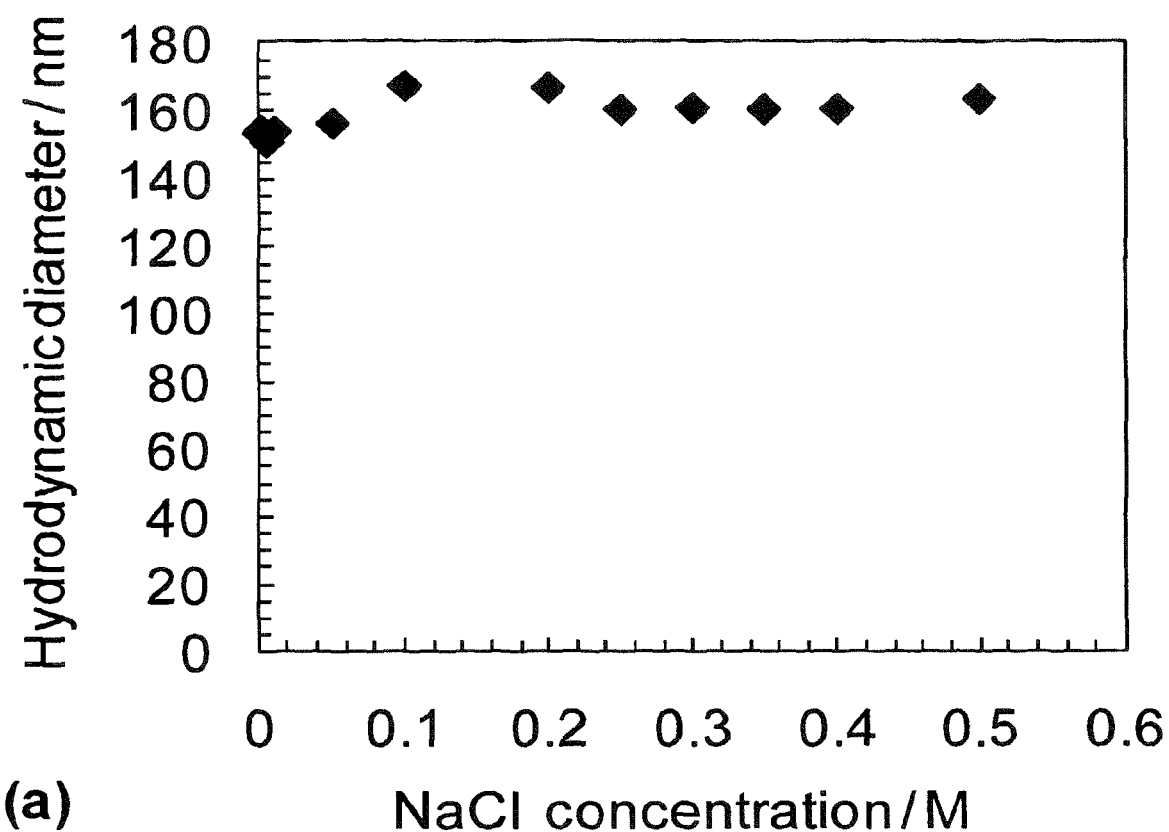
Figures 3, 4B:
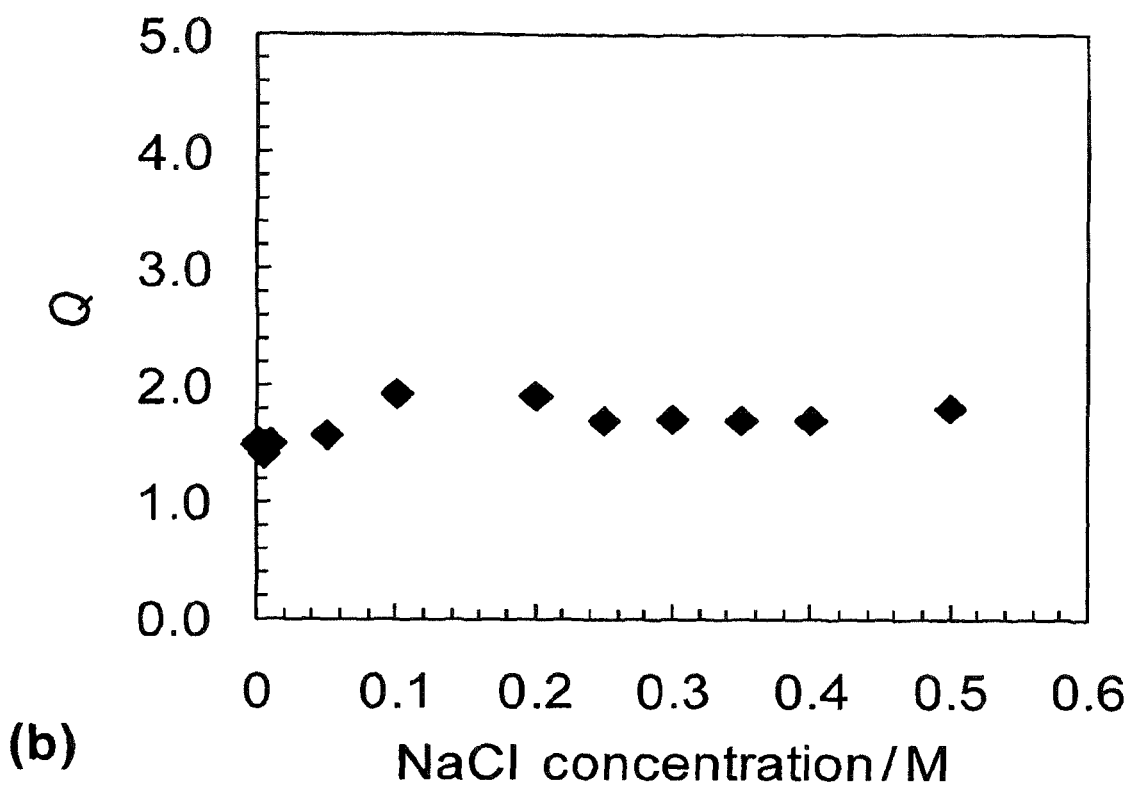

Data for $\phi_p^*$ are shown in FIG. 4B-1(c). These data can be used to infer overlap and also gel elasticity. It is expected that overlap and elasticity will be highest for the E-BDD physical gels if $\phi_p$ value of 0.10 is used and the pH is greater than 6.5.

FIG. 4B-2 shows variation of (a) hydrodynamic diameter with pH, (b) diameter with [AEM]/[MAA] ratio and (c) nominal Q with [AEM]/[MAA] for the AEM-M-EGD microgels. The data point in (b) for [AEM]/[MAA]=0.30 and labelled as pH=8 was measured at pH=7.4. The data in (a) are for AEMHCL-M-EGD microgels formed using an [AEM]/[MAA] concentration ratio of 0.5 (open triangles), 0.1 (solid diamonds), 0 (open diamonds)], where an AEM-HCL-prefix refers to an AEMHCL functionalised microgel.

PCS was used to measure the size of the collapsed particles (pH=4) after functionalisation. The data are shown in FIGS. 4B-2(a) and (b) Swelling ratio data are shown in FIG. 4B-2(c), where the term $Q_{nom}$ has been used for Q.

The data show a linear increase in diameter with [AEM]/[MAA] ratio for all of the M-EGD microgels studied at pH=4 and 8. This is attributed to aggregation. Nominal Q values at pH=8 were calculated using equation (1) and are shown in FIG. 4B-1(c). These values, which are subject to considerable scatter, are based on the assumption that the aggregates are irreversibly formed during the vinyl functionalisation stage and do not break down when the pH is increased. The fact that $Q_{nom}$ does not change significantly with [AEM]/[MAA] indicates that the swelling of the individual particles has not been greatly affected by AEM functionalisation. That is they have maintained their pH-responsiveness, even in the aggregated state. See also FIG. 4B-1(a). This is reasonable given that the maximum extent of functionalisation affects about ⅓ rd of the MAA groups present in the parent microgel (Table 1).

In contrast to an earlier vinyl-functionalisation method (Example 3A) involving GMA (glycidyl methacrylate) the method used here involved a high electrolyte concentration. This is because of the use of AEMHCl. The pH used in this method was ca. 6.6, which required addition of buffer and NaOH. This pH was used to ensure the microgel particles were at least partially swollen during functionalisation. AEMHCl is an electrolyte and so high ionic strengths were present.

FIG. 4B-3 shows variation of (a) hydrodynamic diameter and (b) swelling ratio (Q) with concentration of NaCl in solution at pH=6.6 for M-EGD microgel dispersion.

The effect of added NaCl on the particle size of the microgel was investigated at pH=6.6 (FIG. 4B-3). At this pH the particles were slightly swollen (Q=1.5). A slight increase in size occurred (to ca. 170 nm, FIG. 3S) at a NaCl concentration of 0.10 M indicating some slight aggregation. These data show that functionalisation occurred under conditions where the particles were (initially) slightly swollen and that limited (partial) aggregation occurred. The extent of aggregation will depend on the extent of particle swelling (and hence pH). For comparison, functionalisation using [AEM]/[MAA]=0.40 involved addition of reactants and buffer that gave an ionic strength contribution of 0.28 M. An additional contribution from the microgel particles (MAA groups) themselves would have increased the ionic strength. Therefore, it is not surprising that partial aggregation occurred during the functionalisation process. The data from FIG. 4B-2 show this became progressively more pronounced with increasing [AEM]/[MAA]. It is important to note that the aggregate sizes from FIG. 4B-2 are all less than 1 μm. This means that these dispersions would still able to be injected through narrow gauge syringe needles. This is important for future potential applications involving minimally invasive techniques (e.g., injection).

Method 6—Characterisation of the Microgel Particles Prepared in Methods 1, 1A, 2, 2A, 2B, 3, 3A, and 3B The characterisation data is presented in Table 1 below:

TABLE 1

| No. | Method | Composition[a] | $d_{h(4)}$/nm[b] | $d_{h(10)}$/nm[b] | q[c] | $pK_a$ |
|---|---|---|---|---|---|---|
| 1 | 2 | poly($EA_{66}$/$MAA_{33}$/$BDDA_{1.0}$) | 75 | 309 | 70 | 6.70 |
| 2A | 1 | poly($MMA_{66}$/$MAA_{33}$/$EGDMA_{1.0}$)[d] | 104 | 205 | 7.7 | |
| 2B | 1 | poly($MMA_{66}$/$MAA_{33}$/$EGDMA_{1.0}$) | 130 | 208 | 4.1 | 6.35 |
| 2BG | 3 | poly($MMA_{66}$/$MAA_{23}$/$EGDMA_{1.0}$)-$GMA_{0.018}$ | 131 | 323[g] | 15[h] | 7.1 |
| 3[e] | 1 | poly($MMA_{66}$/$MAA_{33}$/$PEGDMA550_{1.0}$) | 150 | | | |
| 3G[e] | 3 | poly($MMA_{66}$/$MAA_{33}$/$PEGDMA550_{1.0}$)-GMA[f] | | | | |
| M-EGD | 1A | poly($MMA_{66}$/$MAA_{33}$/$EGDMA_{1.0}$) | 139 | 230 | 4.7[h] | 7.4 |
| E-BDD | 2A | poly($EA_{66}$/$MAA_{33}$/$BDDA_{1.0}$) | 75 | 247[g] | 35[h] | 6.5 |
| GM-M-EGD | 3A | poly($MMA_{66}$/$MAA_{33}$/$EGDMA_{1.0}$)-$GMA_{0.018}$ | 131 | 323[g] | 15[h] | 7.1 |
| GM(H)-M-EGD | 1A | poly($MMA_{66}$/$MAA_{33}$/$EGDMA_{1.0}$)-$GMA_{0.058}$ | 133 | 315 | 13 | 6.0 |

TABLE 1-continued

| No. | Method | Composition[a] | $d_{h(4)}$/nm[b] | $d_{h(10)}$/nm[b] | q[c] | $pK_a$ |
|---|---|---|---|---|---|---|
| GM-E-BDD | 3A | poly($EA_{66}$/$MAA_{33}$/$BDDA_{1.0}$)-$GMA_{0.078}$ | 77 | 243[g] | 32[h] | 6.1 |
| M-EGD | 1A | poly($MMA_{66}$/$MAA_{33}$/$EGDMA_{1.0}$) | 134 | 212[g] | | 7.2 |
| AEM5-M-EGD | 3B | poly($MMA_{66}$/$MAA_{33}$/$EGDMA_{1.0}$)-$AEM_{0.030}$ | — | — | | 6.5 |
| AEM10-M-EGD | 3B | poly($MMA_{66}$/$MAA_{33}$/$EGDMA_{1.0}$)-$AEM_{0.041}$ | 257 | 306[g] | | 6.6 |
| AEM20-M-EGD | 3B | poly($MMA_{66}$/$MAA_{33}$/$EGDMA_{1.0}$)-$AEM_{0.074}$ | — | — | | 6.7 |
| AEM30-M-EGD | 3B | poly($MMA_{66}$/$MAA_{33}$/$EGDMA_{1.0}$)-$AEM_{0.114}$ | 653 | 914[g] | | 6.8 |
| AEM40-M-EGD | 3B | poly($MMA_{66}$/$MAA_{33}$/$EGDMA_{1.0}$)-$AEM_{0.074}$ | 655 | 742[g] | | 6.7 |
| AEM50-M-EGD | 3B | poly($MMA_{66}$/$MAA_{33}$/$EGDMA_{1.0}$)-$AEM_{0.11}$ | 576 | 851[g] | | 6.9 |
| AEM20-E-BDD | 3B | poly($MMA_{66}$/$MAA_{33}$/$EGDMA_{1.0}$)-AEM | | | | |
| μ-BDD | 2 | poly($EA_{66}$/$MAA_{33}$/$BDDA_{1.0}$) | 108 | 310[i] | 24[j] | 6.7 |

[a]The numbers in the subscripts are the approximate nominal compositions (wt. %) based on the preparation conditions. In the case of GMA or AEM the number is based on titration data and refers to the composition as a whole (See Example 10).
[b]Hydrodynamic diameter measured at pH = 4 or 10.
[c]Volumetric swelling ratio calculated using $d_{h(10)}$ and $d_{h(4)}$ values according to: $q = (d_{h(10)}/d_{h(4)})^3$.
[d]This microgel was prepared using high shear.
[e]3 and 3G were made using methods 1 and 3, respectively, The difference is that PEGDMA550 was used instead of EGDMA. The wt. % concentration was the same.
[f]The composition of 3G should be similar to that of Microgel 2BG, but has not been established at the present time.
[g]In these cases, the hydrodynamic diameter was measured at pH 8, not 10.
[h]In these cases, volumetric swelling ratios are calculated using $d_{h(8)}$ and $d_{h(4)}$ values according to: $q = (d_{h(8)}/d_{h(4)})^3$.
[i]In these cases, the hydrodynamic diameter was measured at pH 7, not 10.
[j]In these cases, volumetric swelling ratios are calculated using $d_{h(7)}$ and $d_{h(4)}$ values according to: $q = (d_{h(7)}/d_{h(4)})^3$.
The extent of functionalisation by GMA for GM-M-EGD (from method 3A) was modest (1.8 mol. % overall, or 5% of the MAA groups). As will be shown below this was sufficient to form DX gels. In the case of the GM-E-BDD (from method 3A) the functionalisation was much higher (7.8 mol. % overall, or 21% of the MAA groups). To prepare colloidally stable GM-E-BDD microgel dispersions it was necessary to use a higher pH for the functionalisation to avoid aggregation during the process. The relatively high GMA content for the GM-E-BDD microgels did not decrease the extent of swelling as judged by the Q values at pH = 8 (Table 1).

Example 1—Cross-Linking of Microgel Particles by Formation of an Interpenetrating Polymer Network Two Methods were Used:

Method A:

In this method the microgel was added first. Typically, the system was prepared using 10 wt. % microgel (methods 1 or 2) and 10 wt. % PEGDMA550 stock dispersion. In that case a mixture of 0.2 ml of ammonium persulfate solution (10 wt. % in water), 0.5 ml of aqueous 2 M NaOH was added to a mixture of 2.5 ml of microgel (16 wt. %), 0.36 ml of PEGDMA550 and 0.44 ml of DI water using stirring. The final weak gel like mixture was held in a water bath and allowed to react at the desired temperature.

Method B:

Cross-linker added first. In this case 2.5 ml of microgel (16 wt. %) was added to a pre-prepared mixture of 0.2 ml of ammonium persulfate solution (10 wt. % in water), 0.5 ml of aqueous 2 M NaOH, 0.36 ml of PEGDMA550 and 0.44 ml of DI water by stirring. Before the microgel was added the mixture of all of the other materials were allowed to mix for half a minute. The final liquid like mixture was held in a water bath.

Characterisation (i) Effect of Microgel 1 Concentration on Strain Dependent Elastic Modulus (G') and Tan δ (=G"/G') [Note that G" is the Loss Modulus].

The cross-linked microgel was prepared using Example 1, Method A. The dispersions contained 10 wt. % PEGDMA (molar mass was 550 g/mol).

Figure 6:
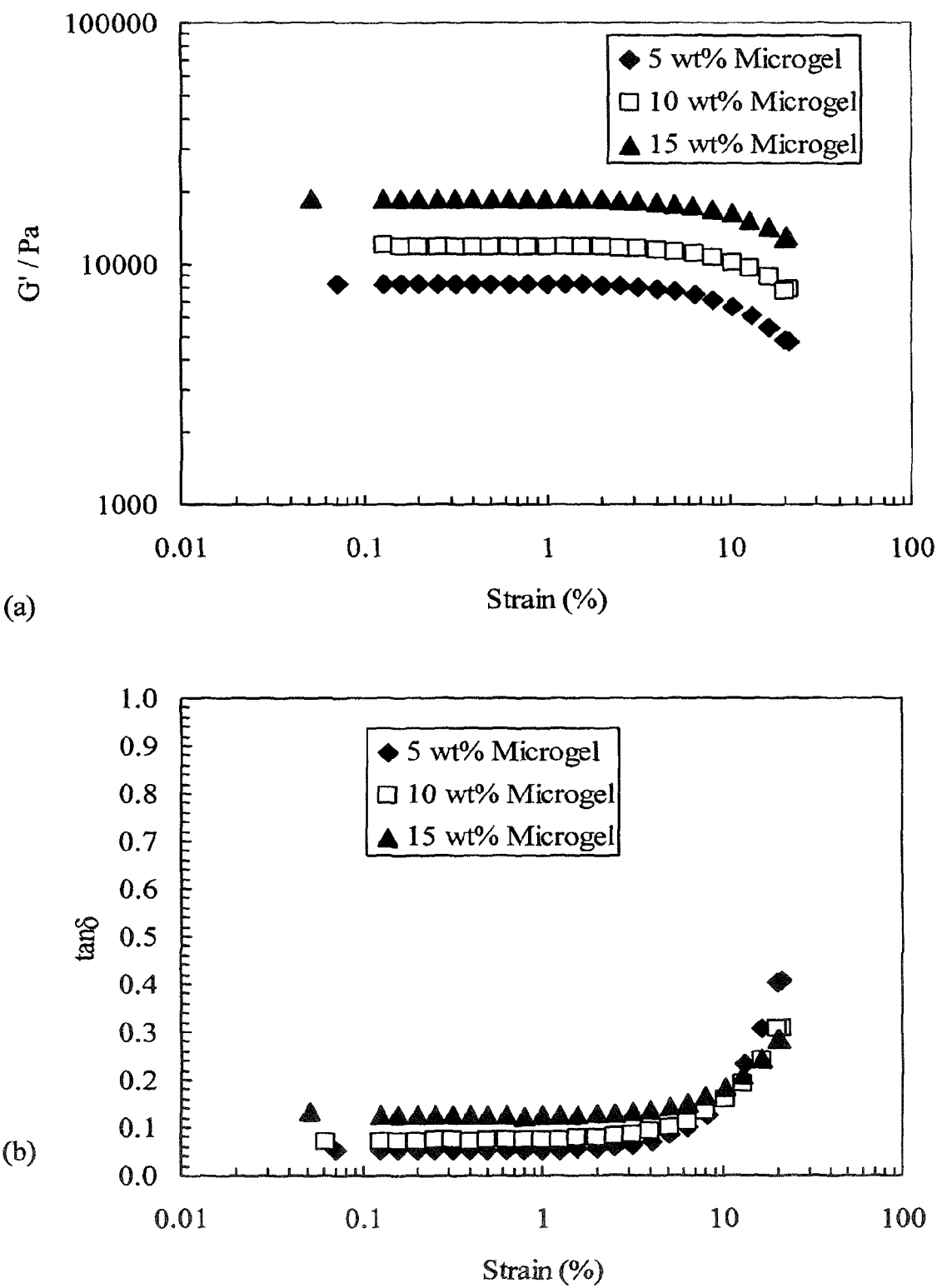

Dynamic rheology measurements were performed using a TA instrument AR G2 temperature-controlled rheometer with an environmental chamber. The results are shown in FIG. 6.

(ii) Variation of (a) G' and (b) Tan δ with Strain for Cross-Linked Microgels Prepared Using Microgel 2A and PEGDMA550.

Figure 7:
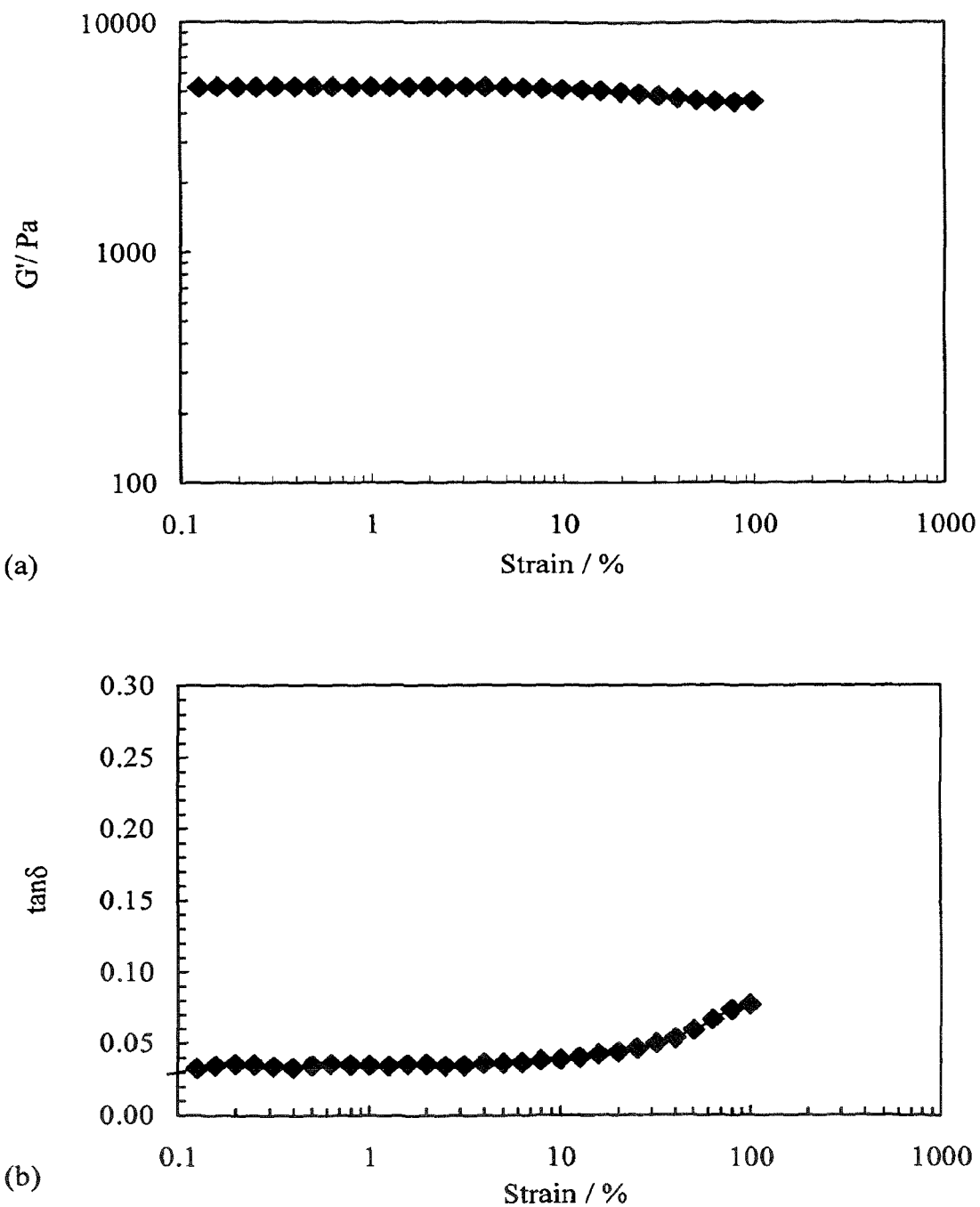

The Microgel and PEGDMA concentrations used were 10 wt. % each. In this case in-situ cross-linking method was performed within the geometry of the rheometer prior to measurement. The instrument was described above. The preparation was done according to Example 1, Method B. The results are shown in FIG. 7.

(iii) Effect of Microgel 1 Concentration on Strain Dependent Elastic Modulus (G') and Tan δ (=G"/G') [Note that G" is the Loss Modulus]

Figure 8:
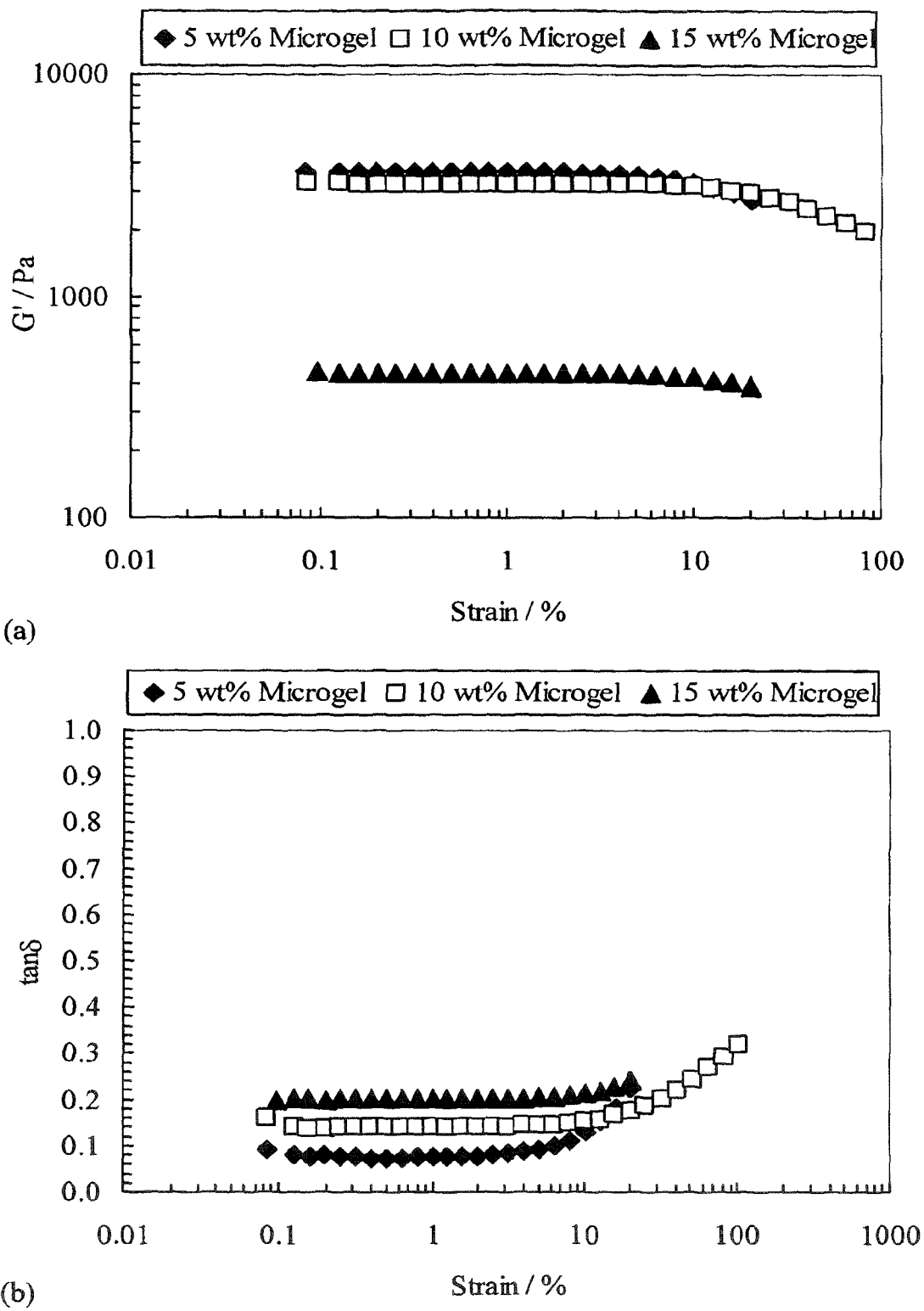

The cross-linked microgel 1 particles were prepared using Example 1, Method B. The dispersions contained 10 wt. % PEGDMA550 (molar mass was 550 g/mol). The instrument was the same as that described above in (i) above. The results are shown in FIG. 8.

Example 2—Cross-Linking of Microgel Particles by Formation of an Interpenetrating Polymer Network and Study of Precursor Microgel/Cross-Linker Networks For a total hydrogel composite containing a total polymer volume fraction ($\phi_{Tot}$) of 0.20, with a microgel volume fraction with respect to total polymer ($\Phi_{\mu^*}$) of 0.5, a mixture of 0.02 wt. % ammonium persulfate was combined with an appropriate amount of sodium hydroxide (Aldrich, 98%) to give a final solution pH of 7.4. To this the crosslinking monomer (X) was added, with the same mole percent as poly(ethylene glycol) dimethacrylate (PEGD550). PEGD (average $M_n$ 550, Aldrich) was then dissolved in this solution, to which 10 wt % of microgel (Microgel μ-BDD—obtained from Method 2 above) was added dropwise whilst mixing using a vortex mixer. The dispersion was then heated at 50° C. for 16 hours.

In this study we use constant molar concentrations of added crosslinking co-monomer. That is, for EGD and the different PEGD crosslinking monomers a constant crosslinking monomer mol. % ($x_X$) is added when data are compared. The value of $x_X$ is the mol. % of X present with respect to all of the monomers present in the μ-BDD/H-X composite. Therefore, the mol. % of monomers present within the microgel is 100–$x_X$. The consequence of this is that there are different volume fraction of crosslinking monomer present.

The microgels are identified as μ-BDD where μ indicates microgel and BDD identifies the crosslinking monomer used (i.e. poly(EA/MAA/BDDA) as obtained from Method 2). When X is polymerised to form a hydrogel network phase this is identified as H-X. The systems (dispersions or gels) contain either μ-BDD and X: (i.e., μBDD/X) or μ-BDD and H-X: (μ-BDD/H-X). The microgel polymer volume fraction in the μ-BDD/X or μ-BDD/H-X mixture with respect to the polymer and monomer or hydrogel present is $\phi_{\mu\text{-}BDD}$. The crosslinking monomer volume fraction present is $\phi_X$. In the microgel/hydrogel composites the volume fraction of the hydrogel polymer (formed by X) is $\phi_{H\text{-}X}$. In both the μ-BDD/X dispersions or μ-BDD/H-X composite gels the total volume fraction of polymer and crosslinking monomer is $\phi_{Tot}$. The following equations apply.

For the μ-BDD/X dispersions:

$$\phi_{Tot} = \phi_{\mu\text{-}BDD} + \phi_X \quad (4)$$

For the μ-BDD/H-X composite gels:

$$\phi_{Tot} = \phi_{\mu\text{-}BDD} + \phi_{H\text{-}X} \quad (5)$$

The volume fraction of microgel with respect to microgel and monomer (or hydrogel) is $\Phi_\mu$.

$$\Phi_\mu = \frac{\phi_{\mu\text{-}BDD}}{\phi_{Tot}} \quad (6)$$

The first part of the study investigated the properties of the μ-BDD/X mixtures. These mixtures were used to prepare the hydrogels. It was important to investigate any changes in microgel properties caused by addition of the monomers. In order to provide good controls the mixtures were heated for the same period of time as used for hydrogel formation; however, APS was not added.

The μ-BDD/X mixtures were prepared initially using a range of $\phi_{\mu\text{-}BDD}$ values. It was found that the behaviour of the mixtures was dependent on the molecular weight of X. If EGD was used then the dispersions remained physical gels over $\phi_{\mu\text{-}BDD}$ values from 0.05 to 0.15. However, if PEG550 was used then the physical gels changed to fluids (as judged by tube inversion) when $\phi_{\mu\text{-}BDD}$ was less than 0.125. Selected images are shown in FIG. 9C. Drawing upon an earlier study which investigated related microgels in the presence of linear PEG homopolymers[9] this behaviour is attributed to osmotic deswelling of the microgels cause by exclusion of the higher molecular weight PEGD550. The lower molecular weight EGD was able to migrate into the interior of the microgel particles and did not cause particle collapse. It is also possible to see evidence of this visually through turbidity changes (see FIG. 9C). FIG. 9C shows images of selected concentrated dispersions. The values for $\phi_{\mu\text{-}BDD}$ and $x_X$ are shown. The pH was 7.4. The turbidity appears independent of $\phi_{\mu\text{-}BDD}$ for the μ-BDD/EGD dispersions. However, it decreases markedly for the μ-BDD/PEGD dispersions with increasing $\phi_{\mu\text{-}BDD}$. At high $\phi_{\mu\text{-}BDD}$ values there is not enough excluded PEGD550 to de-swell the particles.

We probed the effect of PEGD molecular weight using dynamic rheology measurements in order to investigate evidence of a cut off value.

FIG. 6C shows variation of (a) G' and (b) tan δ with strain for μ-BDD/X dispersions. The molecular weight of X is shown in the legend. (c) Shows the values for G' and tan δ measured at 1% strain. (d) Shows the variation of the yield strain with molecular weight of X. In all cases $\phi_{\mu\text{-}BDD}$=0.1 and pH=7.4. The value for $x_X$ used was 15 mol. %

FIG. 6C(a)-(c) show clearly that G' falls and tan δ increases with molecular weight of X. In our experience a G' of about 100 Pa is required for a gel to survive tube inversion. Consequently, the rheological data are consistent with the images of the tubes shown above. It appears from these data that the critical PEGD molecular weight for complete exclusion from the microgel is between 550 and 750 g/mol. This corresponds to 9-13 EO units. Under these conditions the microgel particles are sufficiently collapsed that the physical gels are not strong enough to support their own weight when subjected to tube inversion (FIG. 9C).

The yield strain (γ*) is defined here as the strain at which G' falls to 95% of its value at 1% strain (Chougnet, A.; Audibert, A.; Moan, M. *Rheol. Acta* 2007, 46, 793). This marks the transition to network breakdown. It can be seen from FIG. 6C(d) that there is considerable variation with molecular weight of X for these values. Generally, the physical gels are brittle materials and γ* does not seem to be related to G.

Characterisation (i) Volume Swelling Ratio (Q) for Cross-Linked Microgels Formed According to Example 2 Measured after 7 Days as a Function of μ-BDD Volume Fraction.

The swelling behaviour was investigated for the μ-BDD/H-PEGD550 hydrogel composites at pH=7.4 after 7 days.

Figures 1, 8C:
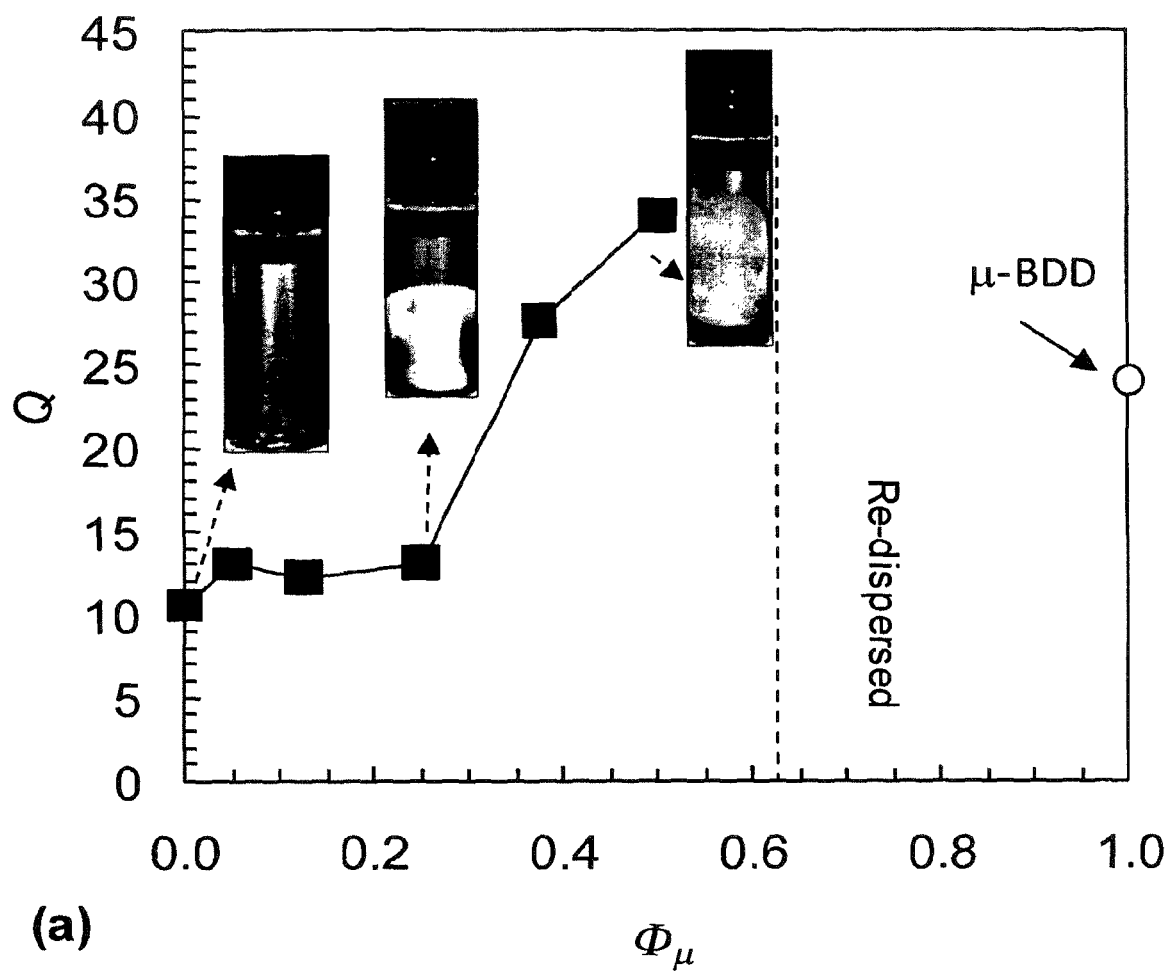
Figures 1, 8C:
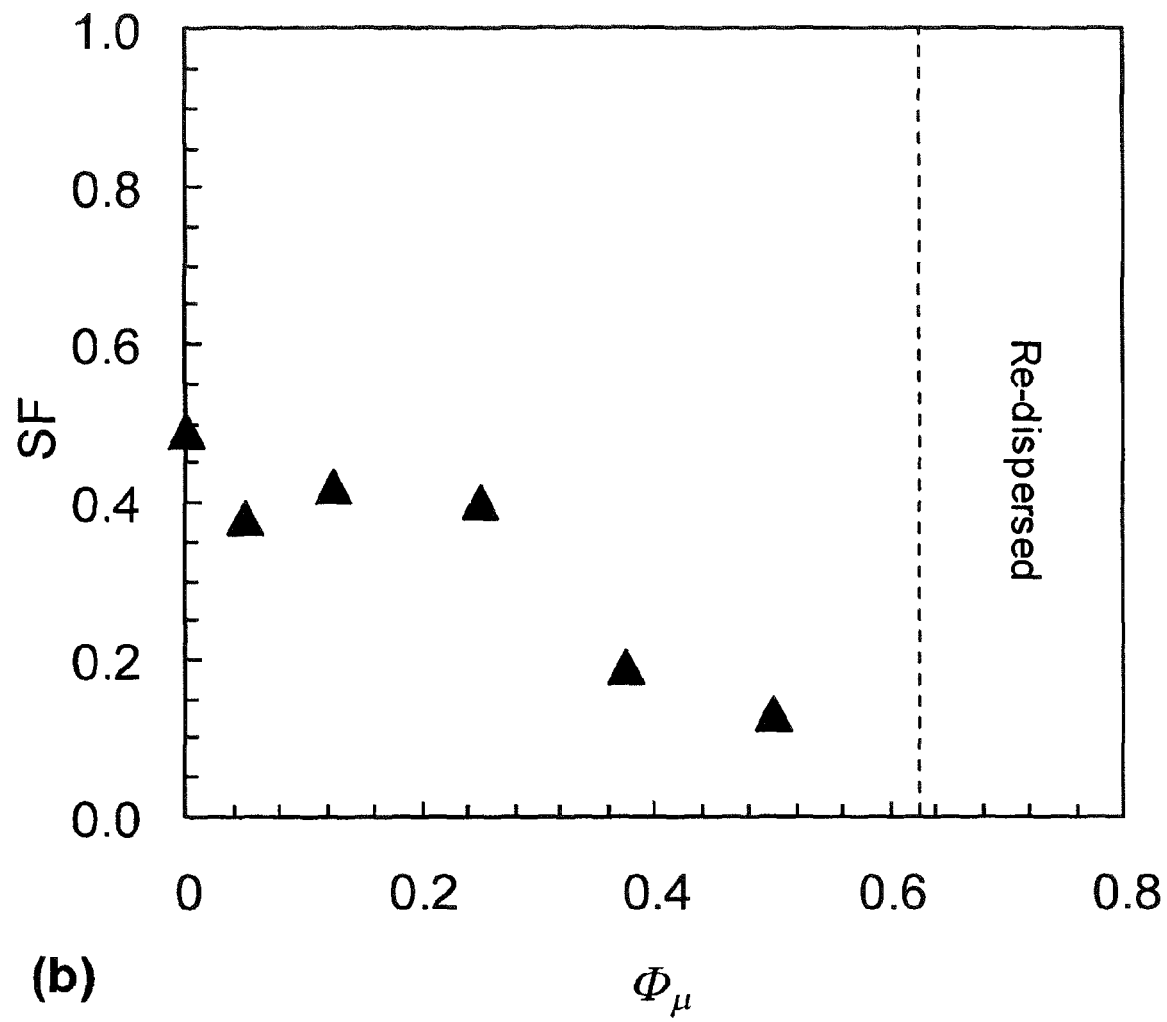
Figures 2, 8C:
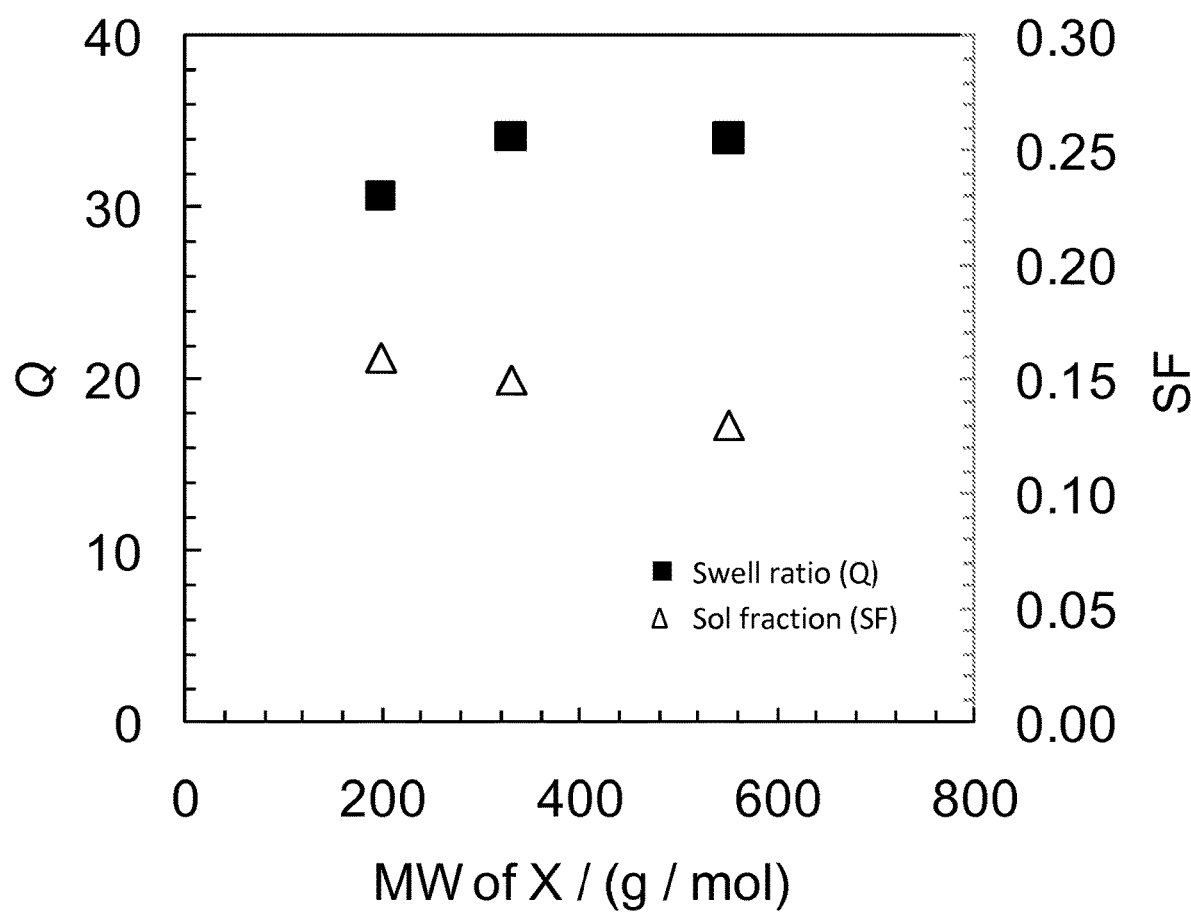
Figures 3, 8C:
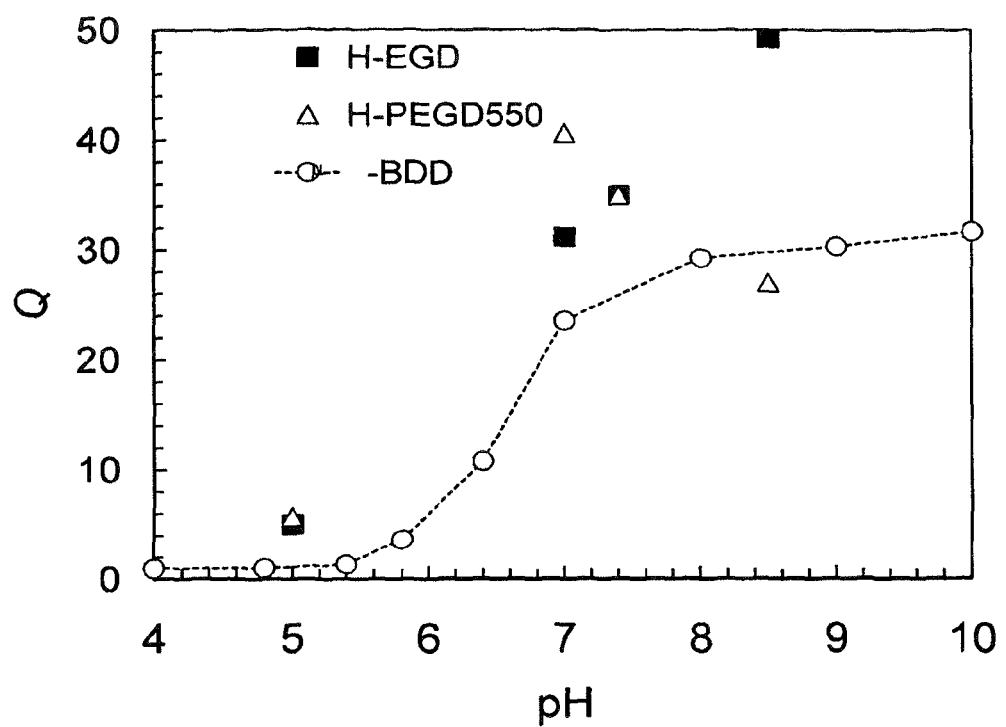
Figure 8C:
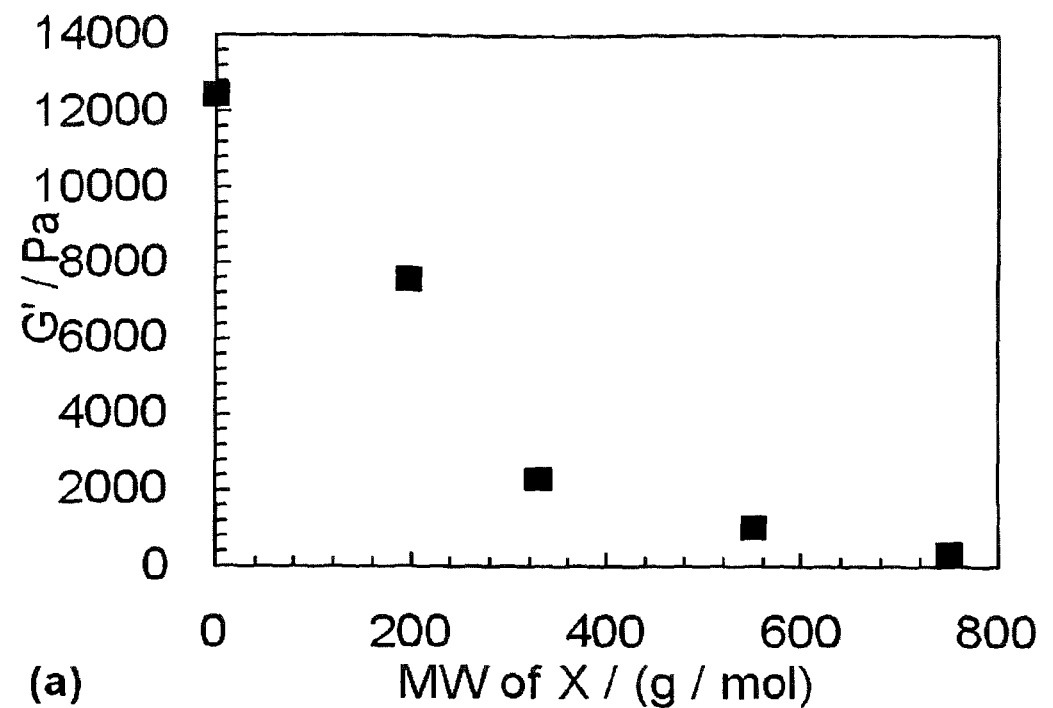
Figure 4:
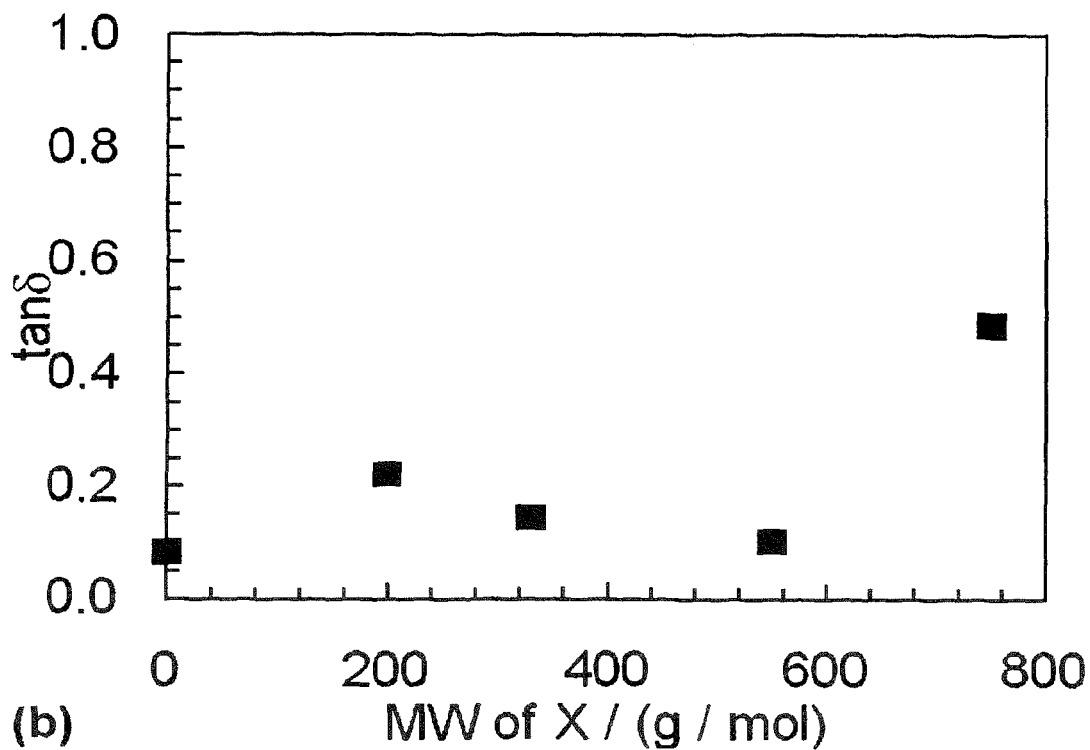
Figures 4, 8C:
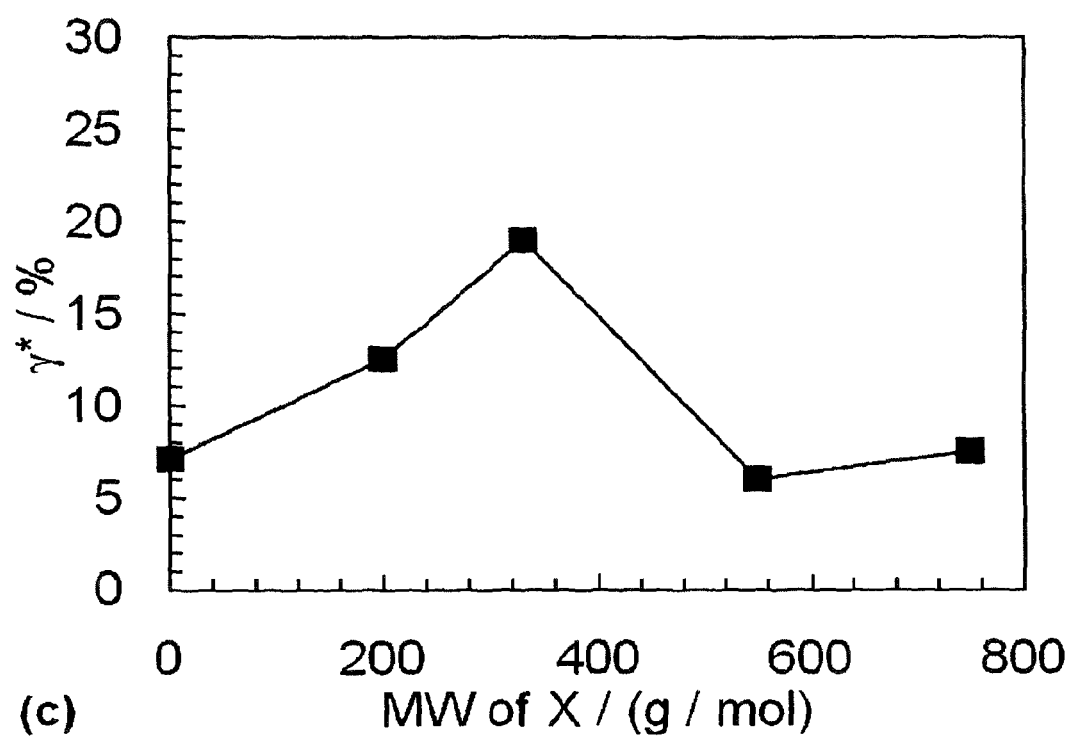

FIG. 8C-1 shows μ-BDD/H-PEGD550 swelling ratio and sol fraction as a function of $\Phi_\mu$. The inserts show selected μ-BDD/H-PEGD550 gels. The composites were prepared using $\phi_{Tot}$=0.2. Note that $\phi_{\mu\text{-}BDD}$=$\Phi_\mu$×$\phi_{Tot}$. The data and images were pH 7.4. Q for the μ-BDD microgel (Table 1) is shown for comparison. The images and data were obtained after 7 days.

The gels were prepared using $\phi_{Tot}$=0.2 and a range of $\Phi_\mu$ values. The Q and SF values were constant until $\Phi_\mu$ exceeded 0.25. At higher $\Phi_\mu$ values Q increased while SF decreased. This is attributed to a decrease in the PEGD550 matrix which had a substantial SF (of about 0.5) and a lower average molecular weight between crosslinks. The microgel particles had a higher Q value than poly(PEGD) because they only contained about 0.5 mol. % of BDD. This can be seen by comparing the data points at $\phi_{Tot}$=0 and 1.0, respectively, for poly(PEGD550) and μ-BDD microgel particles.

The abrupt change in behaviour at $\phi_p$=0.25 is interesting. It may be that this is where a percolated network of microgel particles within the H-PEGD550 matrix first forms. Such as network would be expected to reduce the overall effectiveness of the H-PEGD550 crosslinked phase to constrain the microgel particles. At c values greater than or equal to about 0.63 the gel re-dispersed. This value for $\Phi_\mu$ is very close to the packing volume fraction for a hexagonally close packed system of monodisperse spheres (0.64). It is also in the region of volume fractions where a trapped glass is expected (Debord, S. B.; Lyon, L. A. *J. Phys. Chem. B*. 2003, 107, 2927). It would be reasonable to expect the encapsulating H-PEGD550 phase to become fragmented (non-continuous) under these conditions. The point at which μ-BDD/H-PEGD550 re-disperses ($\phi_M \geq 0.63$) corresponds to the point at which the parent μ-BDD/PEGD550 mixtures form physical gels (FIG. 9C). This shows that re-dispersion is due to the inability of PEGD550 to form a continuous membrane throughout the dispersion.

(ii) Volume Swelling Ratio (Q) for Cross-Linked Microgels Formed According to Example 2 Measured after 7 Days as a Function of the Molecular Weight of X (Cross-Linker)

The effect molecular weight of X on the swelling was also investigated (See FIG. 8C-2).

FIG. 8C-2 shows the effect of MW on swelling ratio and sol fraction for μ-BDD/H-X hydrogel composites. The composites were prepared using $\phi_{\mu\text{-}BDD}=0.10$ and $x_X=15$ mol. %. The gels were then equilibrated at pH=7.4 for 7 days prior to measurement.

It appears that Q increases and SF decreases with MW of the crosslinking monomer. The increase of Q is expected from an increase in the average molecular weight between crosslinks. It is not clear why the SF decreases with MW for these systems at this stage although entanglements may be expected to become more important as the molar mass of X increases.

(iii) Volume Swelling Ratio (Q) for Cross-Linked Microgels Formed According to Example 2 Measured after 7 Days as a Function of pH The μ-BDD/H-PEGD550 and μ-BDD/H-EGD gels were allowed to reach swelling equilibrium. The respective 0 values are shown in FIG. 8C-3.

FIG. 8C-3 shows variation of Q for hydrogel composites with pH. The composites were prepared at pH 7.4, $\phi^-_{\mu BDD}=0.10$ and $x_X=15$ mol. %, placed in 0.1M buffer and allowed to equilibrate for 7 days. Data for μ-BDD obtained from PCS are also shown.

Generally, there is agreement between the 0 values for the gels and the μ-BDD microgel particles. However, there is considerable scatter for the gel data which prevents a more detailed analysis.

(iv) Effect of Microgel μ-BDD Concentration in Example 2 on Strain Dependent Elastic Modulus (G') and Tan δ (G"/G') [Note that G" is the Loss Modulus]

Composite hydrogels (μ-BDD/H-X) were prepared by adding initiator (APS) to the concentrated dispersions discussed above under Example 10. The result of the cross-linking was gels that were more resilient to re-dispersion (later). There was also an increase in the modulus. The increase was most pronounced for the μ-BDD/H-PEGD550 system.

Figure 7C:
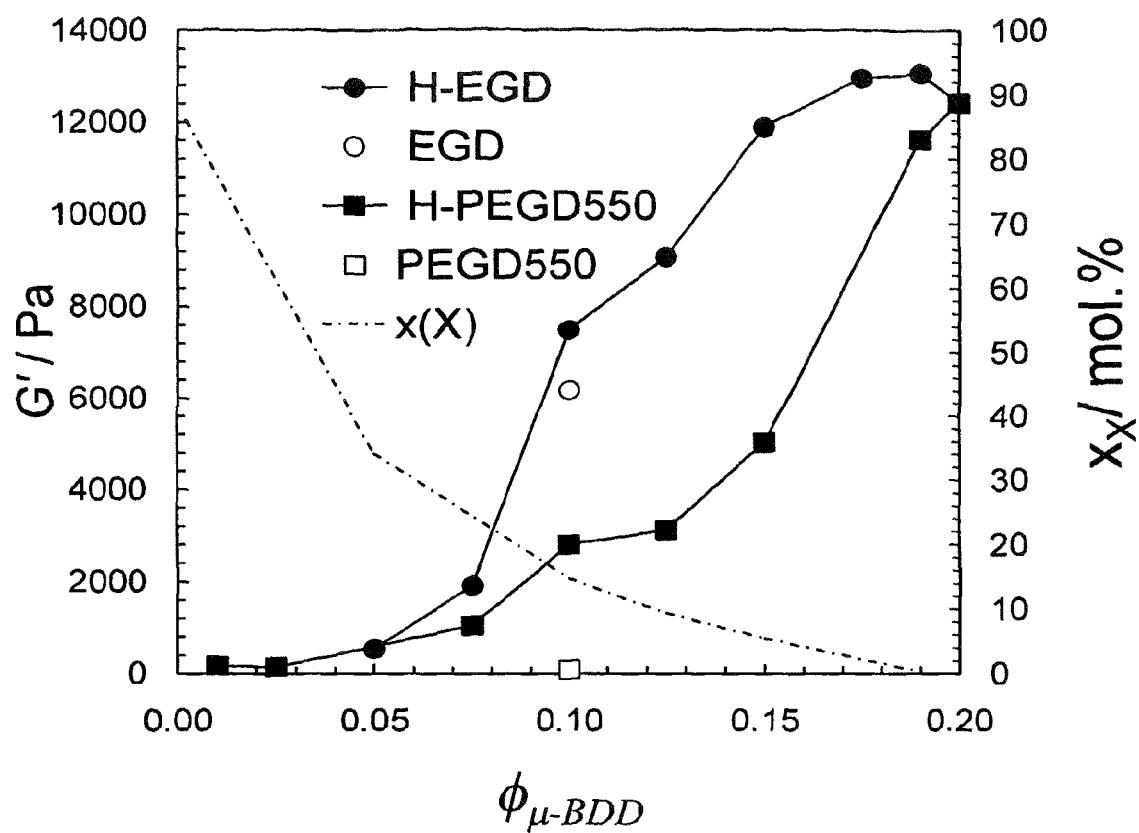

FIG. 7C shows the effect of variation of $\phi_{\mu\text{-}BDD}$ for μ-BDD/H-EGD and μ-BDD/H-PEGD550 hydrogel composites. Selected data for the respective μ-BDD/EGD dispersions are also shown for comparison. The values for $x_X$ are also shown. All systems were measured at pH 7.4. These data illustrate the gap in G' values that becomes increasingly pronounced in the region $\phi_{\mu\text{-}BDD}$ of about 0.10 to 0.17. This indicates an optimum range for osmotic de-swelling of the μ-BDD particles in the presence of PEGD550 before cross-linking.

(v) Effect of Molecular Weight of the Crosslinking Monomer (X) on the Mechanical Properties of Composite Gels of Example 2

The effect of crosslinking monomer molecular weight on the mechanical properties of composite gels prepared using $\phi_{\mu\text{-}BDD}=0.1$ and $x_X=15$ mol. % was investigated in more detail. The results from these data are shown in strain amplitude studies were performed.

FIG. 8C-4 shows data for μ-BDD/H-X composite gels: Effect of molecular weight of X on (a) G', (b) tan δ and (c) γ*. The data were obtained using $\phi_{\mu\text{-}BDD}=0.10$, and $x_X=15$ mol %. The data for (a) and (b) were measured using 1% strain and 1 Hz. Note that the point at MW of 0 corresponds to $\phi_{\mu\text{-}BDD}=0.20$. These data show evidence for a clear change in G' and γ* with MW of X. It can be seen that the MW of 330 g/mol marks a change in the rate of decrease of G' with MW and also a maximum value for γ* (of 19%). This is an indication of a relatively large molar mass between cross-linking points at the particle periphery. The data also show (FIG. 8C-4(b)) that there is an abrupt increase in tan δ at high MW values. This is an indication of increasing dissipation due to a weak network surrounding the de-swollen particles.

Comparison of the data shown in FIG. 6C (see Example 1C) and 80-4 shows that the greatest increase for G' upon composite formation occurs when X is excluded from microgel interior; in that case the fluid (mixture) changes to a solid gel. There is not a great deal of difference for the G' values for the low molar mass crosslinking monomers.

(vi) Effect of $\phi_{\mu\text{-}BDD}$ on G', Tan δ and γ* of Products of Example 2

Figures 5, 8C:
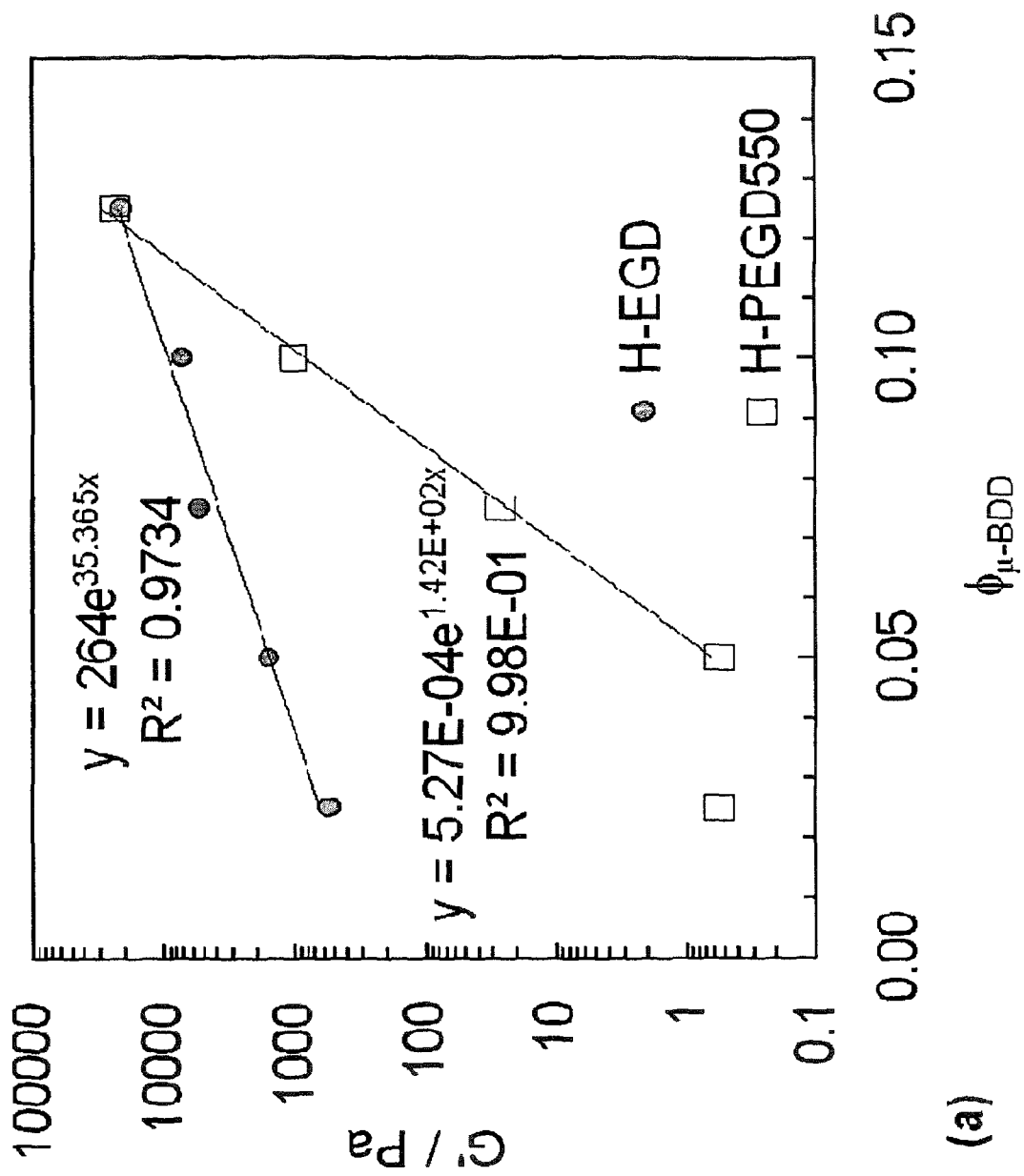
Figures 5, 8C:
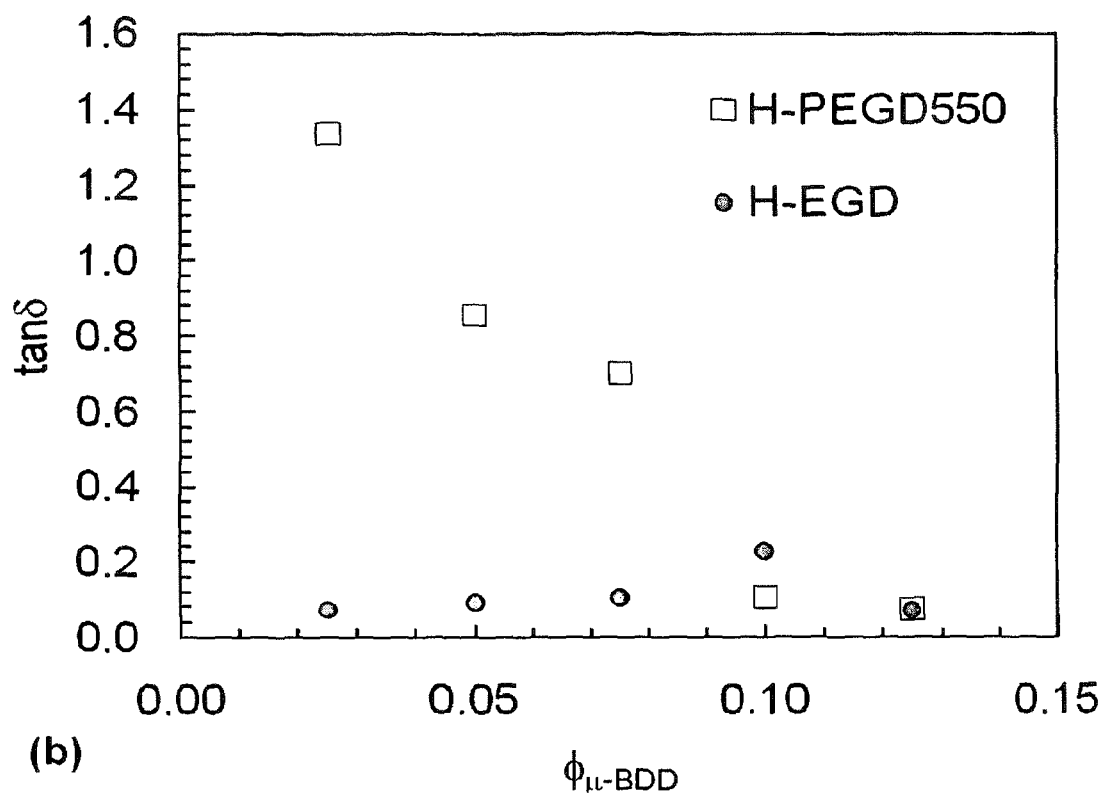
Figures 5, 8C:
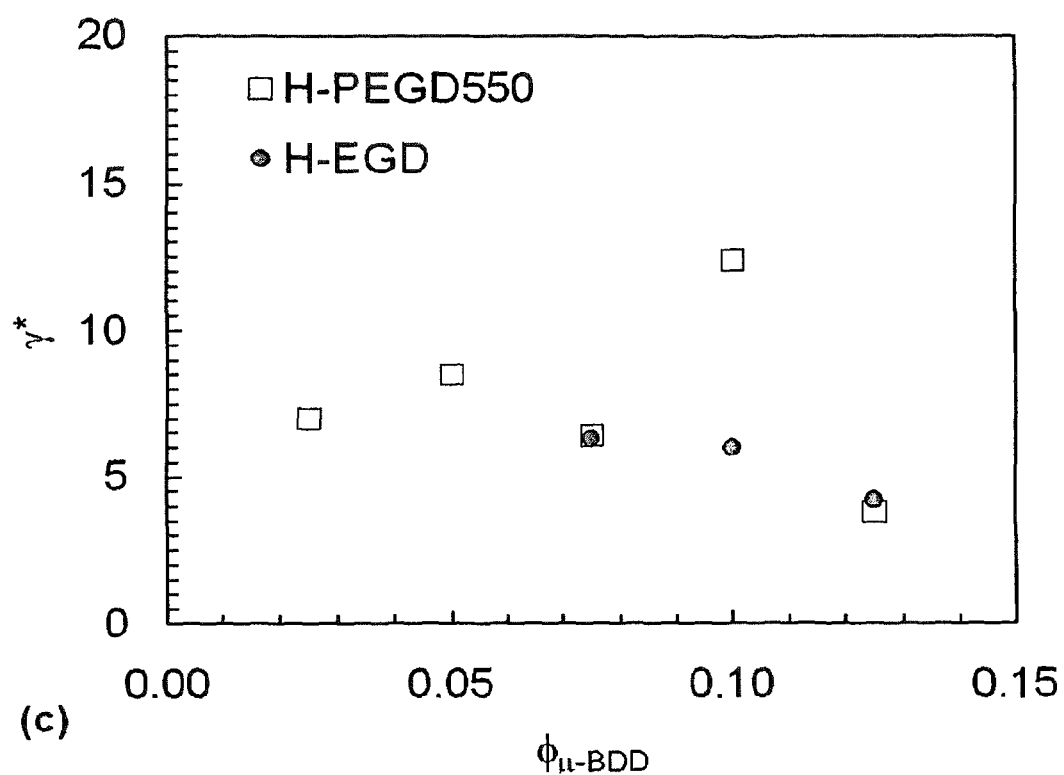
Figures 6, 8C:
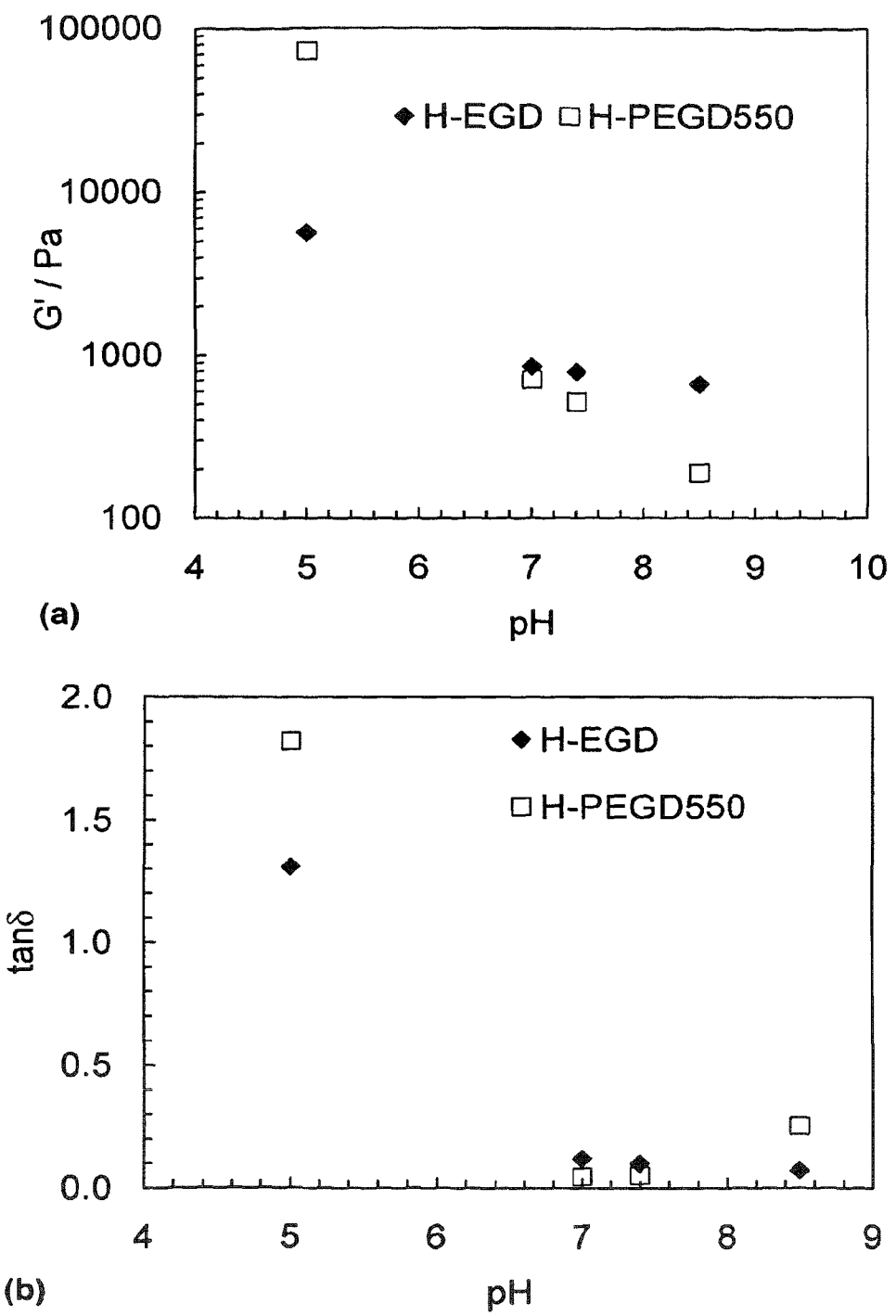

The effect of $\phi_{\mu\text{-}BDD}$ on G', tan δ and γ* were investigated and the data appear in FIG. 8C-5.

FIG. 8C-5 shows the effect of $\phi_{\mu\text{-}BDD}$ on (a) G', (b) tan δ and (c) γ* for μ-BDD/H-EGD and μ-BDD/H-PEGD550 hydrogel composites. The value for $x_X$ was 15 mol. % in each case.

It can be seen that a minimum $\phi_{\mu\text{-}BDD}$ of about 0.05 is required for the μ-BDD/H-PEGD550 systems in order to form a gel with significant elasticity and tan δ<1.0. In the case of μ-BDD/H-EGD the minimum is much lower (less than 0.025). The exponential relationships (FIG. 8C-5(a)) imply tunability through control of $\phi_{\mu\text{-}BDD}$. It is interesting that for both systems there appears to be a $\phi_{\mu\text{-}BDD}$ at which the G' and tan δ values become identical and this is 0.125. The rheological properties of the composites are identical which implies that there is no difference between the load distribution within each type of network at that value of $\phi_{\mu\text{-}BDD}$.

The above data demonstrates considerable tunability for the composites. The greatest changes upon covalent cross-linking occur for the μ-BDD/H-PEGD550 gels. When $\phi_{\mu\text{-}BDD}=0.1$, they change from a fluid to a gel. This indicates good potential for an injectable dispersion.

(vii) Effect of pH on Strain Dependent Elastic Modulus (G') and Tan δ (=G"/G') [Note that G" is the Loss Modulus] for Example 2

The rheological properties of the equilibrium swollen gels were also investigated.

FIG. 8C-6 shows variation of (a) G' and (b) tan δ with pH for μ-BDD/X composite hydrogels. These were the same gels used for the swelling experiments shown in FIG. 8C-3.

It can be seen that in the physiological pH range the composite gels have low G' values. They were also quite brittle with γ* values less than 5%. Both of these effects can be attributed to highly swollen chains. The Q values are in the vicinity of 30 to 40 from FIG. 8C-3 at these pH ranges (7 to 7.4). This corresponds to a $\phi_p$ value of only 0.02 to 0.03. Therefore, in the fully swollen state these composites are weak gels. However, the data from FIG. 8C-5 shows that much more elastic gels can be achieved by limiting swelling to a range where the $\phi_p$ values are larger.

Conclusions

The type of hydrogel composite that is obtained depends on the MW of the added crosslinking monomer. If the MW is smaller than the exclusion limit (ca. 550 g/mol) then it penetrates the swollen microgels and reinforces the physical gels to produce network threaded microgels. If the MW is greater than this value the monomer is excluded and cross-links around the microgel particles, encapsulating them, to form a microgel-reinforced hydrogel. In the latter case the excluded crosslinking monomer caused deswelling and this resulted in a fluid rather than a physical gel. The μ-BDD/X fluid changed to a gel upon crosslinking. This is an advantageous result from the viewpoint of potential application because the latter systems are injectable prior to gelation. The work has also demonstrated that the mechanical properties of the hydrogel composites can be tuned by the composition used for their preparation. The modulus values obtained in this work (1000-30,000 Pa) match those of a range of soft tissues in the body. Further, the ability to tune the modulus values suggests that the mechanical properties of these hydrogel composites will be suitable for application in intervertebral disc repair.

Example 3—Cross-Linking of the Vinyl-Grafted Microgel Particles 2.5 ml of poly(MMA/MAA/EGDMA)-GMA microgel (16 wt. %) was added to a mixture of 0.2 ml of ammonium persulfate solution (10 wt. % in water), 0.5 ml of aqueous 2 M NaOH and 0.8 ml of DI water by stirring. The final pH was maintained between 7.5 and 8.5. The dispersion was heated to the desired temperature. In the case of preparations conducted at 37° C., TEMED was added at concentrations between (2 and 50 mM).

Figure 9:
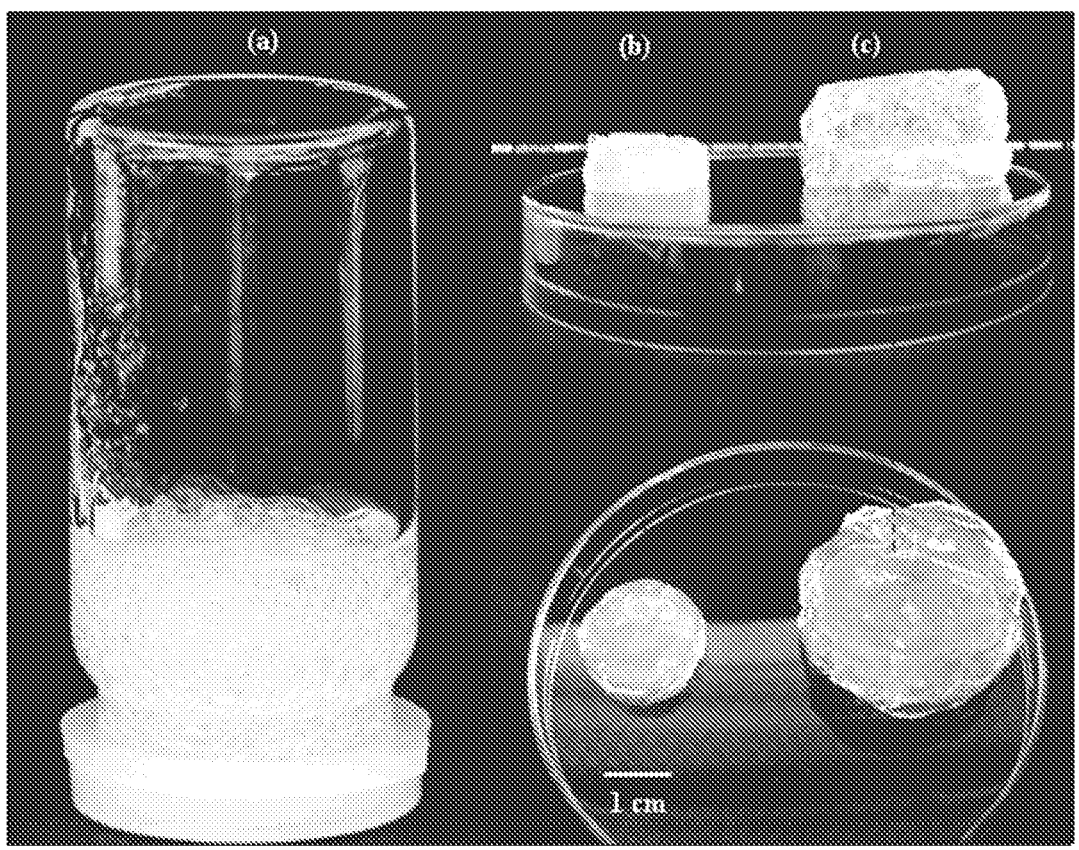

FIG. 9 shows a photographic image of: (a) a Microgel 2B dispersion (at pH=7.3); (b) a cross-linked 2BG microgel; and (c) a cross-linked 2BG microgel that has swollen in neutral pH water. For each gel shown in FIG. 9, the initial microgel concentration corresponded to 7 wt. %. The gels were prepared using the procedure outlined in Example 2 above at a temperature of 50° C., and in the absence of added TEMED.

Figure 10:
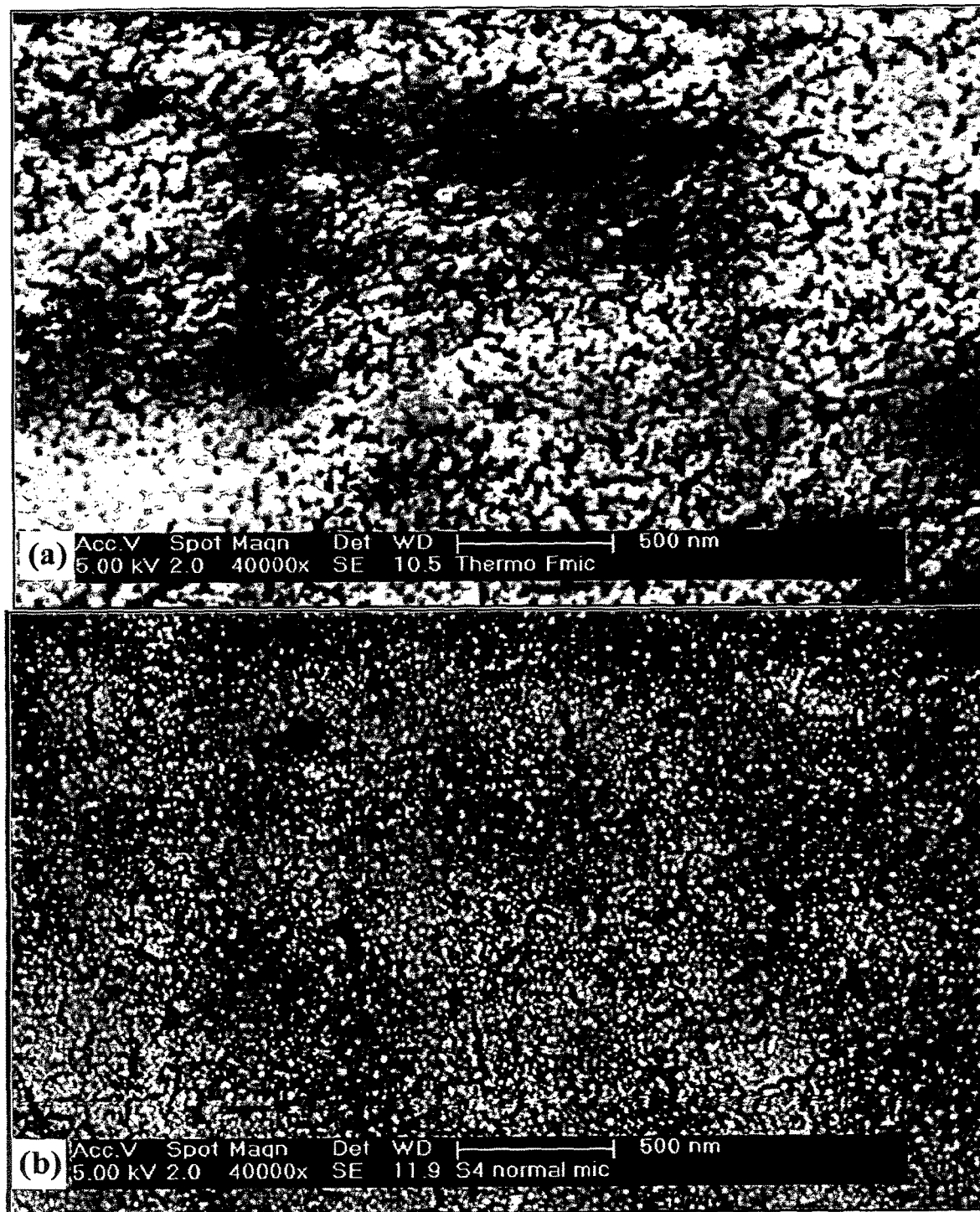

FIG. 10 shows scanning electron micrograph images of: (a) a cross-linked 2BG microgel and (b) a non-cross-linked microgel dispersion (Microgel 2B), both at the same particle concentration (10 wt. %). SEM image was obtained using a Philips FEGSEM instrument. Sample (a) was prepared using the method described in Example 2 above and sample (b) was prepared using the procedure described in Method 1. In the case of sample (a) TEMED was not added and the reaction was performed at 50° C.

Characterisation (i) Volume Swelling Ratio ($q_{gel}$) for Cross-Linked Gels of Microgel 2BG Measured after 7 Days as a Function of pH.

Data measured in a buffered phosphate buffered saline solution (PBS) are also shown. The value for $q_{gel}$ was measured using the ratio of the gel volume at a given pH to the volume of the water-free (dry) gel. This was done gravimetrically after blotting excess water from the swollen gel using tissue paper.

The double cross-linked microgel was prepared using heating at 50° C. as described for Example 2. However, in this case TEMED was not added.

Figure 11:
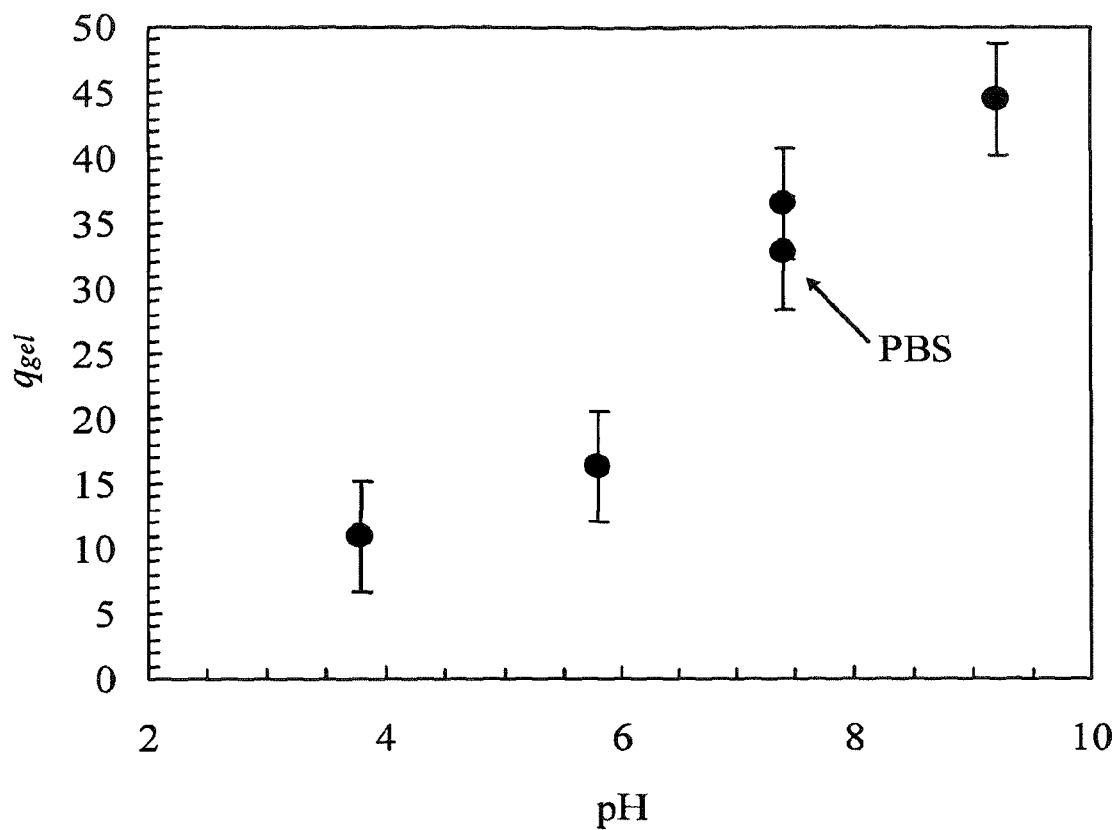

The results are shown in FIG. 11.

(ii) Effect of Microgel 2BG Particle Concentration Used During Cross-Linking on (a) G' and (b) Tan δ as a Function of Strain.

The double cross-linked microgel was prepared using heating at 50° C. using Example 2 in the absence of added TEMED. The values of γ* were determined as described above. The instrumentation for rheology was also described above.

Figure 13:
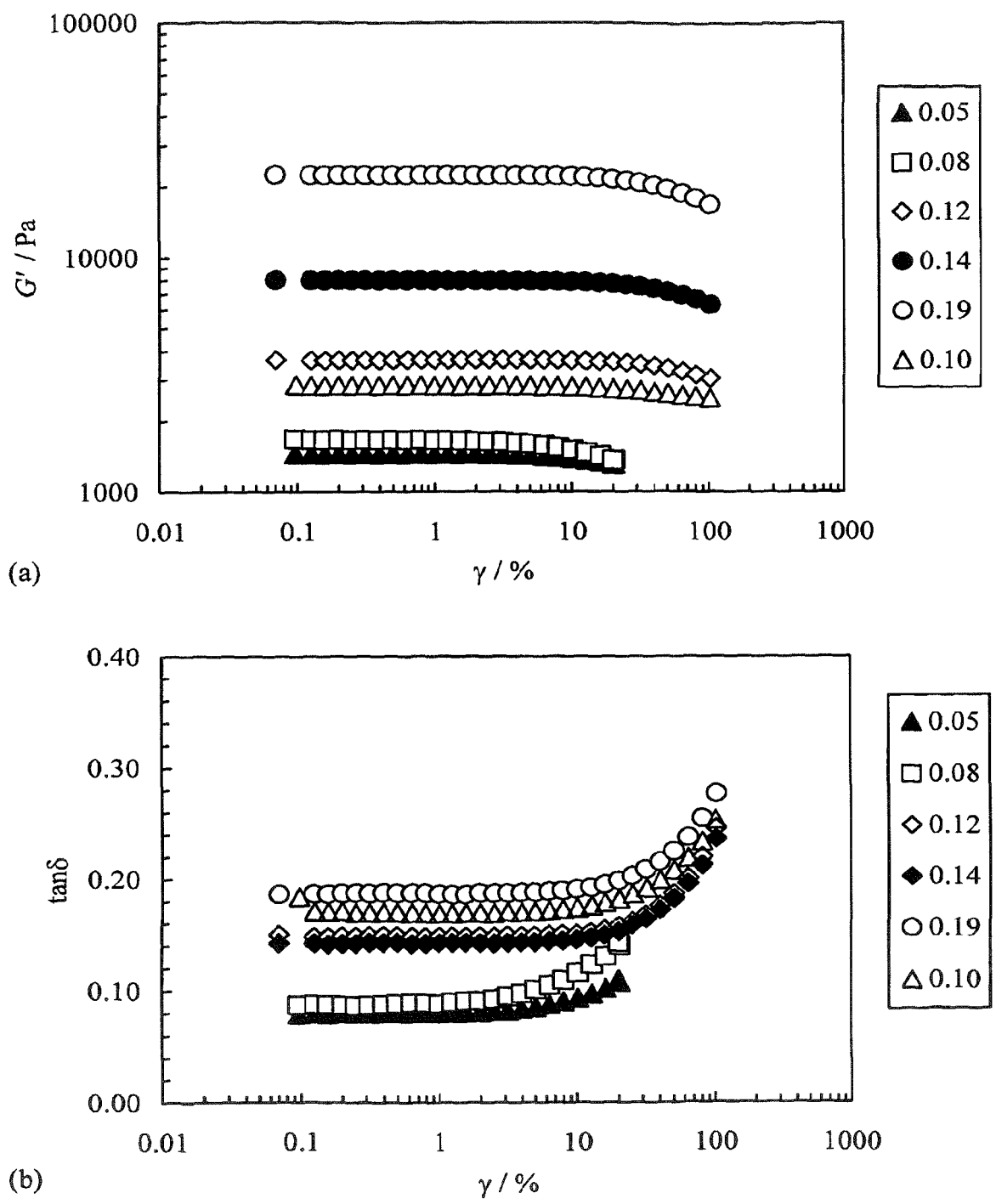
Figure 13:
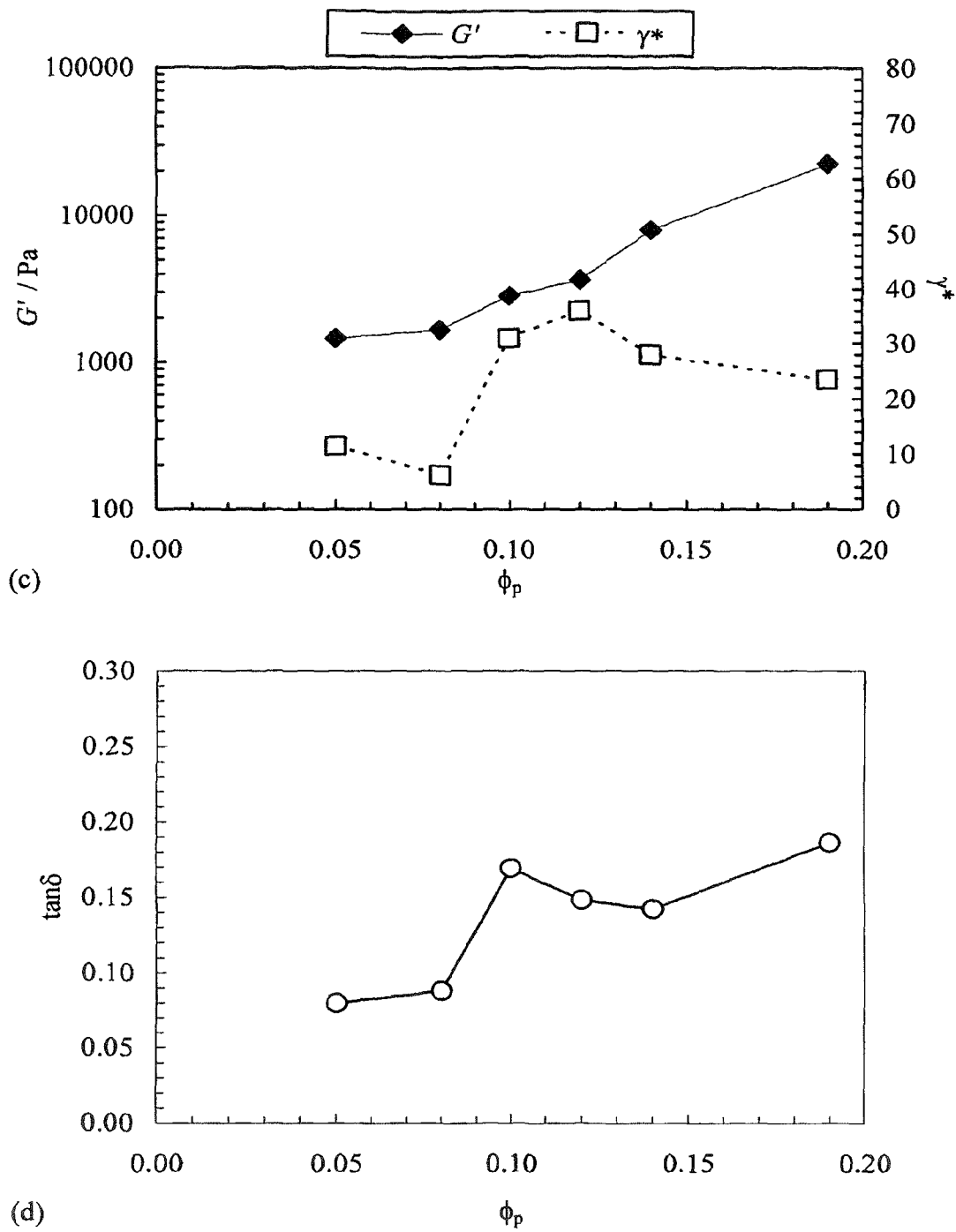

The results are shown in FIG. 13. The volume fraction of polymer used during preparation is shown in the legend. [Multiply by a factor of 100 to convert to wt. %] The variation of G', γ* and tan δ with volume fraction of polymer are shown in (c) and (d). The pH for these data was 7.8. For these measurements, and the others given in the examples, the oscillation frequency was used 6.3 rad/s unless otherwise stated.

(iii) Variation of (a) G' and (b) Tan δ with Strain for Cross-Linked Microgels Prepared.

Figure 14:
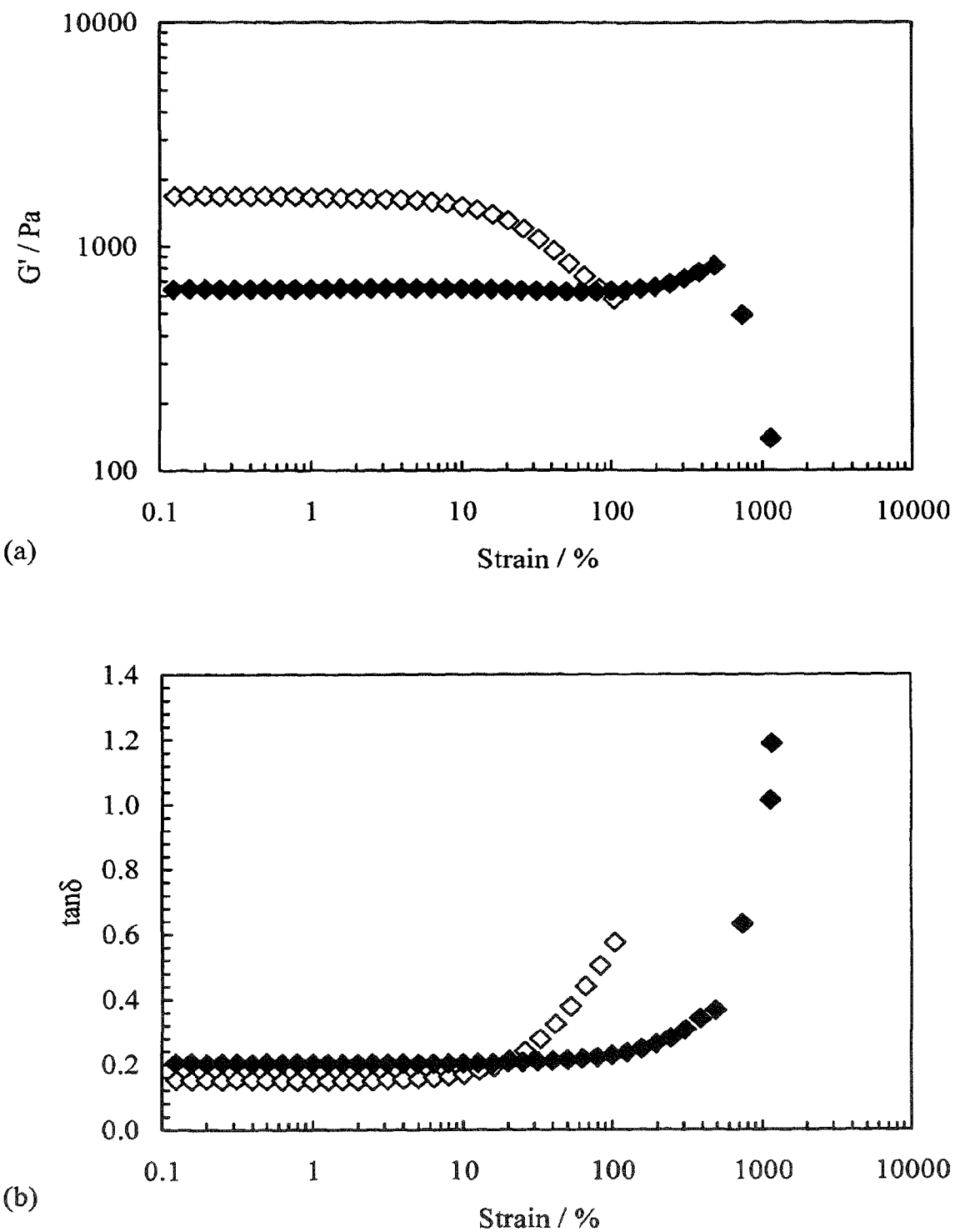

The data were obtained using Microgel 2BG (open diamonds) and 3G (closed diamonds). The double cross-linking was performed at 37° C. using ammonium persulfate (22 mM) and 10 wt. % of the microgel for 17 h using Example 2 in the absence of added TEMED. The value for γ* for doubly cross-linked 3G is in the vicinity of 500%. For these experiments the hydrogel was prepared in-situ within the rheometer just prior to measurements occurring using Example 2. The results are shown in FIG. 14.

(iv) Variation of (a) G' and (b) Tan δ with Strain for Doubly Cross-Linked Microgels Prepared from Microgel 2BG and TEMED (7.98 mM).

The cross-linking was performed at 37° C. The reaction time is shown. The estimated values for g* is 195% for the system after 120 min of reaction. The system was prepared using 10 wt. % Microgel 2BG.

Figure 15:
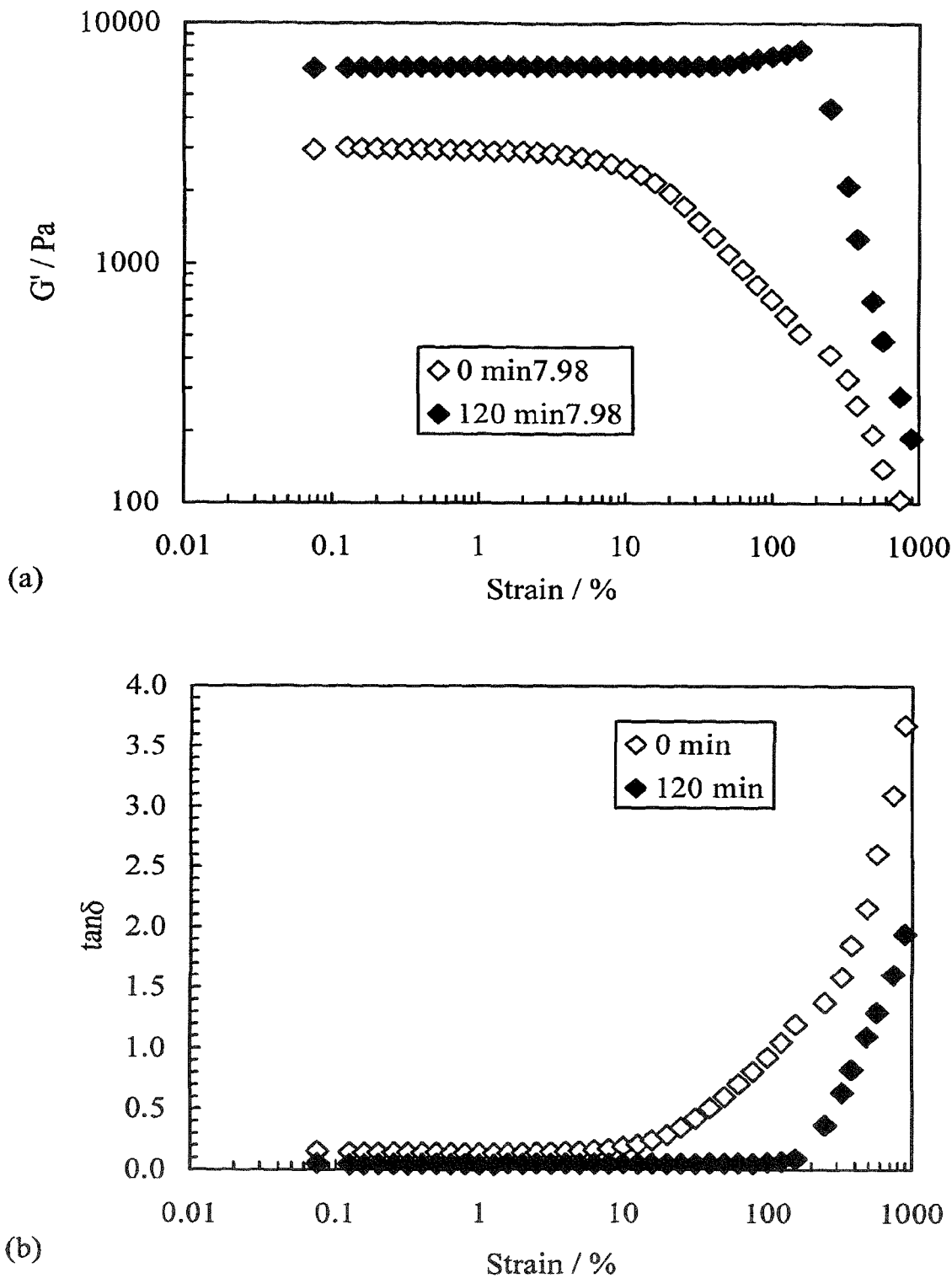

This was measured after situ cross-linking within the rheometer using the procedure of Example 2. The results are shown in FIG. 15.

Example 4—Cross-Linking of the Vinyl-Grafted Microgel Particles

Generally, the doubly cross-linked microgel particle composition (DX microgel) was prepared using $\phi_p$=0.10, pH=7.8, 22 mM of APS and a reaction temperature of 50° C. The GM-functionalised microgel (e.g. Microgel GM-M-EGD of Method 3A) was added to the NaOH/APS solution with vigorously mixing for about 5 minutes to form a physical gel at room temperature. After fully mixing the physically gelled dispersion was heated at 50° C. for 8 h, and was allowed to react to yield DX GM-M-EGD.

For measurements performed using rheology the cross-linking was conducted in-situ within the rheometer for at least 1 h prior to commencing the measurements. For the larger samples prepared for swelling measurements the reaction time was 8 h.

Figure 9A:
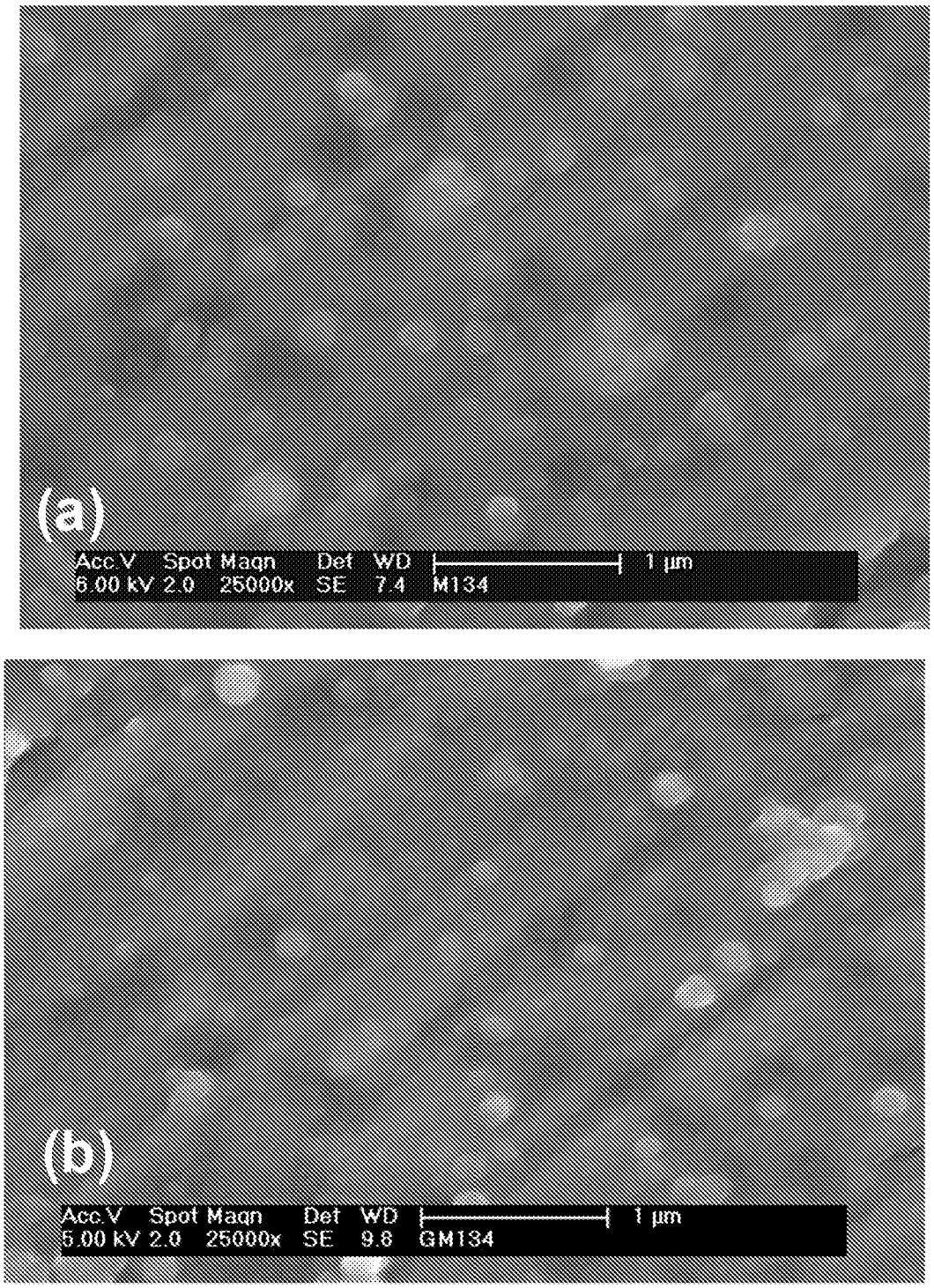

FIG. 9A shows an SEM photographic image of: (a) Microgel M-EGD (of Method 1A); (b) Microgel GM-M-EGD (of Method 3A). The particles are spherical although the polydispersities are significant. Table 2 shows that the number-average particles sizes for these two microgels were about 130 nm and not significantly affected by functionalisation. Comparison of the diameters measured by SEM and also PCS (at pH=4) shows they are similar. This indicates that there was negligible aggregation of the particles in dispersion.

TABLE 2

| Code | Mol. % MAA[a] | Mol. % GMA[a] | $d_{n(sem)}$/nm (CV)[b] | $d_{h(4)}$[c]/nm | $d_{h(8)}$[c]/nm | $Q_{(8)}$[d] | $pK_a$[e] |
|---|---|---|---|---|---|---|---|
| M-EGD | 35.9 | — | 131 (14) | 139 | 232 | 4.7 | 7.4 |
| GM-M-EGD | 34.1 | 1.8 | 133 (20) | 131 | 323 | 15 | 7.1 |
| GM(H)-M-EGD | 35.9 | 5.8 | | 133 | 315 | 13 | 6.0 |

[a]Determined from potentiometric titration data. The mol. % GMA was determined from the difference in the mol. % MAA in the microgel before and after functionalisation.
[b]Number-average diameters determined from SEM images. The number in brackets is the coefficient of variation.
[c]Hydrodynamic diameter at pH values of 4 and 8.
[d]Swelling ratio calculated using $d_{h(8)}$ and $d_{(4)}$ values for the parent microgel according to equation (1) - see text.
[e]Apparent $pK_a$ values. These are the pH values corresponding to 50% neutralisation.

Figure 10A:
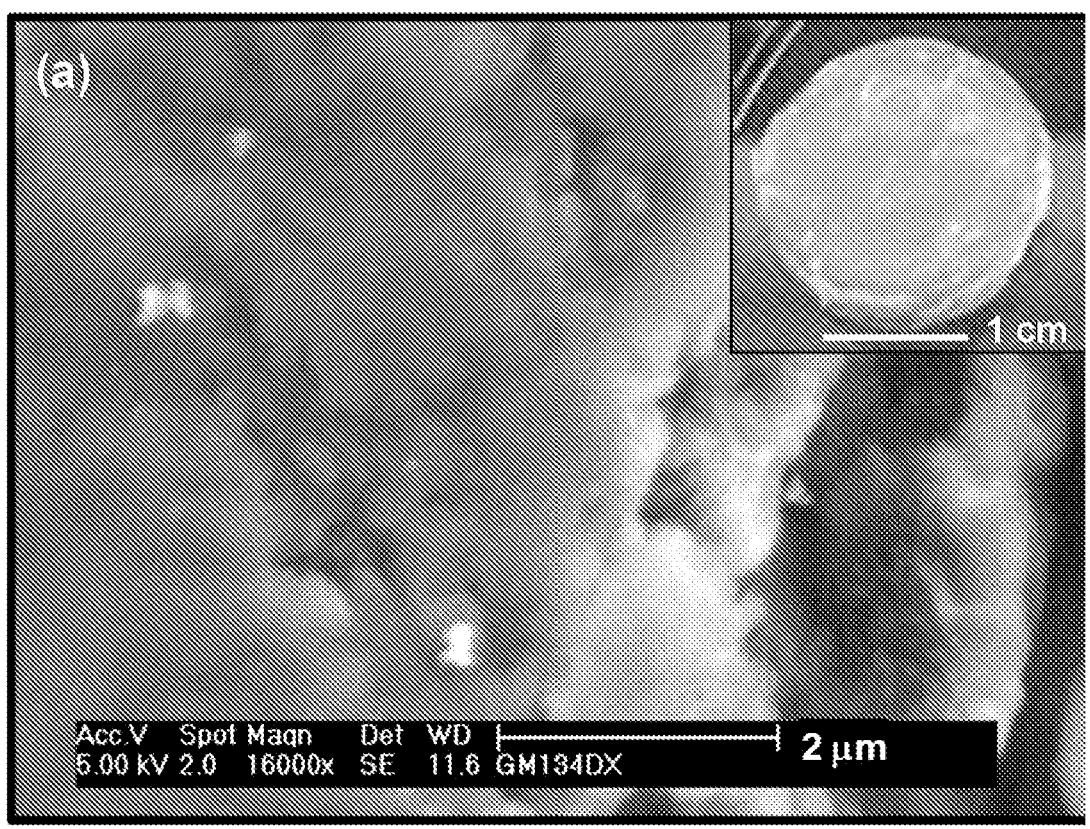
Figure 10A:
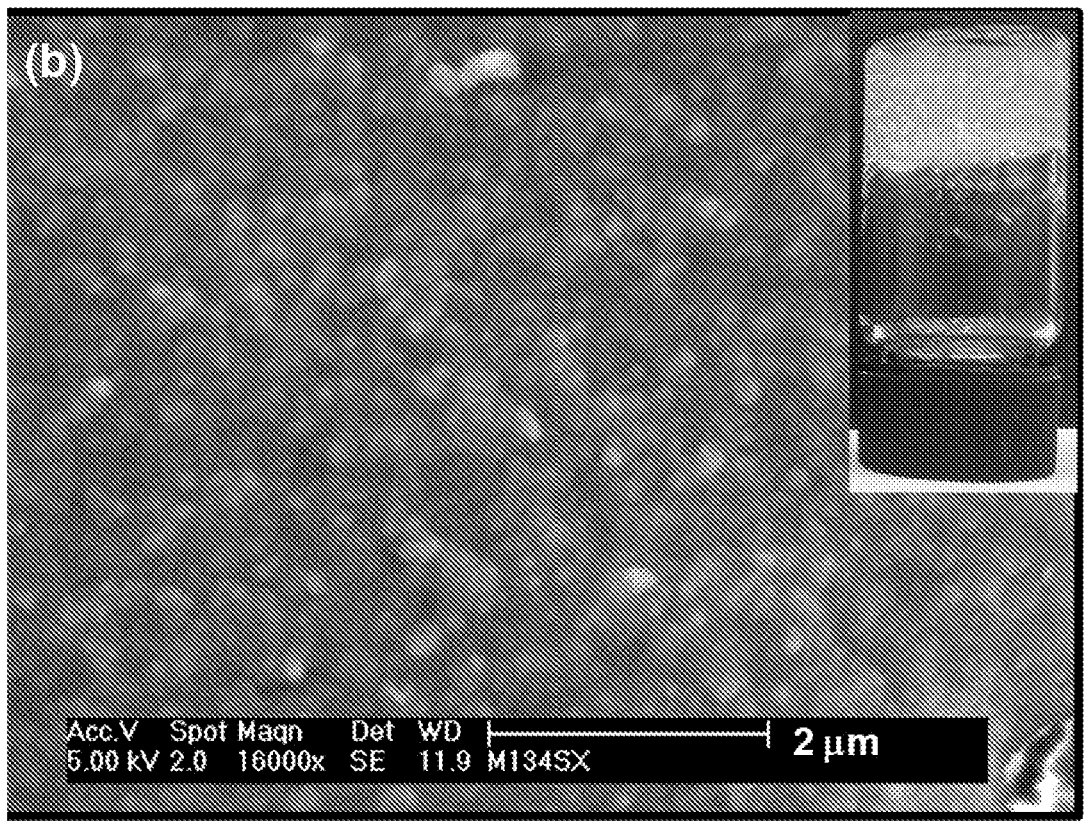

FIG. 10A shows scanning electron micrograph images of freeze-dried samples of: (a) DX GM-M-EGD and (b) M-EGD (i.e. The sample was prepared using $\phi_p$=0.10 and pH=7.8. The insets for (a) and (b) show a pictures of a free-standing DX GM-M-EGD microgel and a physically gelled, M-EGD dispersion, respectively. SEM image was obtained using a Philips FEGSEM instrument. Sample (a) was prepared using the method described in Example 2A above and sample (b) was prepared using the procedure described in Method 1A. Freeze-drying has a tendency to produce micrometer-sized voids as a consequence of ice formation during sample immersion in liquid nitrogen. Nevertheless, it was found that features on the scale of individual particles were less common with the DX gels (FIG. 10A(a)) compared to the parent SX M-EGD gel (FIG. 10A(b)), which may indicate a greater extent of inter-particle intepenetration. The GM-M-EGD particles had a greater tendency to swell than the M-EGD particles (see below).

Characterisation (i) Volume Swelling Ratio (Q) for Cross-Linked Gels of Microgel DX GM-M-EGD as Prepared in Example 4 after 8 Days as a Function of pH.

This double cross-linked microgel was DX GM-M-EGD as prepared in Example 2A.

Physical measurements were conducted as described above.

In the following study the mechanical properties of DX microgels that were allowed to reach swelling equilibrium were studied. We used conditions just below the critical $\phi_p$ value of 0.10 because this was a more stringent test of whether DX microgels could in fact survive swelling without disintegration. Furthermore, the SX gel had sufficiently low G' values that they were fluid when sheared by tube inversion. This means that these mixtures would be injectable through a narrow gauge syringe. That would be advantageous for soft tissue repair if low temperature crosslinking was used.

The $Q_{DX}$ microgels swelled strongly in buffer or water. The DX GM-M-EGD microgel swelled so strongly in water that it fragmented macroscopically after several days. This shows that the inter-particle crosslinking was not sufficiently strong to withstand the swelling pressure within the particles. If the DX microgel was placed in buffer solutions (ionic strengths of $\phi_p$=0.1 M) they gave robust gels that did not fragment. The high ionic strength reduced the extent of swelling and shows the importance of electrostatic repulsion in the swelling of these DX microgels.

Figure 12A:
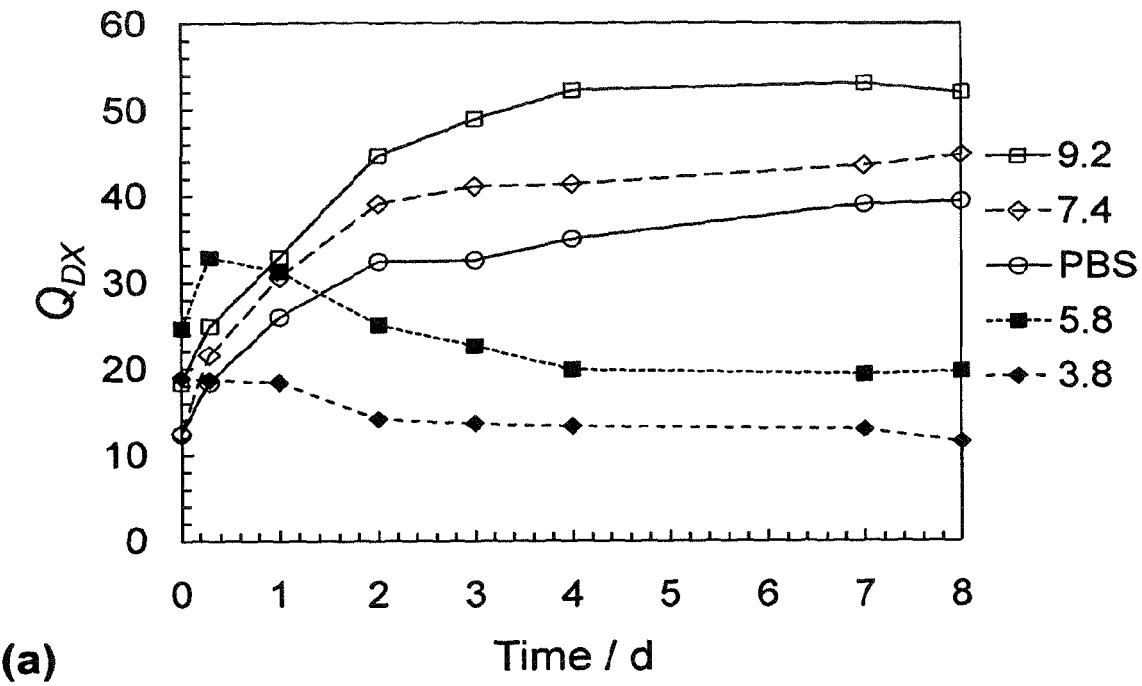
Figure 12A:
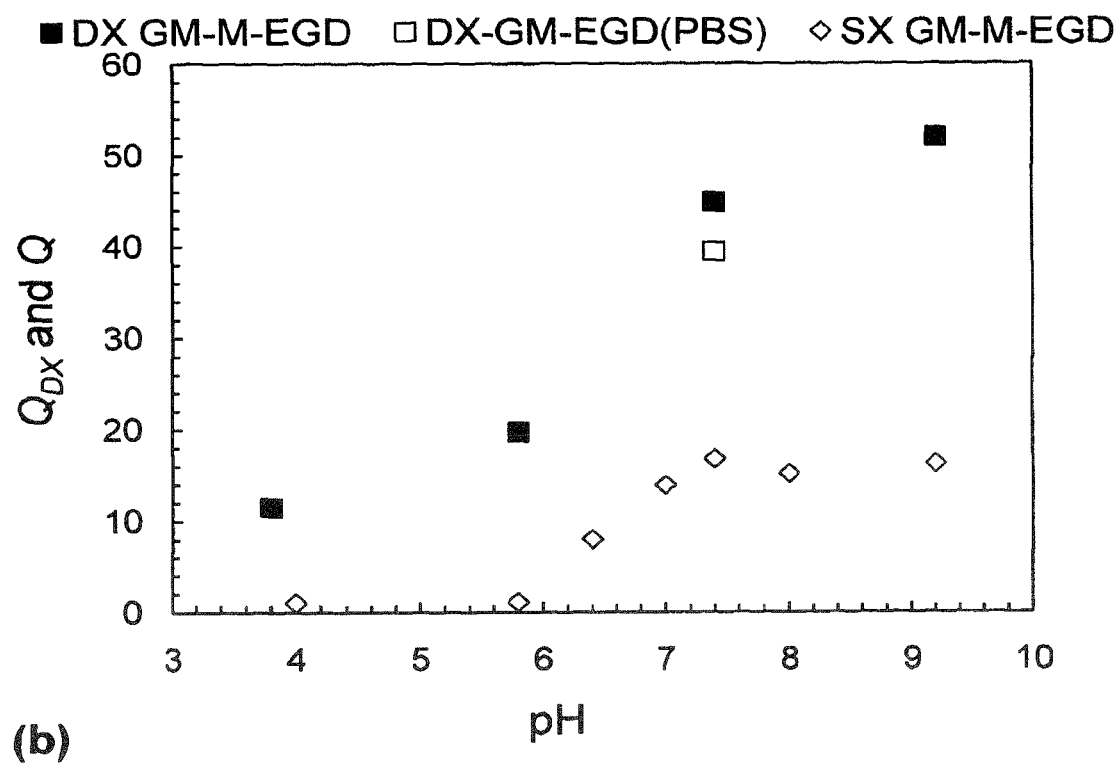
Figures 1, 12A:
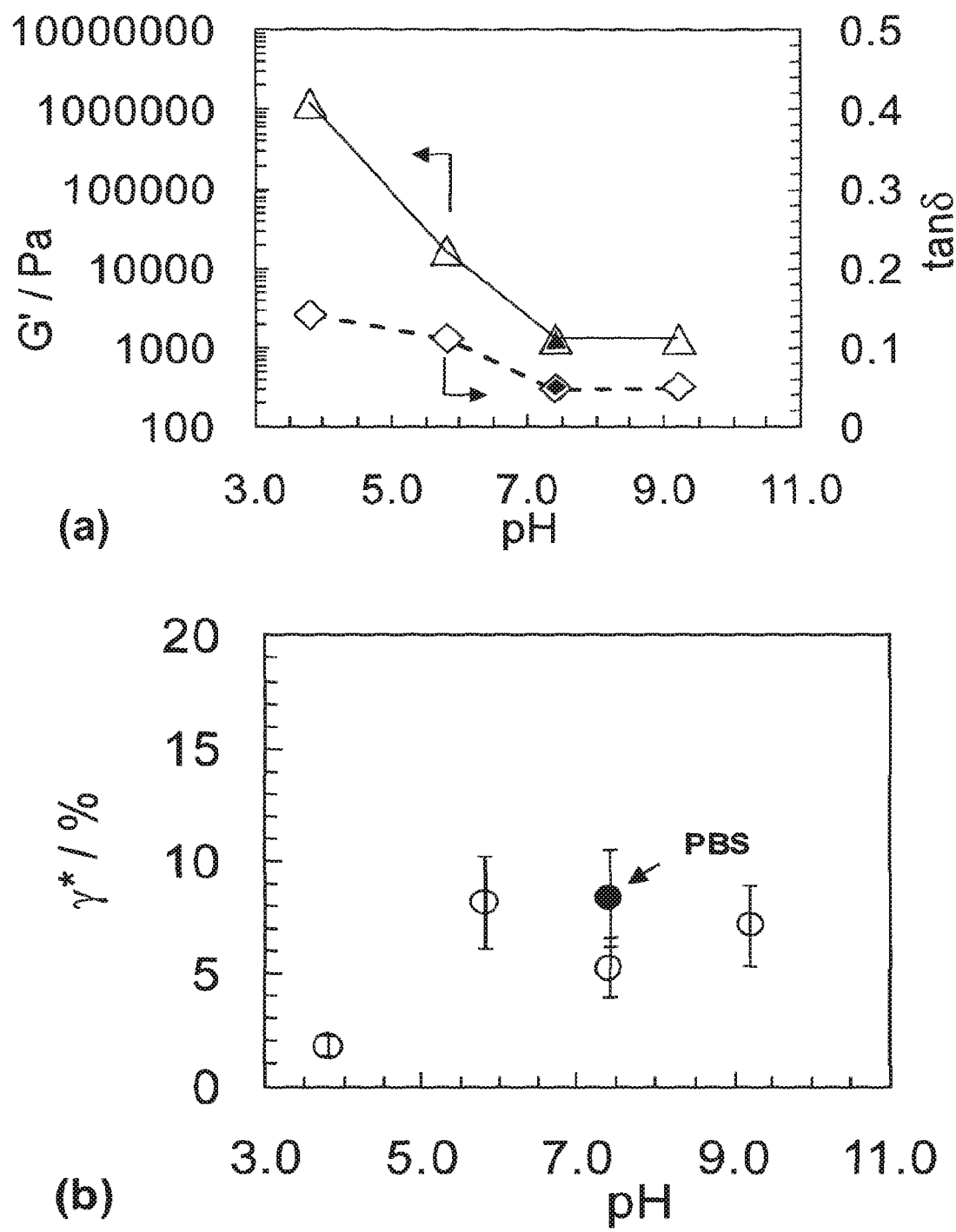
Figures 2, 12A:
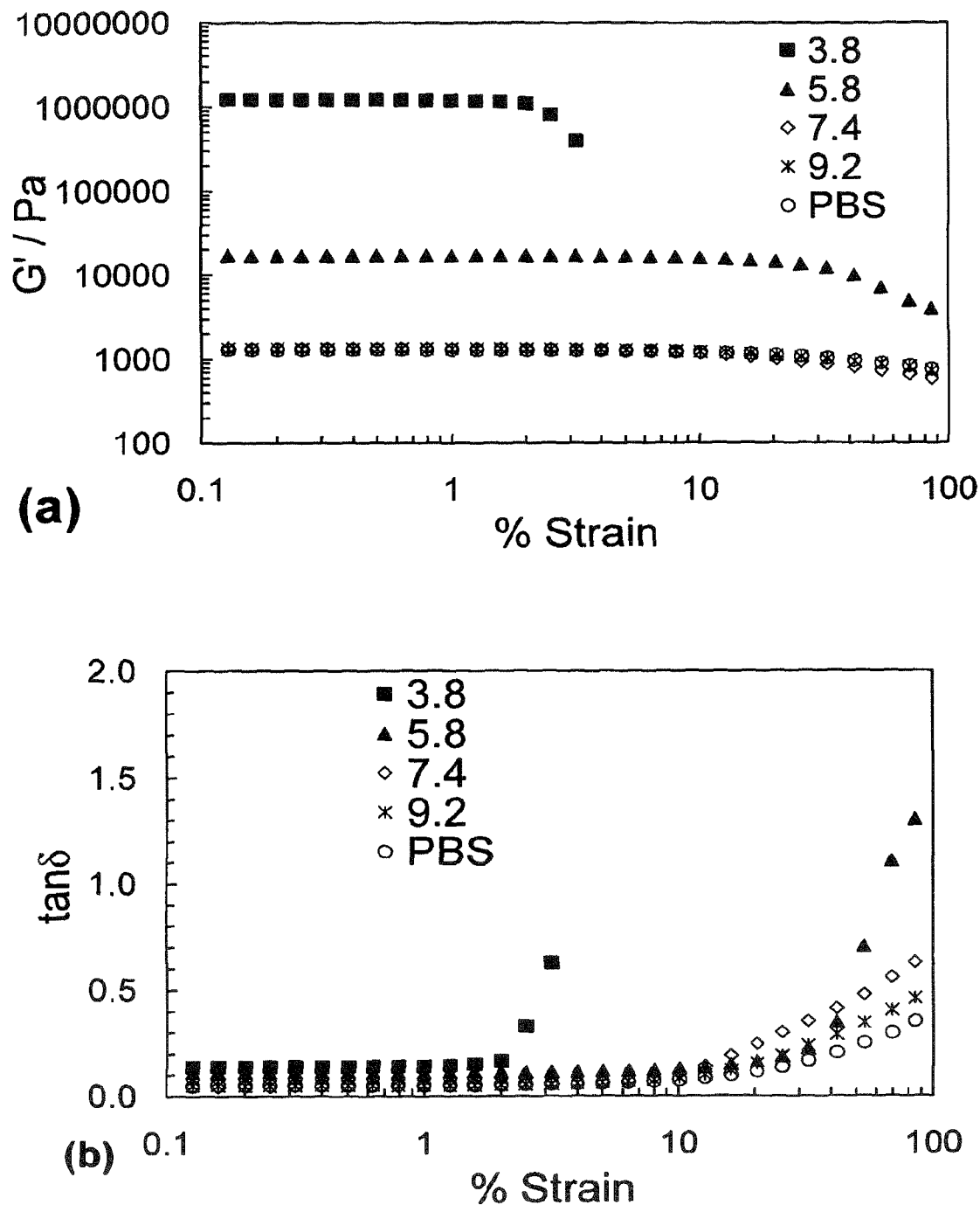

The $Q_{DX}$ values for the DX microgels was measured as a function of time (FIG. 12A).

FIG. 12A. shows (a) Swelling ratios as a function of time for DX GM-M-EGD prepared using $\phi_p$=0.08. The lines are guides to the eye. (b) Variation of swelling ratios measured after 8 days with pH for the DX GM-M-EGD (solid squares), DX GM-EGD(PBS) (open squares) and SX GM-M-EGD (open diamonds—this is product of method 3A, parent microgel) microgels. The initial pH was 7.8. The equations used for these data were (1) and (2).

The swelling was slow due to the close packed nature of these doubly crosslinked gels. We hypothesised that a close packed arrangement of particles was a requirement for preparing load supporting gels. The DX microgels of Cho et al.[8] were formed by a different process (attractive interactions) and had much faster swelling kinetics due to their more open morphology. The data shown in FIG. 12A reveals a significant difference between the $Q_{DX}$ values and the Q values for the SX GM-M-EGD microgels. The cause of the increased swelling for the DX GM-M-EGD microgels must be increased swelling between particles, i.e., a lower inter-particle crosslink density. This would suggest a higher $M_c$ at the particle periphery (linking particles) than in the particle interior. This would seem reasonable given (a) the low GMA functionalisation (1.8 mol. %) for the DX GM-M-EGD microgel and (b) the fragmentation that occurred for this system when swollen by water.

FIG. 12A.1 shows swelling ratios for (a) DX GM-M-EGD and DX GM(H)-M-EGD microgels as well as (b) DX GM-E-BDD microgel as a function of time measured at different pH values. The lines are guides to the eye. The DX microgels swelled in buffer solutions when the pH was greater than or equal to 7.4 and gave robust gels that did not fragment. The DX microgels required at least 1 day to reach full swelling. This is support for a space-filling morphology that is free of significant microporosity and is consistent with the SEM images (FIG. 10A). This slower swelling is different to the rapid swelling (minutes) observed for DX microgels prepared by a bridging aggregation. We suggest that the pore-free morphology (on the micrometer scale) of our DX microgels contributes to their high values of G'.

As a final study the rheological behaviours of the equilibrium swollen DX gels were probed (FIG. 12A-1). We selected DX microgels prepared at fairly low $\phi_p$ values in order to obtain high swelling ratios. Strain amplitude data appear in FIG. 12A-2. The gels used for this figure were those from FIG. 12A.

FIG. 12A-1 shows (a) Variation of G' and tan δ with pH for DX GM-M-EGD microgels. Triangles and diamonds are G' and tan δ, respectively. The closed symbols show data points obtained using PBS. (b) Variation of γ* with pH for the DX microges. The double crosslinking was performed using $\phi_p$=0.08 (pH=7.8) and the samples were swollen at the pH values shown for 8 days prior to measurement.

FIG. 12A-2 shows variation of (a) G' and (b) tan δ with strain for DX GM-M-EGD microgels after swelling at different pH values (or in phosphate buffered saline, PBS)

for 8 days. The frequency used was 1 Hz. The swelling ratios for theses DX microgels are shown in FIG. 12A-1.

Interestingly, the G' values reached ca. $10^6$ Pa at the lowest pH (of 3.8). This process of enhancing G' began once the pH was decreased to less than or equal to 5.8. A decrease in the value for $M_c$ occurs as the pH decreases. Hydrogen bonding between nearby RCOOH groups may also contribute to decreasing $M_c$. At pH=3.8 the DX microgel was brittle and γ* value decreased to about 2% (FIG. 10(*b*)). At pH=7.4 these DX microgels contain about 98% water at swelling equilibrium and have a modulus of about $10^3$ Pa with γ* of 8.4%. These values may suitable for potential application as injectable dispersions for soft tissue repair. Tunability of these properties should be achievable through the $\phi_p$ value used during DX microgel formation and also through monomer selection.

(ii) Variation of (a) G' and (b) Tan δ with Strain for Cross-Linked Microgels Prepared.

The following equation, which originates from rubber elasticity theory, can be used to describe the modulus of a network[20,21].

$$G \cong \frac{\rho RT}{M_c} \qquad (7)$$

For equation (7) G is the shear modulus, ρ is the density of the polymer, R and T have their usual meanings and $M_c$ is the number average molecular weight between crosslinks. The latter is the molecular weight of the elastically effective chains. The value for G' should increase with decreasing $M_c$. This will have two contributions from DX microgels; intra-particle and inter-particle crosslinks.

Figures 1, 14A:
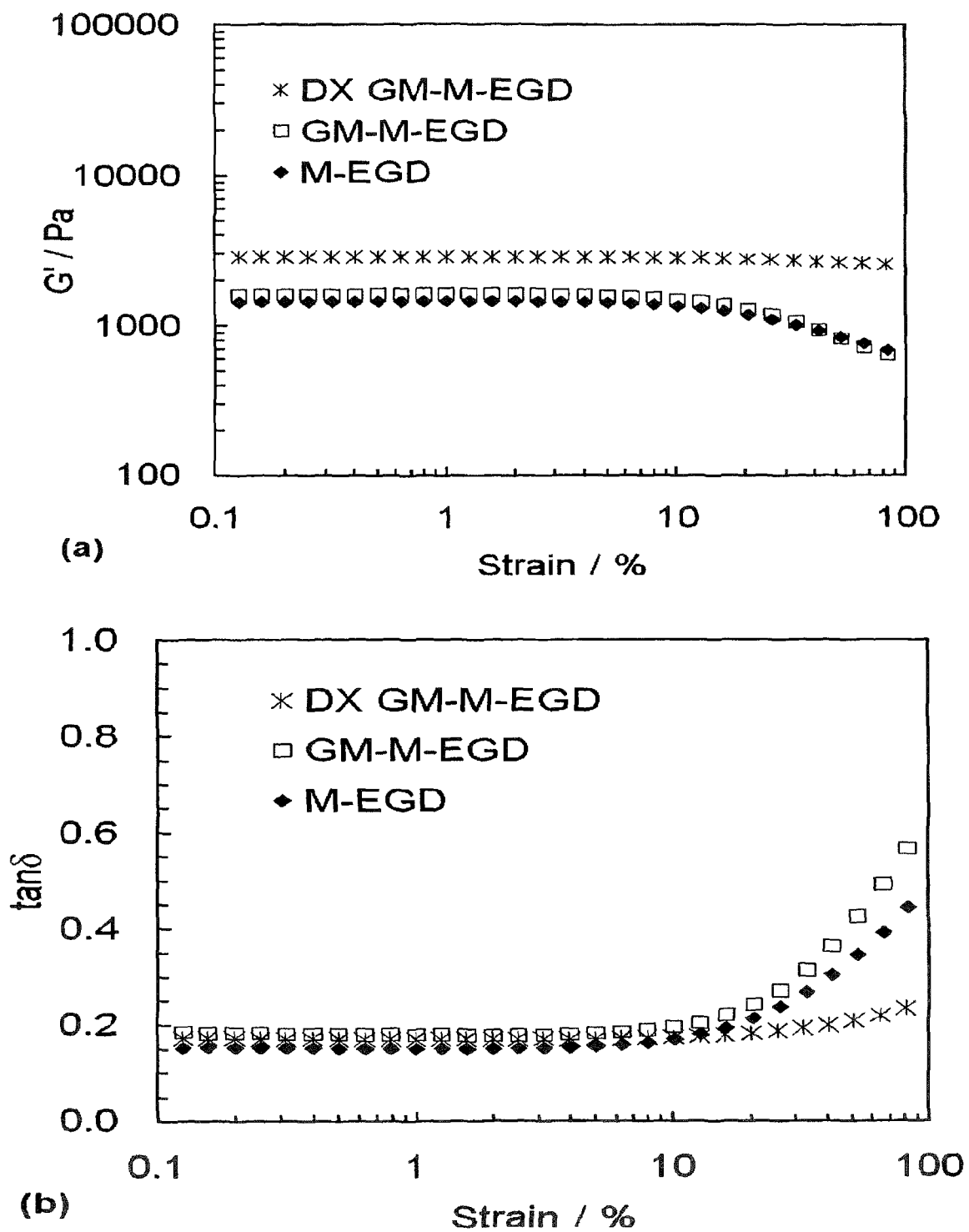
Figures 1, 14A:
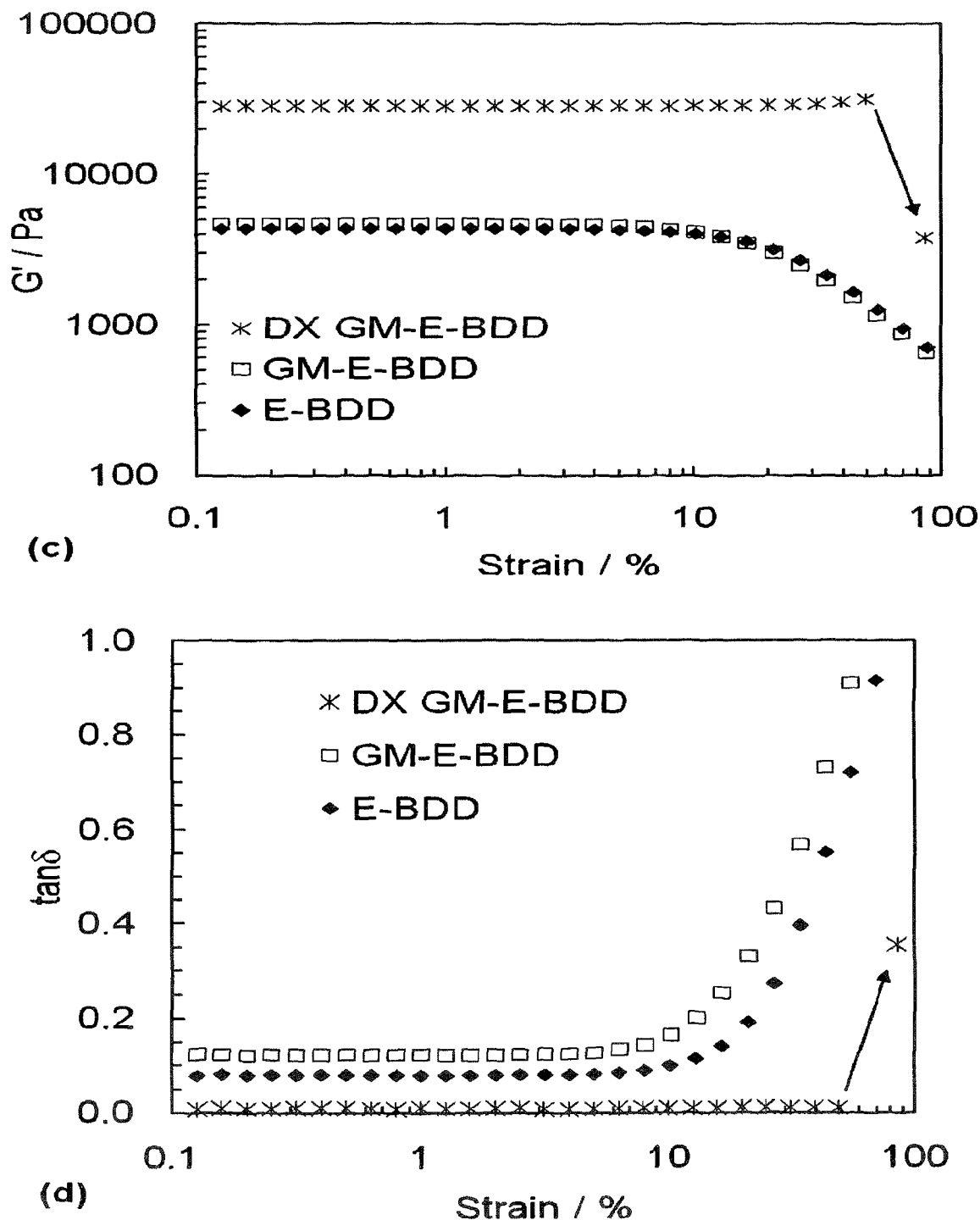
Figures 2, 14A:
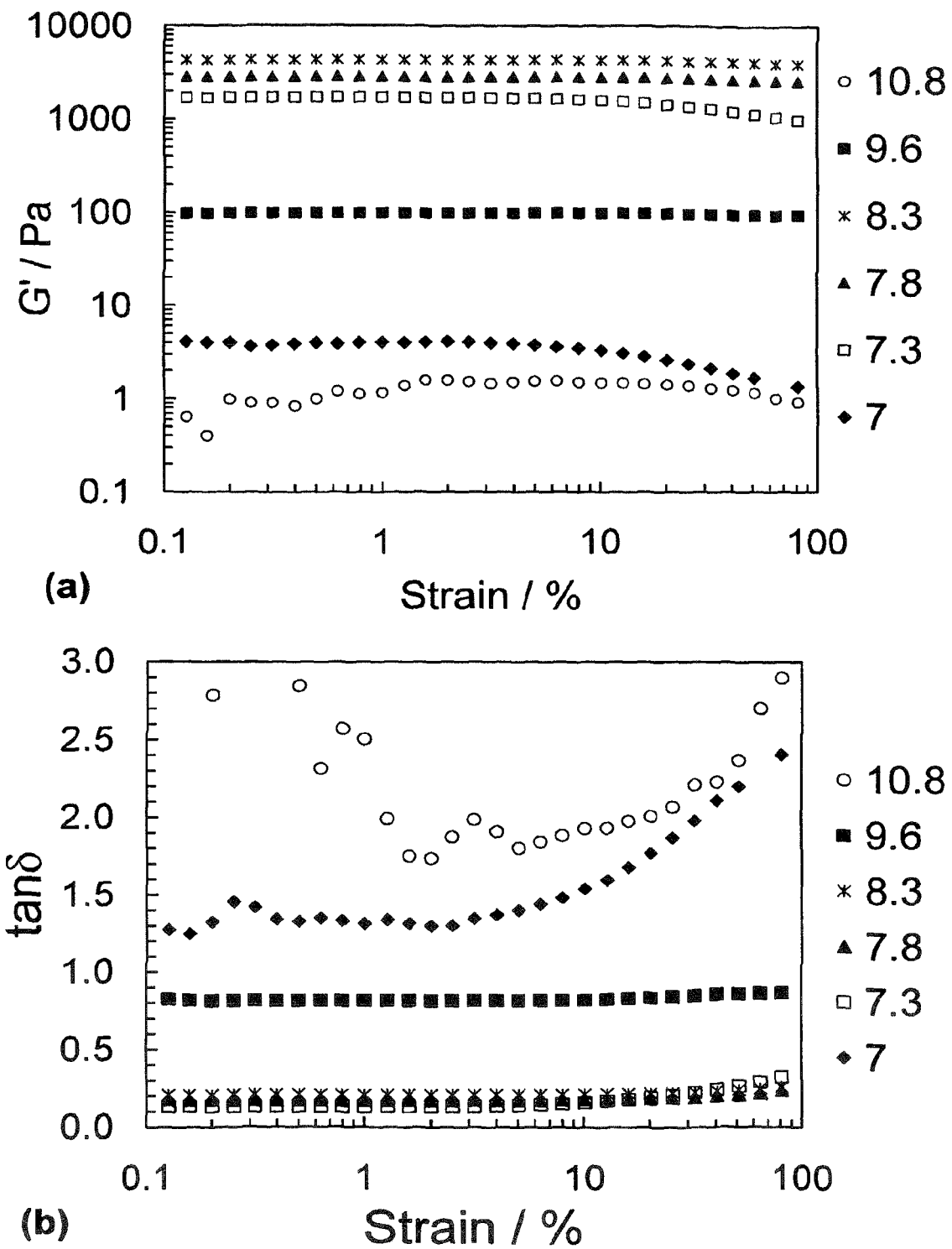
Figures 3, 14A:
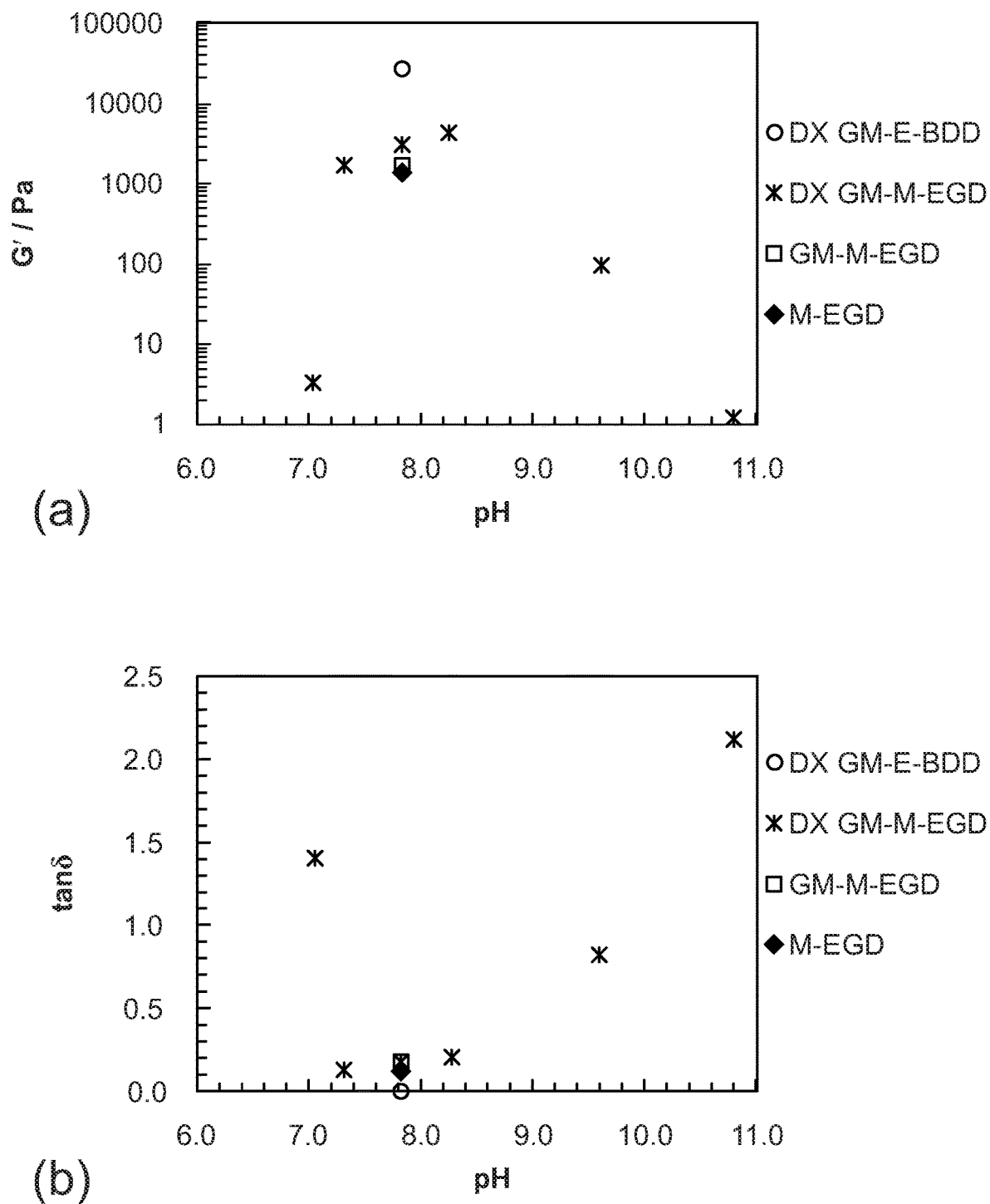
Figures 3, 14A:
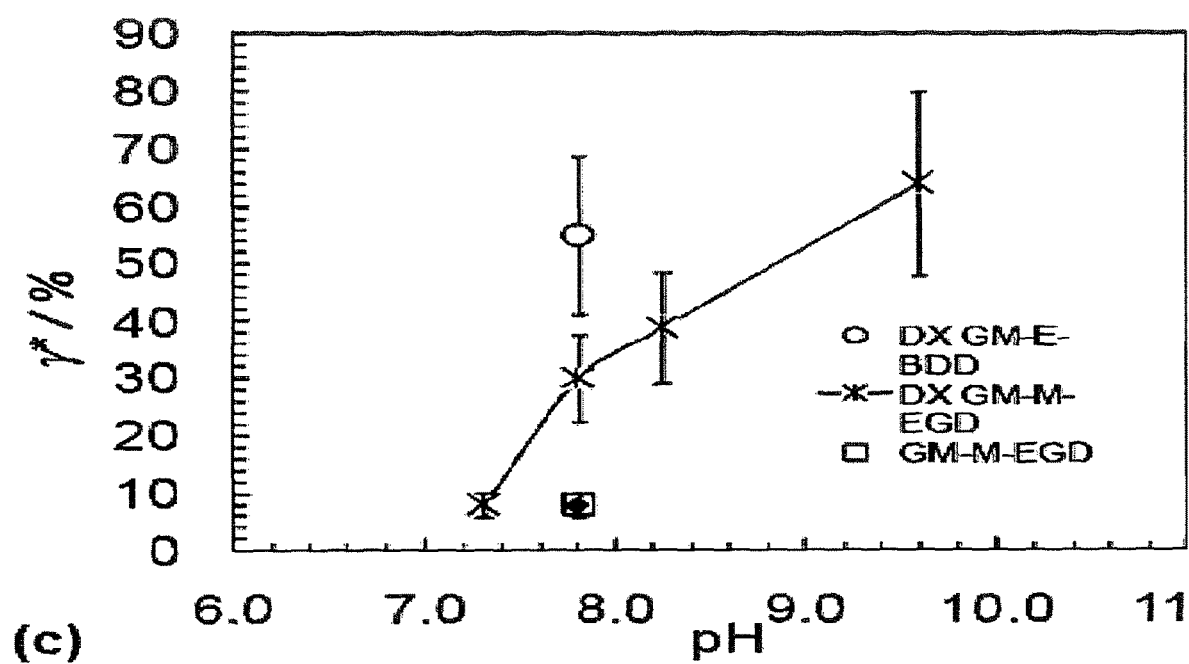

Dynamic rheology was used to investigate the mechanical properties of the DX gels. Strain amplitude data are shown in FIG. 14A-1. These data consist of the two parent SX physical gels (M-EGD or E-BDD and GM-M-EGD or GM-E-BDD) and the respective DX microgels (DX GM-M-EGD or DX GM-E-BDD). FIG. 14A-1 shows a comparison of strain amplitude measurements for DX and SX microgels based on M-EGD ((a) and (b)) and E-BDD ((c) and (d)). The data were obtained at the same particle volume fraction (0.10) and pH (7.8). The frequency used was 1 Hz. The arrows in (c) and (d) show the abrupt change in the G' and tan δ values that occurred.

It can be seen that a slight increase in G' occurred for both of the GM functionalised physical gels compared to the respective parent microgel. This is attributed to the greater hydrophobicity of GM functionalised microgels. Importantly, there is a major increase in G' upon double cross-linking. Moreover, the tendencies for the G' values (FIGS. (14A-1(*a*) and (*c*)) to decrease and tan δ values (FIGS. 14A-1(*b*) and (*d*)) to increase at high strain are greatly diminished as a consequence of double crosslinking. Both of these behaviours are indirect evidence for inter-particle crosslinking.

It can be seen from FIG. 14A-1(*d*) that the tan δ values are exceptionally low for DX GM-E-BDD microgel with an average tan δ of ca. 0.01. That means that the energy loss from dissipation was less than 1% of the energy stored in this DX microgel network. The mechanical properties of the DX GM-E-BDD microgel were almost completely elastic. Interestingly, this DX microgel does not show strain-induced network breakdown until the strain reaches 50% (FIG. 14A-1(*c*)). All of the microgels studied here generally satisfy one key criterion to be considered as gels[22,23], i.e., tan δ<1.0. However, for the DX GM-E-BDD microgel tan δ is also independent of frequency, which is a second criterion that many gels do not satisfy.

FIG. 14A-.1.1 shows strain amplitude ((a) and (b)) and frequency sweep ((c) and (d)) dynamic rheology data for DX GM(H)-M-EGD, DX GM-E-BDD and DX GM-M-EGD microgels, where the DX microgels were prepared at $\phi_p$=0.10 and pH=7.8.

It was expected that $M_c$ would be inversely proportional to the degree of functionalisation. Therefore, G' was expected to increase with functionalisation according to equation (7). This was investigated using DX GM-M-EGD and DX GM(H)-M-EGD microgels. The latter had a higher GM functionalisation (5.8 mol. % cf. 1.8 mol. %). Strain amplitude and frequency sweep rheology data for the DX GM(H)-M-EGD and GM-M-EGD microgels are shown in FIG. 14A-1.1. Comparing the data shown in FIGS. 14A-1.1 (*a*) and (*b*) it is clear that the G' values for DX GM(H)-M-EGD are much higher than those for DX GM-M-EGD. At a strain of 1% the value of G' for DX GM(H)-M-EGD was 18,800 Pa, and is six times the value for DX GM-M-EGD. This is a high modulus for a gel that only occupies 10 vol. % of the total volume. Furthermore, the value for tan δ decreased to 0.045. The frequency dependence of G' and also tan δ greatly decreased (FIGS. 14A-1.1 (*c*) and (*d*)). The DX GM(H)-M-EGD microgel is less ductile as tan δ increases more at a lower strain (FIG. 14A-1.1 (*b*)). The value of γ* is 8.0%. All of these changes are indicative of a smaller $M_c$ value as a consequence of a higher degree of GM functionalisation for DX GM(H)-M-EGD. The changes for G' and γ* for this system generally match what is expected for a conventional hydrogel and we attribute these changes to increased inter-particle crosslinking. These data show that the modulus and ductility for the DX GM-M-EGD microgels are tuneable using the extent of GM functionalisation.

(iii) Variation of (a) G' and Tan δ as Well as (b) γ* with Microgel Particle Volume Fraction for Doubly Cross-Linked Microgels of Example 4

The effect of GM-M-EGD volume fraction used during double crosslinking was also investigated.

Figure 16:
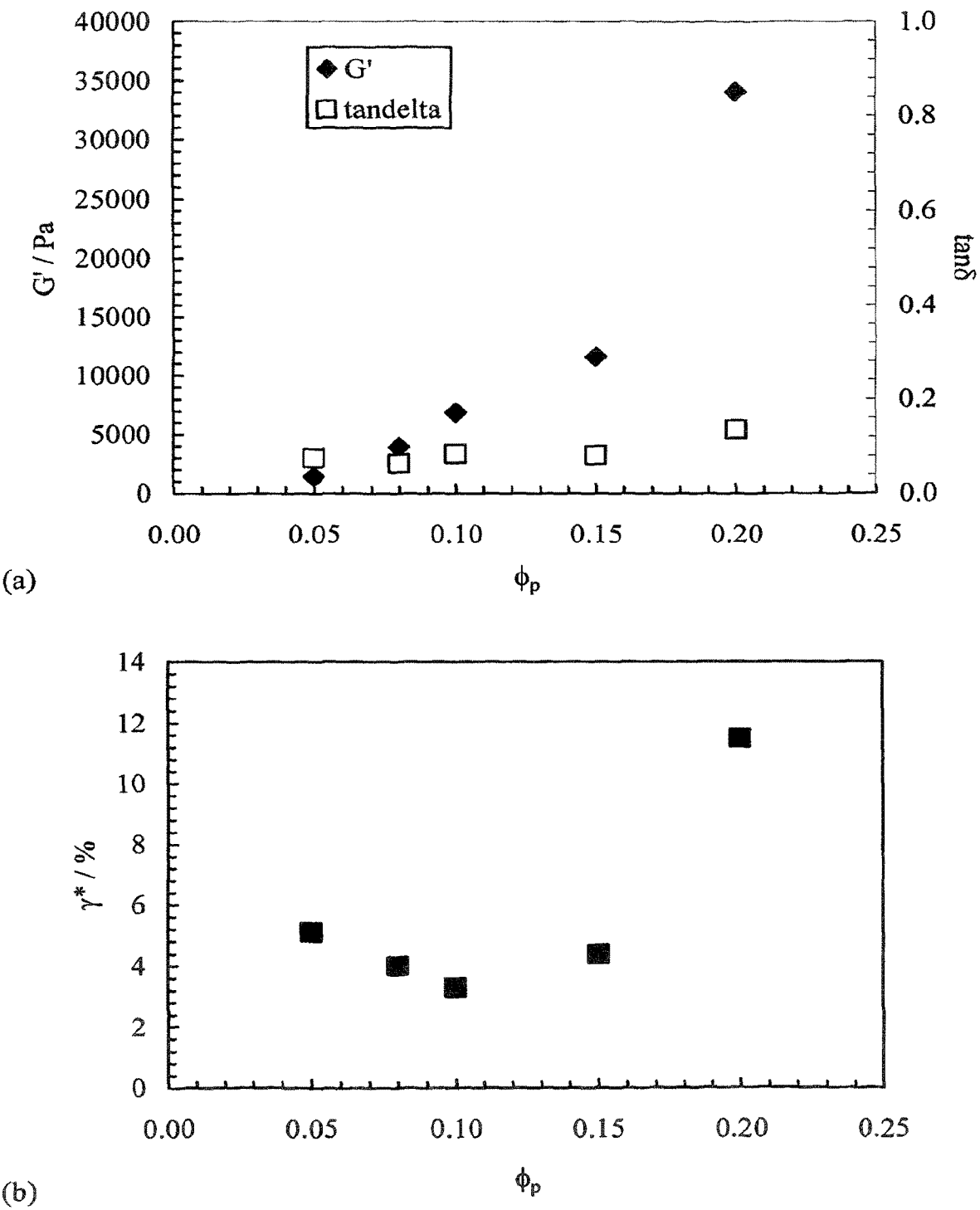
Figure 16A:
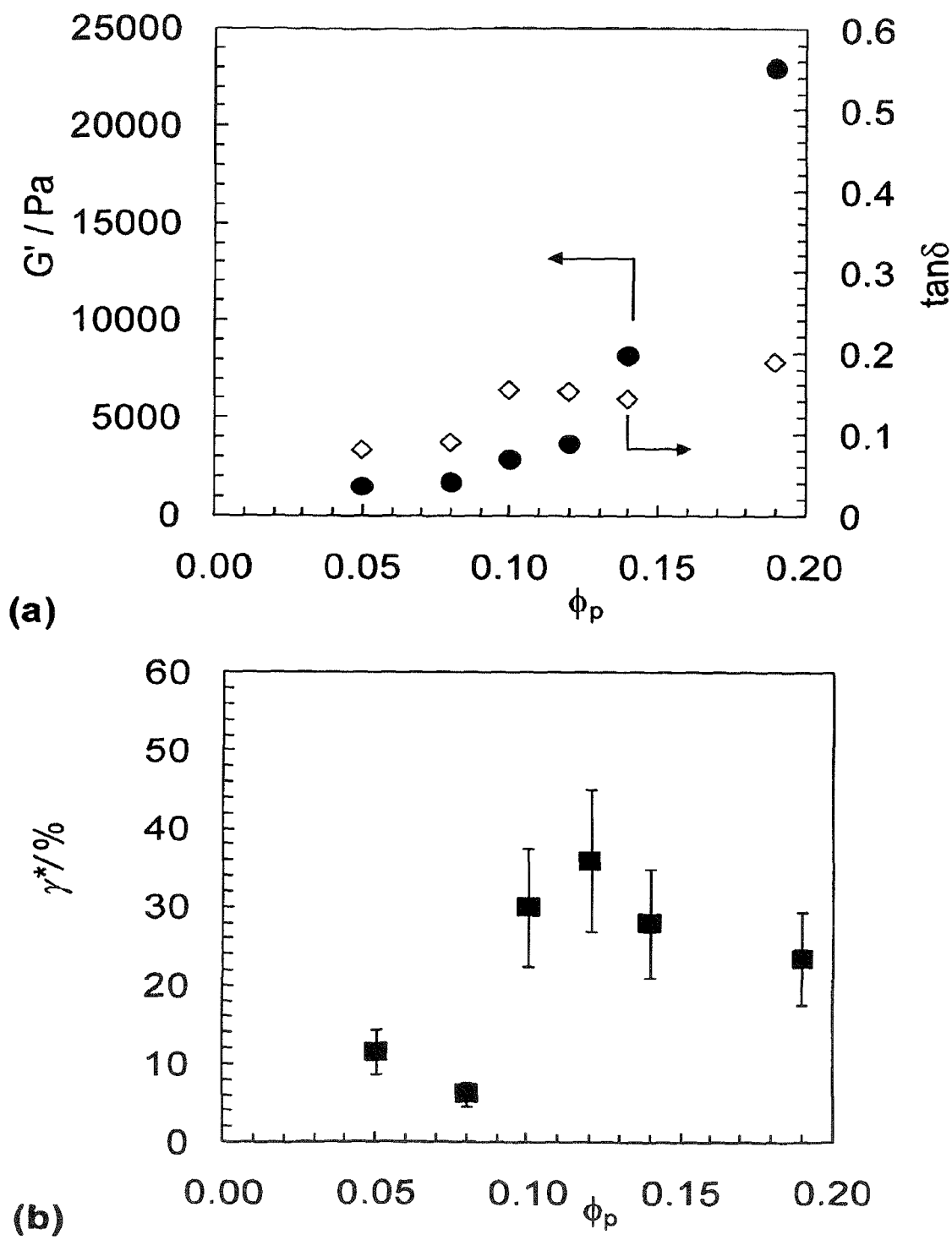

FIG. 16A shows (a) Effect of GM-M-EGD volume fraction used during double crosslinking on G' and tan δ. (b) The variation of γ* with volume fraction of polymer. The pH used to obtain these data was 7.8. A strain and frequency of 1% and 1 Hz was used to obtain the data shown in (a).

The data show an increase of G' with $\phi_p$. Furthermore, tan δ increases with $\phi_p$ which suggests an increase in dissipation with high microgel concentrations. FIG. 16A(a) shows an increase for G' when $\phi_p$ reaches 0.10. FIG. 16A(b) shows that that γ* increases strongly when $\phi_p$ reaches 0.10. These data suggest a critical $\phi_p$ value of about 0.10 where the inter-particle crosslinking becomes increasingly pronounced. Presumably, higher $\phi_p$ values result in more extensive interpenetration at the periphery of the particles. These data show that the G' of the DX microgel can be readily tuned simply by using microgel particle concentration.

(iv) Variation of (a) G' and Tan δ as Well as (b) γ* with pH Used During Cross-Linking in Example 4.

The effect of pH used during double crosslinking was investigated. A particle concentration of $\phi_p$=0.10 was used for these experiments. We first consider data from strain amplitude experiments (FIG. 14A-2).

FIG. 14A-2 shows strain amplitude data for DX GM-M-EGD microgels prepared and measured at different pH values (shown in legend). The value for $\phi_p$ was 0.10. The data plotted were obtained using 1 Hz.

It can be seen that G' does not change significantly with strain (γ) over the strain range of 0.1 to 10% for pH values between 7.3 and 8.3. It does, however, begin to decrease at higher strain values. These data show that increasing the pH during preparation (up to 8.3) both increases G' and also the strain required to disrupt the network. Beyond a pH of 8.3 both parameters then decrease. When the pH was greater than or equal to 9.6 tan δ is greater than 1.0 and the material remains fluid.

FIG. 14A-3 shows data taken from mechanical spectra (average of strain and frequency sweeps). Note for (c) that only data for the gels (tan δ<1.0) are shown. Data used are 1% strain and 1 Hz. The vertical lines shown in (a) and (b) are the $pK_a$ value for GM-M-EGD. The curve in (c) is a guide for the eye.

It can be seen from FIG. 14A-3 that the G' values increased by approximately factors of 2 and 7, respectively for the DX GM-M-EGD and GM-E-BDD microgels. This implies that $M_c$ decreased by a factor of 2 for the DX GM-M-EGD. For the DX GM-E-BDD series $M_c$ must have decreased by a factor of about 7. These data changes are generally consistent with equation (3) because the former should have a much lower $M_c$ due to the much higher mol. % of GMA incorporated (Table 1).

The yield strain (γ*) is defined here as the strain at which G' decreases to 95% of its value at 1% strain[24]. This increases from about 8% for the SX gels (FIG. 14A-3(c)) to greater than 30% for the DX GM-M-EGD gel and 55% for the DX GM-E-BDD gel. The increase in this value is an indication of relatively flexible chains linking the microgels together. This could be due to extended chains of the particles at the periphery which have interpenetrated and crosslinked with chains from neighbouring particles.

Physical gels must first form in order for a covalently linked microgel network to subsequently form. It can be seen from FIG. 14A-3 that the DX microgels with the highest G' and lowest tan δ values occur at pH values between 7.3 and 8.3. Indeed, in this pH range (which includes physiological pH) both G' and γ* increase with pH used to prepare the DX microgels. At higher pH values γ* increased (FIG. 14A-3(c)); however, G' decreased and tan δ increased to above 1.0 indicating that a fluid is present. This is suggestive of an increased molar mass between crosslinking points at the particle periphery. At high pH values this becomes insufficient to enable gel formation.

The value for γ* will be sensitive to both the $M_c$ values within and between the microgel particles. The increase for γ* with pH for the DX GM-M-EGD microgels (FIG. 14A-3(c)) suggests that longer elastically effective chains are present at the particle periphery at high pH. At pH=9.6 the gel was approaching the fluid state (tan δ approaching 1.0). The G' value was low (96 Pa). However, that system had the highest γ* value of 64%. Moreover, that sample was completely transparent (without turbidity). At higher pH values the dispersions did not form physical or covalently-linked gels. It is likely that electrolyte triggered particle collapse at high pH (due to screening) reduced the extent of particle inter-penetration to the point where physical gelation did not occur.

Conclusions

In this work a new general method for preparing DX microgels has been demonstrated. This method uses only functionalised microgels and has been used to prepare two new families of pH responsive DX microgels; DX GM-M-EGD and DX GM-E-BDD. These DX microgels did not re-disperse in 0.1 M buffer solutions in the pH range of 3.8 to 9.2 or PBS (0.15 M). The mechanical properties of the as-made DX gels are strongly dependent on pH and also $\phi_p$ used for preparation. This offers considerable opportunity for tuning these properties for specific applications, e.g., for soft tissue repair and or load support. This study has shown that the modulus and yield strain can be controlled using preparation conditions.

The mechanical properties of the DX microgels appear to be strongly determined by those of the parent microgel and also the degree of functionalisation. The data reveal that high modulus of the physical gels will lead to high modulus values for the respective DX microgel. However, the extent of increase of the modulus on double crosslinking increases with the mol. % of GMA incorporated. The ductility of the microgels, as judged by γ*, is dependent on inter-particle crosslinking and increases considerably when a $\phi_p$ greater than or equal to 0.10 is used during DX preparation. The study has shown that injectable dispersions that can form DX microgels can be achieved using $\phi_p$=0.08. If high G' and yield strains are required, higher $\phi_p$ values should be used.

The DX GM-E-BDD microgel used in this study to demonstrate generality was shown to be remarkable in terms of its elastic properties. It was found to behave as a near perfect gel rheologically (tan δ approaching zero and invariant with frequency and high γ*) and exceptionally low viscous component. This could be an important new gel for soft tissue repair.

Example 5—Cross-Linking of the Vinyl-Grafted Microgel Particles

Two types of MAA-containing microgels were prepared in this work; M-EGD and E-BDD. The majority of the work was conducted on the M-EGD series because this system has greatest potential application in soft tissue repair. M-EGD contains co-monomers that have been investigated for application in bone cement (Hiratani, H.; Alvarez-Lorenzo, C. *Biomaterials* 2004, 25, 1105.) and contact lenses (Zhang, X. S.; Revell, P. A.; Evans, S. L.; Tuke, M. A.; Gregson, P. J. *J. Biomed. Mater. Res.* 1999, 46, 279). The principle monomer (MMA) is a major component of bone cement. The E-BDD microgels were used to demonstrate the generality of our new approach.

DX microgels were prepared using a volume fraction of polymer of $\phi_p$=0.10, pH=7.8 and in the presence of 22 mM of APS unless otherwise stated. The AEM-functionalised microgel (Microgel AEM10-M-EGD obtained from Method 3B) was added to a NaOH/APS solution and then vigorously mixing for about three minutes. After fully mixing the physically gelled dispersion was heated at 50° C. for 8 hours to produce DX AEM-M-EGD.

In the case of microgels investigated using rheology, the DX reaction was performed for at least 1 hour in the rheometer before the system was cooled to room temperature and the rheology experiments performed.

Figure 9B:
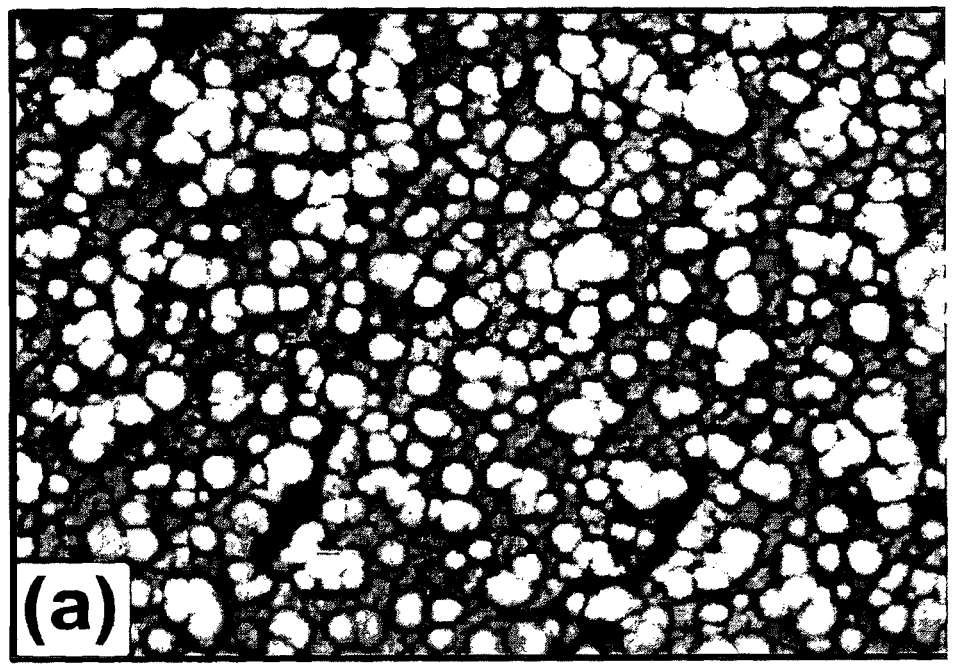
Figure 9B:
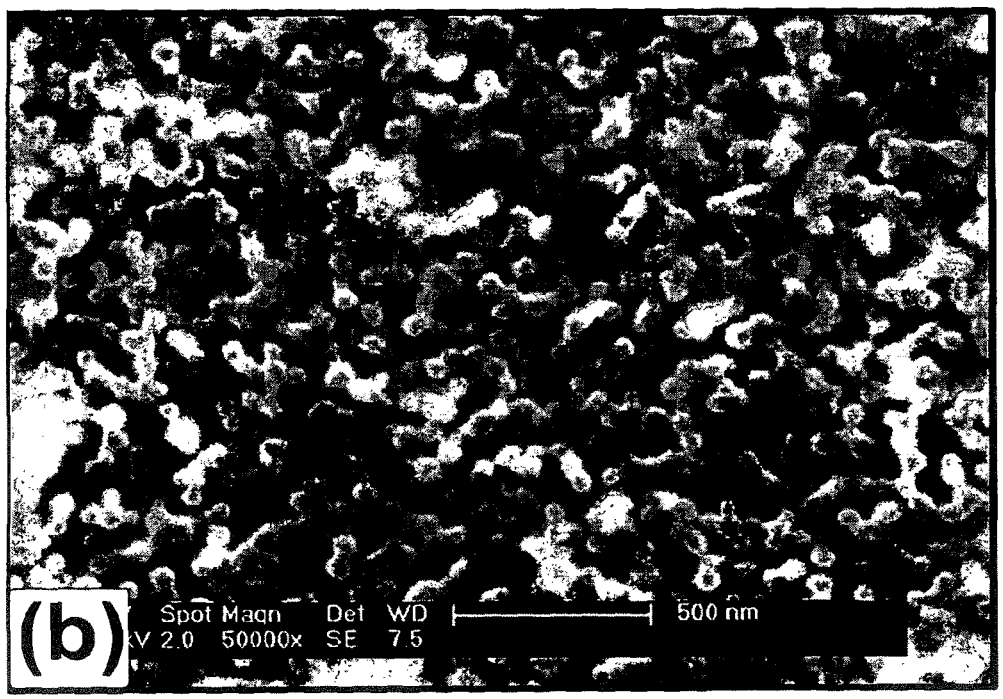
Figure 9C:
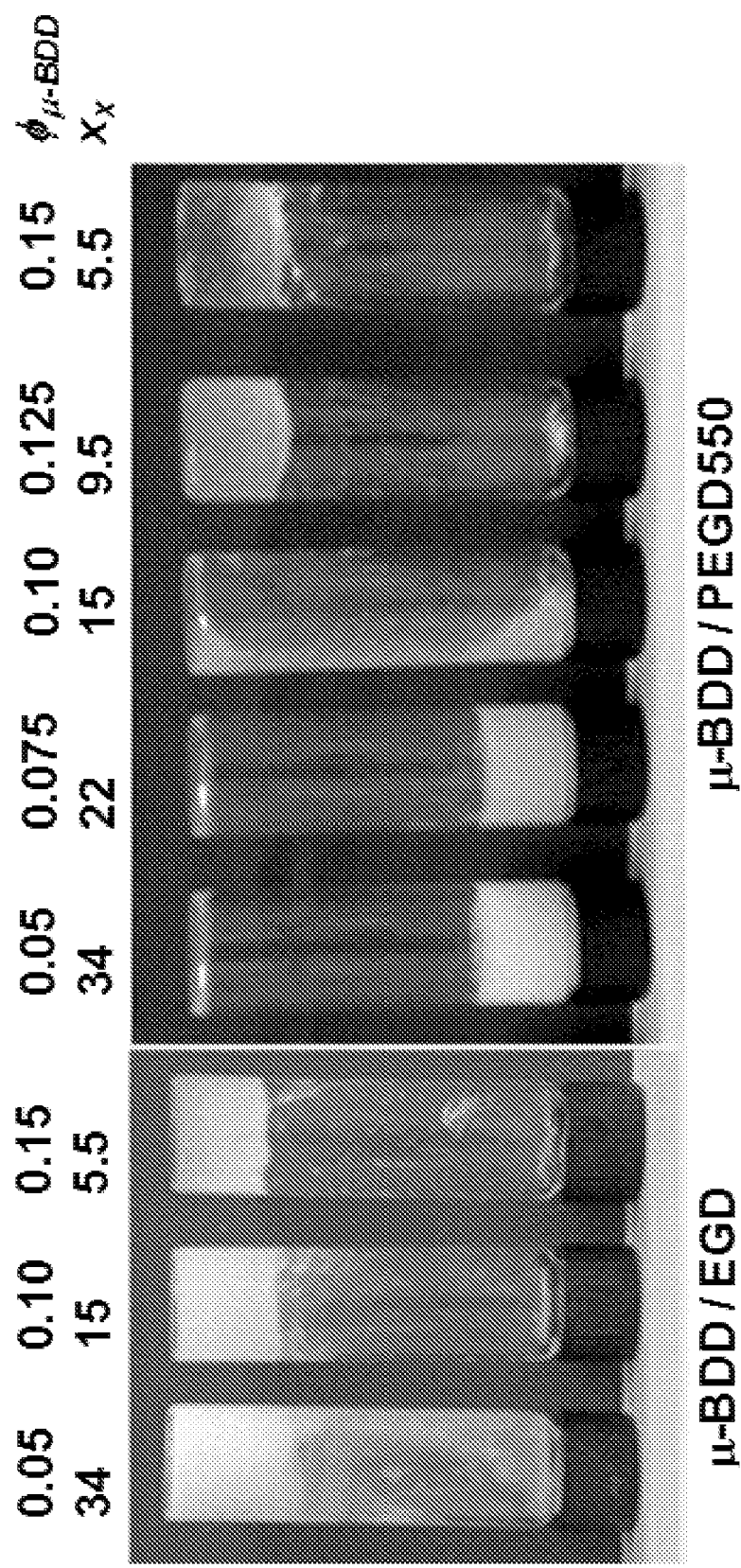

FIG. 9B shows an SEM photographic image of: (a) Microgel M-EGD (of Method 1A); (b) Microgel E-BDD (of Method 2A). Representative SEM images for the microgels are shown in FIG. 1. Spherical particles are evident.

Figure 10B:
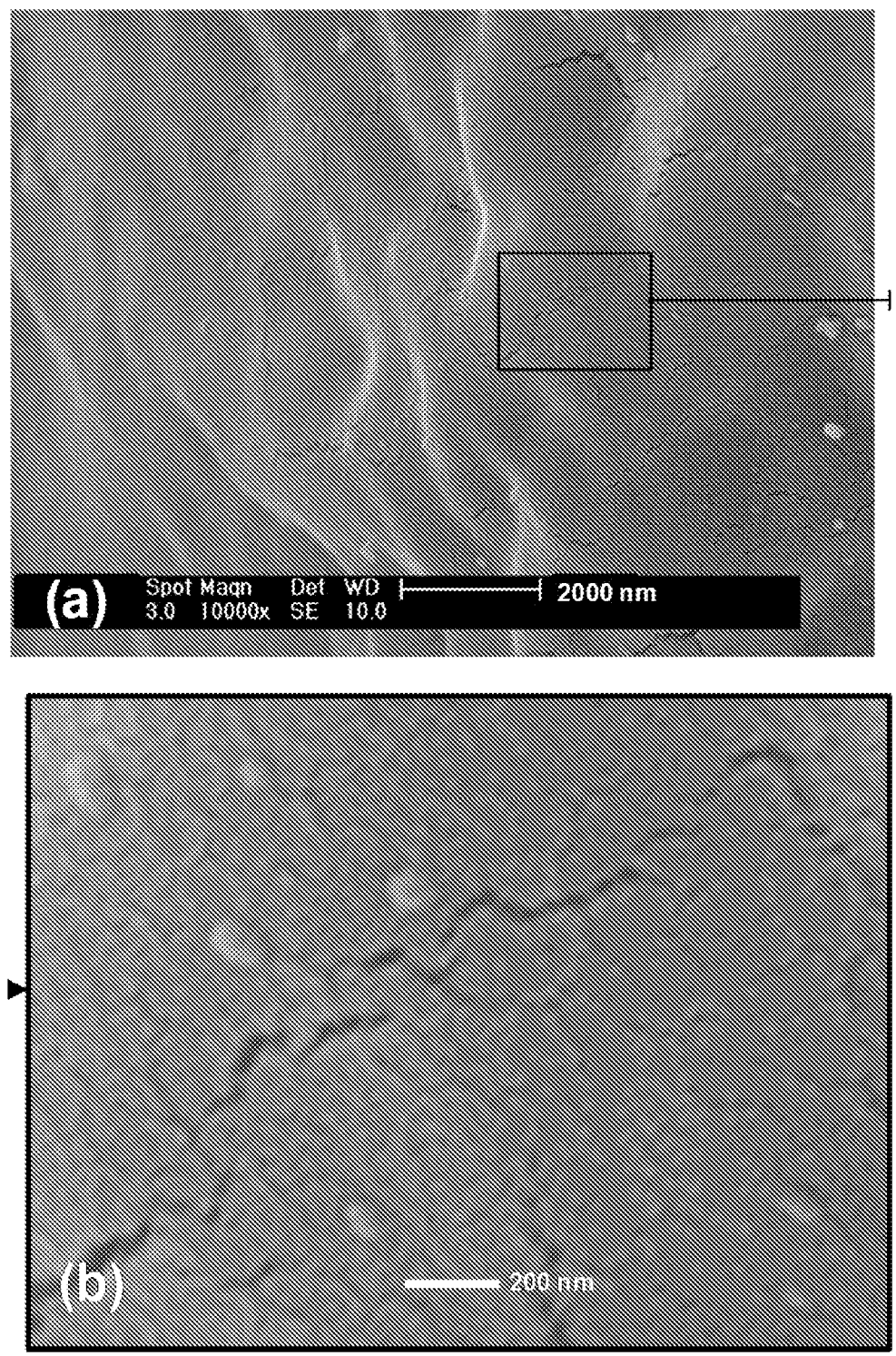

FIG. 10B shows scanning electron micrograph images of air-dried (at room temperature) samples of: (a) DX AEM-M-EGD and (b) DX AEM-M-EGD (blown up image from FIG. 10B(a)). The sample was prepared using $\phi_p$ ([AEM]/[MAA])=0.10 and pH=7.8. SEM image was obtained using a Philips FEGSEM instrument.

These samples were air dried (at RT) prior to SEM. They show evidence of micrometer and nanometer sized cracks. Interestingly, some microgel particles can be seen on the surface obtained using high magnification. The similarity of the size of the parent M-EGD microgel particles with the features surrounded by cracks in FIG. 10B(b) leads to the suggestion that cracks formed at the interfaces between neighbouring aggregates. If confirmed, this would indicate that the periphery between aggregates is the weakest point of the DX microgel matrix.

Characterisation (i) Variation of (a) G' and (b) Tan δ with Strain for Cross-Linked Microgels Prepared as Per Example 5.

The DX microgels were prepared from physically gelled microgels. Therefore, the rheological behaviour of the singly crosslinked microgel dispersions were studied at the same pH and $\phi_p$ values used for double crosslinking.

Figures 1, 14B:
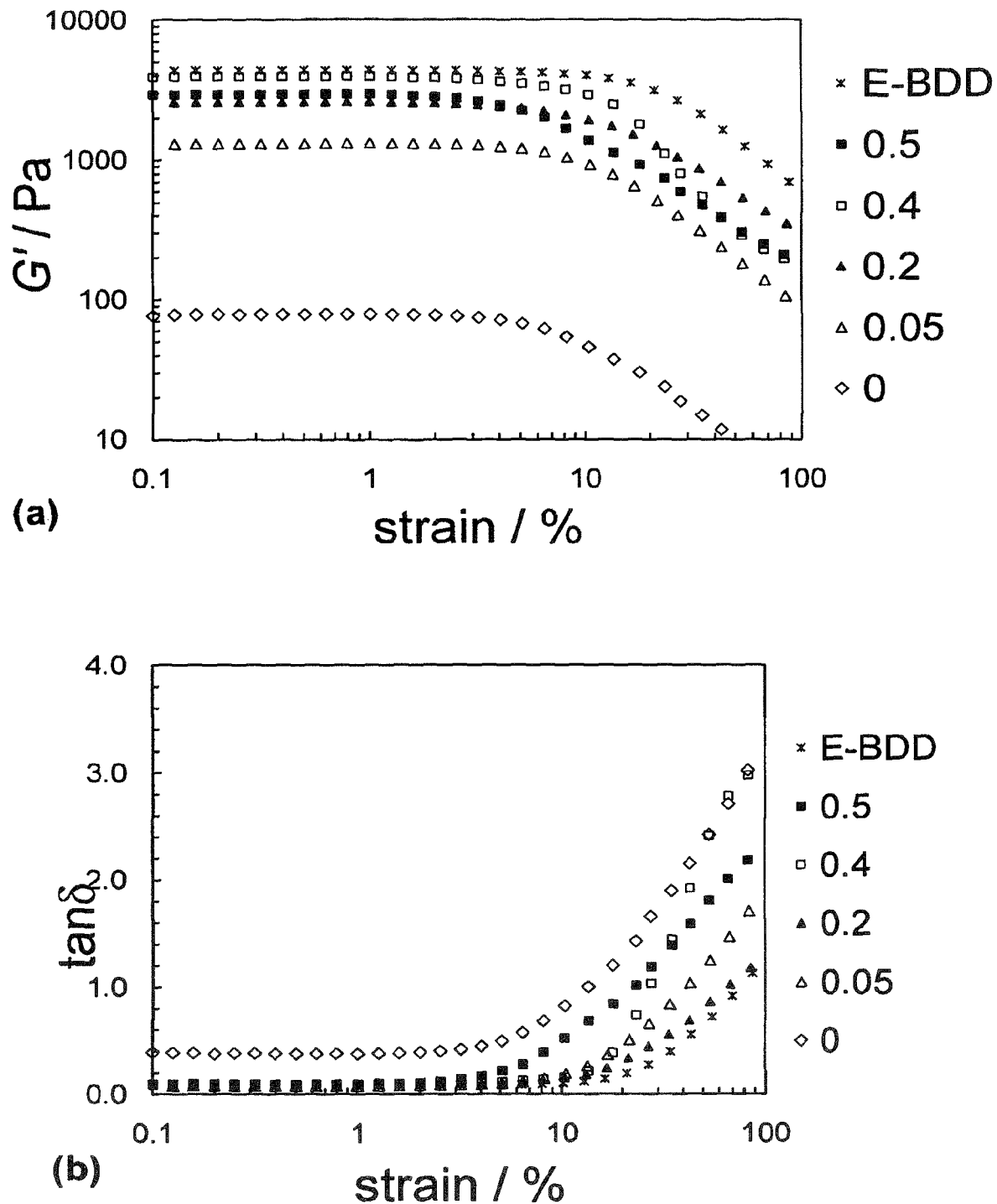
Figures 1, 14B:
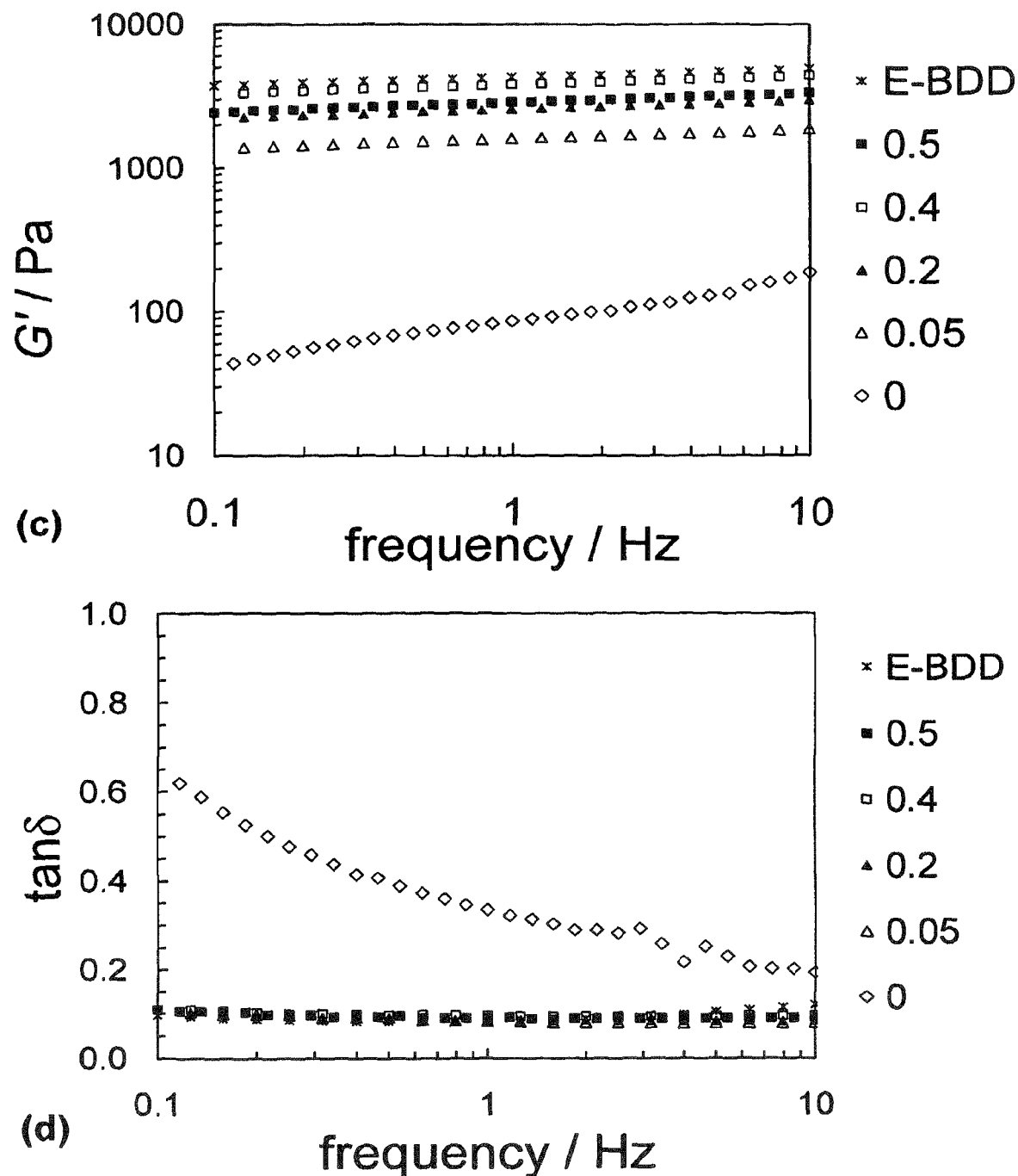
Figures 2, 14B:
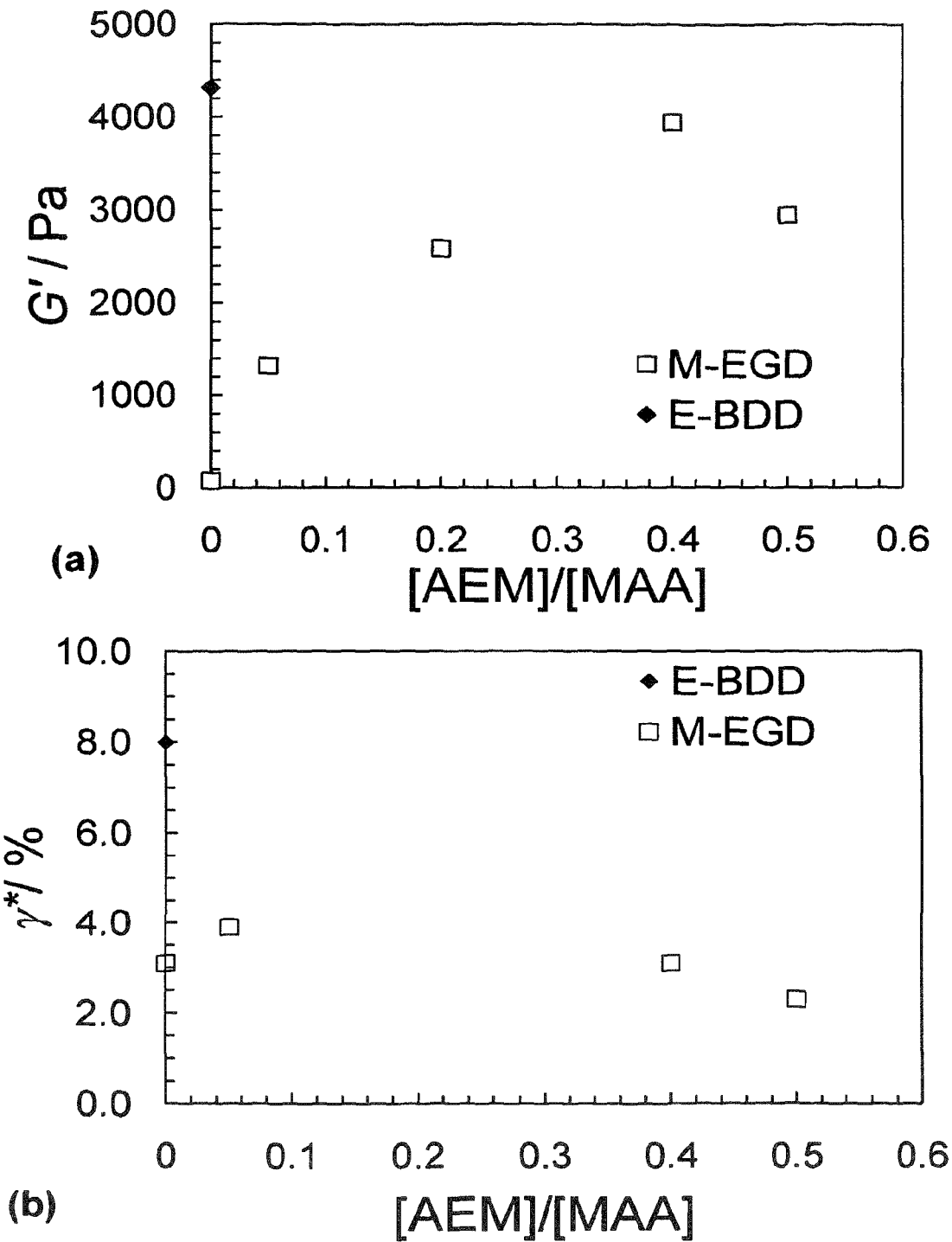
Figures 3, 14B:
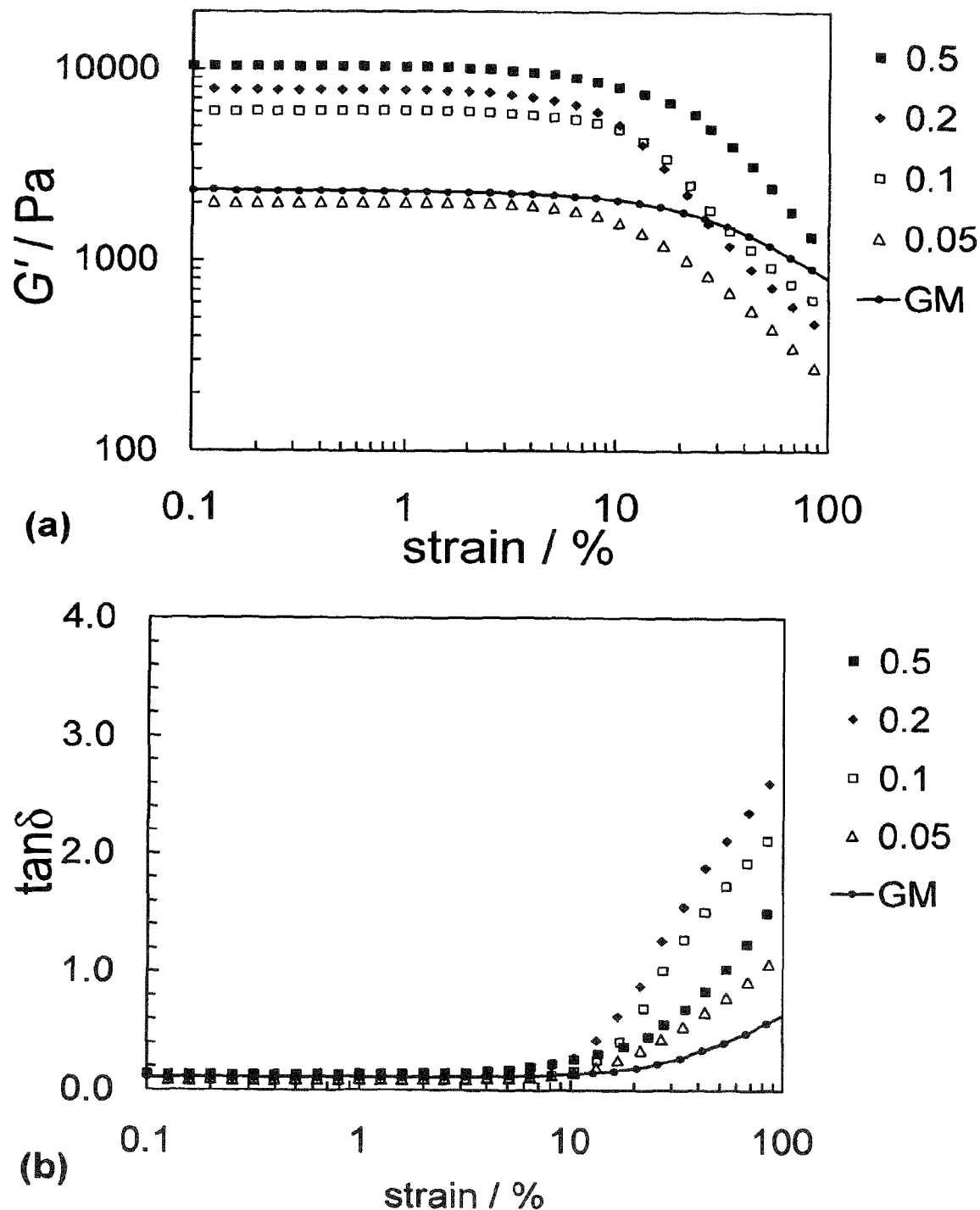
Figure 14B:
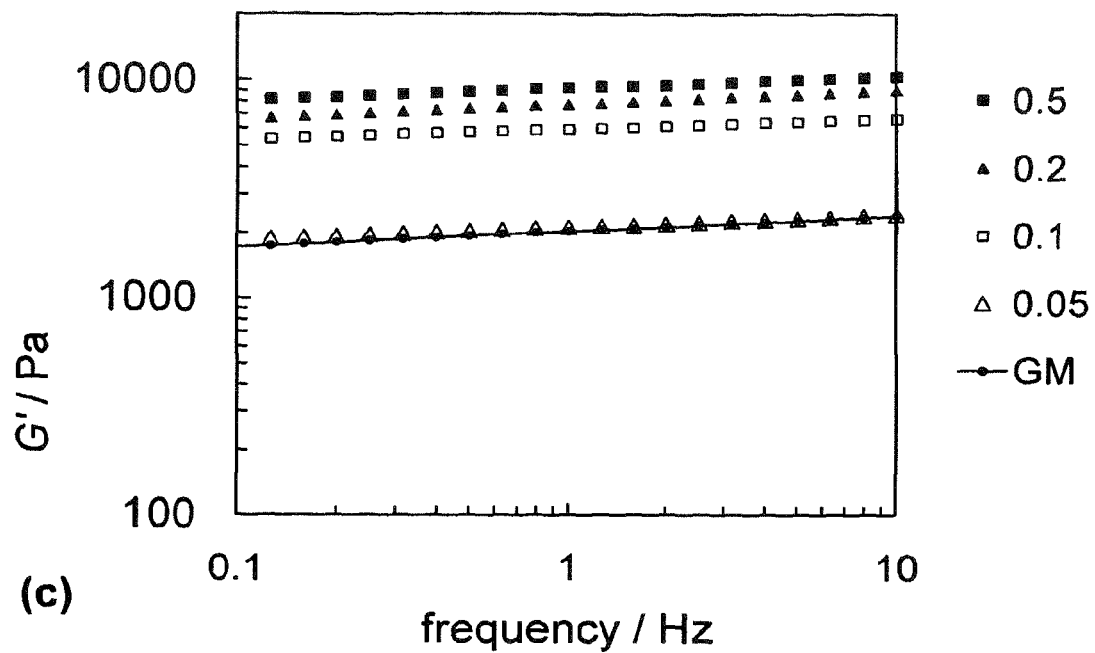
Figure 3:
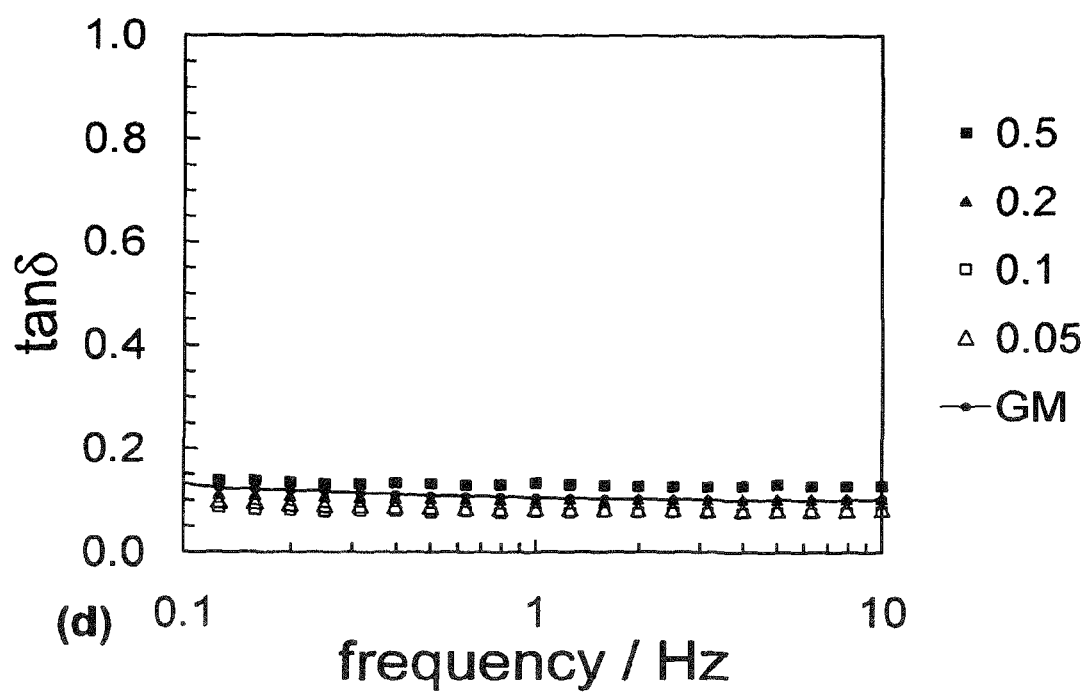
Figures 4, 14B:
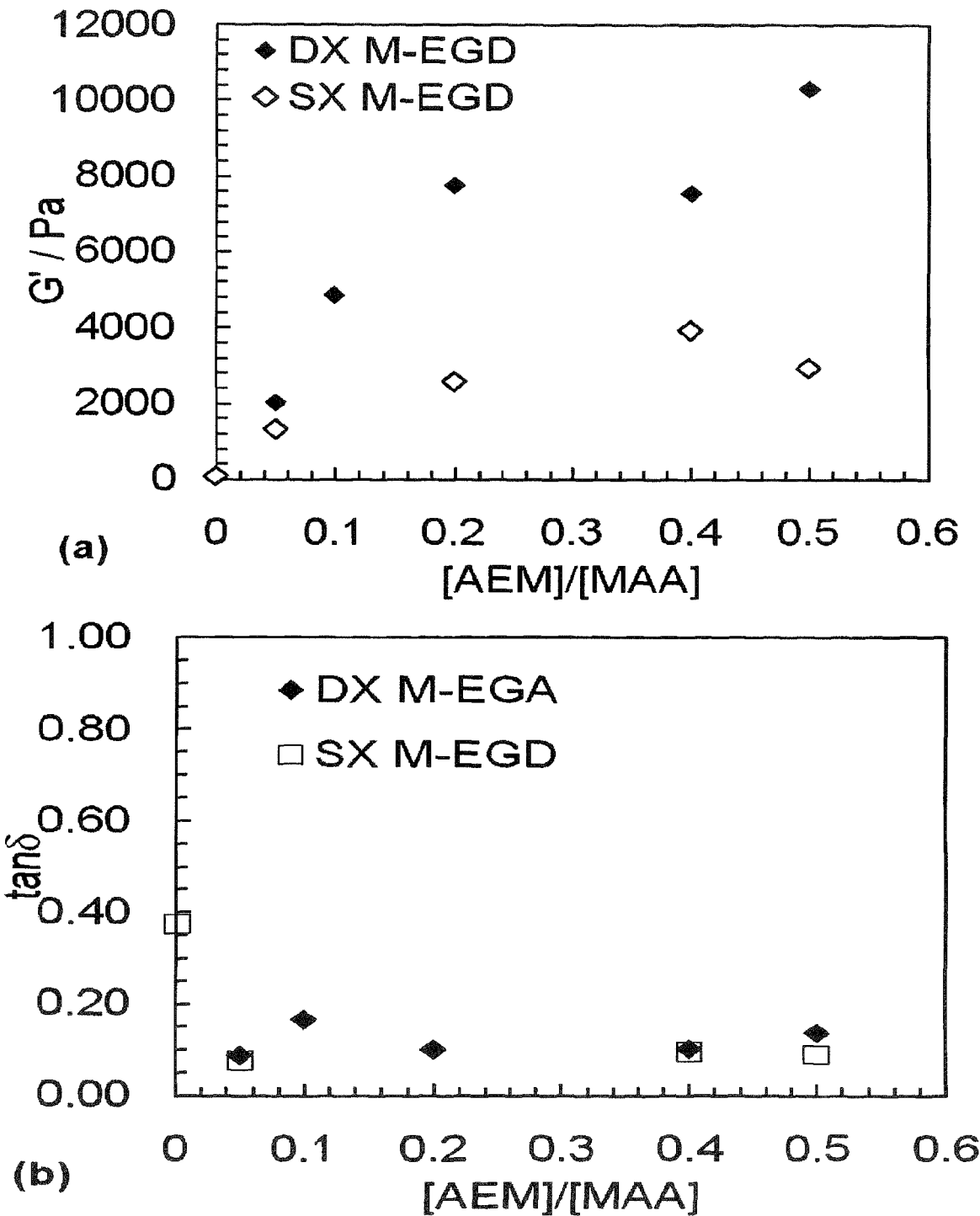
Figures 4, 14B:
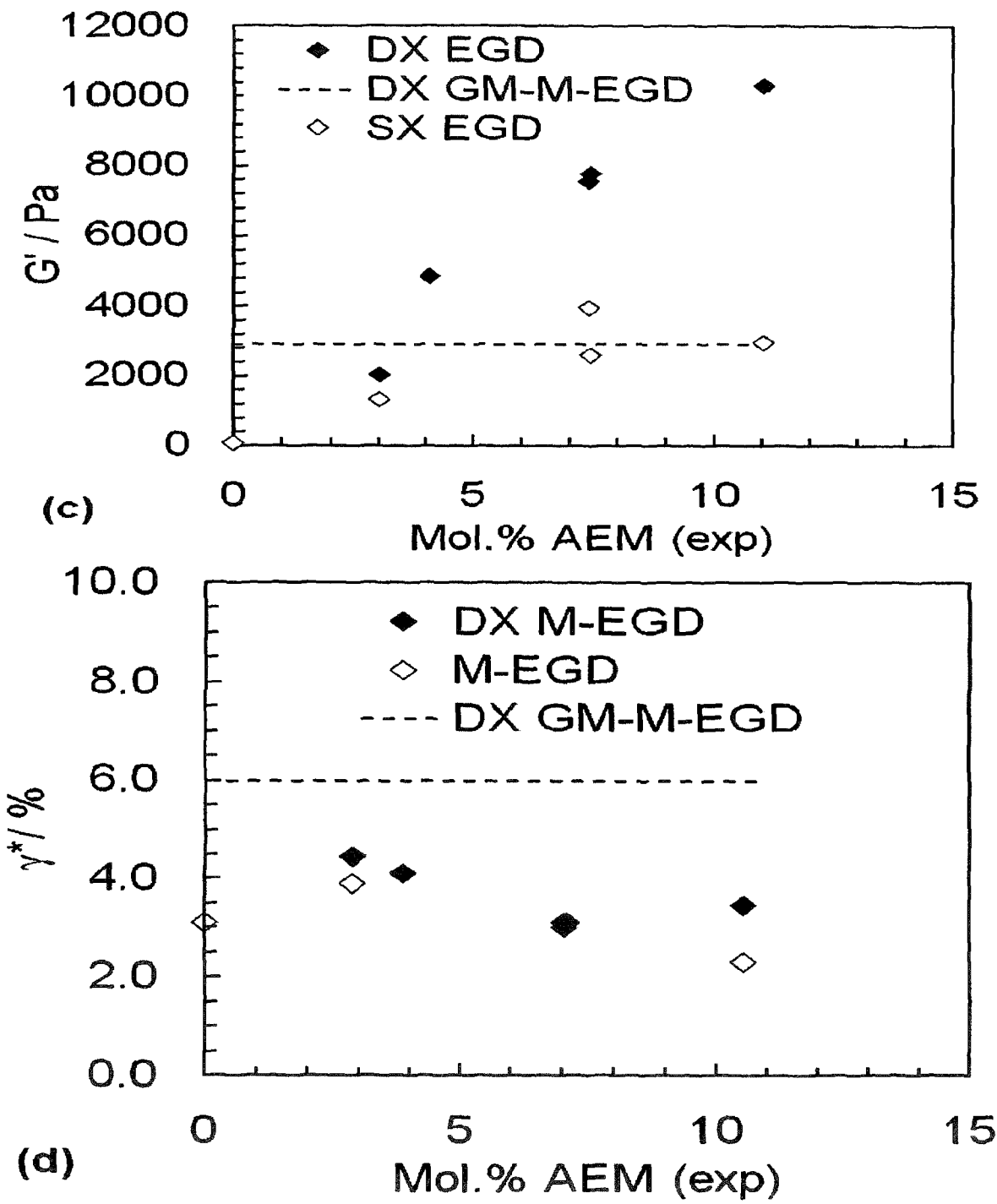

FIG. 14B-1 shows strain amplitude sweeps ((a) and (b)) and frequency sweeps ((c) and (d)) for concentrated SX AEM-M-EGD microgel dispersions. The legends give the [AEM]/[MAA] ratios used for preparation of the AEM functionalised microgels. Data for E-BDD microgel are also shown. The measurements were made using 1 Hz (strain amplitude) or 1% strain (frequency sweep) using $\phi_p$=0.1 and pH=8.4.

From FIG. 14B-1 it can be seen that there is a major difference between the dynamic rheological behaviour for the concentrated M-EGD and E-BDD microgels. The former is a weak gel; whereas, the latter has a much higher elasticity and yield strain. Following related work (Chougnet, A.; Audibert, A.; Moan, M. *Rheol. Acta* 2007, 46, 793), the yield strain (γ*) is defined here as the strain at which G' has fallen to 95% of its value at 1% strain. The variation of G' and γ* are shown in FIG. 14B-2.

FIG. 14B-2 shows variation of (a) G' and (b) yield strain with [AEM]/[MAA] ratio for concentrated singly cross-linked microgel dispersions. Data were obtained using $\phi_p$=0.1 and pH=8.4. The data points for E-BDD was obtained using pH=7.8. The data for (a) were obtained at 1% strain and 1 Hz.

Based on equation (3) it is suggested that the major increase of G' for E-BDD compared to M-EGD (factor of 50) is due to the greater overlap and inter-penetration of the microgel. This probably also accounts for the much greater value for γ* (factor 2.5 higher).

It can also be seen from FIG. 14B-2 that the G' increases substantially with [AEM]/[MAA] ratio used for preparation. The maximum increase is also a factor of about 50. However, in this case γ* has not increased, but is about the same. This suggests that there is no improvement in overlap for the gel as a whole. The PCS data (FIG. 2) indicate that no additional swelling occurred as a result of functionalisation as expected since there are less MAA groups present in the functionalised microgel. Therefore, it can be concluded that the increases in G' observed for these physical gels upon functionalisation is due to an increased tendency of the particle aggregates to form physical contacts through hydrophobic association. Indeed, it was noted that the functionalised microgel dispersions had a tendency to phase separate if left for extended periods (month) indicating that aggregation occurred. These data then show that increasing the hydrophobicity of the microgel particles adds a hydrophobic component to the particle-particle contacts that occur during double crosslinking. This component dominates the gel behaviour for the AEM functionalised M-EGD microgels. It can be suggested that these concentrated dispersions consist of swollen, aggregates with a hydrophobic periphery which is rich in AEM groups.

Dynamic rheology measurements were made using the DX microgels as obtained from Example 2.

FIG. 14B-3 shows strain amplitude sweeps ((a) and (b)) and frequency sweeps ((c) and (d)) for DX AEM-M-EGD microgels. The legends give the [AEM]/[MAA] ratios used for preparation. The measurements were made using 1 Hz (strain amplitude) or 1% strain (frequency sweep) using $\phi_p$=0.1 and pH=8.4. Data for a doubly crosslinked GM functionalised microgel (DX GM-M-EGD) are also shown for comparison.

The data shown in FIG. 14B-3 reveal that the DX microgels had consistently higher G' values than the SX microgels (Compare to FIG. 14B-1). Both the SX and DX microgel systems tended to undergo a major decrease in G' and increase in tan δ when the strain exceeded about 10%. The data also permit comparison between our two functionalisation methods. The maximum G' value achieved for the DX AEM-M-EGD microgels ([AEM/[MAA]=0.5) is approximately a factor of 4.5 that achieved using the GMA-functionalisation method. These data suggest that the AEM functionalisation method provides DX microgels with higher elasticity than those achieved using GM functionalisation[1].

The frequency dependent G' and tan δ data are shown in FIGS. 9(c) and (d). The gradients are very low (especially for tan δ vs. frequency) indicating gel-like behaviour as identified by Winter and Chambon criteria[20-21]. The range of values are the same as for the physical gels containing AEM functionalised particles (FIGS. 5(c) and (d)) and confirms that the DX microgels preserve the low dissipative components of their rheological properties.

(ii) Variation of (a) G' and Tan δ as Well as (b) γ* with Preparation Conditions for Doubly Cross-Linked Microgels of Example 5

FIG. 14B-4 shows the effect of preparation conditions on the mechanical properties of DX microgels. G' and tan δ values for DX and SX microgels as a function of [AEM]/[MAA] ratio used to prepare the functionalised microgels are shown in (a) and (b). G' and γ* values are plotted as a function of mol. % AEM present within the functionalised microgels in (c) and (d). Values for the DX GM-M-EGD microgel are shown as the horizontal lines. The data were measured at 1% strain. The data were obtained using $\phi_p$=0.10 and pH=8.4.

The frequency dependent G' and tan δ data are shown in FIGS. 9(c) and (d). The gradients are very low (especially for tan δ vs. frequency) indicating gel-like behaviour as identified by Winter and Chambon criteria (Winter, H. H. *Polym. Eng. Sci.* 1987, 27, 1698; and Winter, H. H.; Chambon, F. *J. Rheol.* 1986, 30, 367). The range of values are the same as for the physical gels containing AEM functionalised particles (FIG. 14B-1(c) and (d)) and confirms that the DX microgels preserve the low dissipative components of their rheological properties.

Data taken from FIG. 14B-3 at a frequency and strain of 1 Hz and 1%, respectively, are shown in FIG. 14B-4. The contrast between DX and SX microgels is very clear at higher degrees of functionalisation. Comparison of these data for the DX and respective SX microgels (FIGS. 14B-4(a) and (c)) shows clearly that crosslinking provided an increased G' in addition to the hydrophobic contribution discussed above. The increased G' values can be attributed to additional covalent crosslinking from the AEM groups. Moreover, G' for DX microgels appears to be proportional to the amount of AEM incorporated when the mol. % AEM (exp) exceeds 3%. The G' values for the DX microgels of up to $10^4$ Pa are respectable values given that $\phi_p$ is only 0.10. The use of higher $\phi_p$ values would certainly enable much higher G' values to be achieved[1].

An interesting point concerns the ability of these DX microgels to withstand strain. Values for γ* are shown in FIG. 14B-4(d). These values are between 2.5 and 4.5% and are not significantly different to those for the respective SX AEM-M-EGD microgels. The value of γ* for the DX GM-M-EGD microgel was 6.0%. This was a factor of 2 higher than the values of γ* for the parent microgel (M-EGD) and also significantly greater than those for the DX AEM-M-EGD microgels. Although the AEM functionalisation method has resulted in a major increase in G' for the M-EGD DX microgels, these gels are inherently more brittle. Presumably, this is because the molar mass of the elastically effective chains at the periphery is low. This could indicate reduced inter-penetration of the peripheries of the aggregates in the physical gels.

Conclusions

In this study we investigated a new method, involving EDC coupling, for preparing vinyl functionalised microgels in order to increase the modulus of DX microgels. The titration data indicate that the functionalisation proceeds from the exterior of the microgels inwards. Partial aggregation occurred during the functionalisation process. This appears to play a role in limiting the maximum degree of functionalisation that can be achieved to about 12 mol. % in total, i.e., about $\frac{1}{3}^{rd}$ of the RCOOH groups. Physical gels (SX microgels) formed in concentrated dispersions that had a hydrophobic contribution to their elasticity. Double cross-linking of the partially aggregated dispersions gave gels with high elasticity and this is consistent with a relatively high degree of functionalisaton. The modulus of the DX microgels appears to be tunable using the mol. % of AEM incorporated. The results support the suggestion that EDC coupling would increase functionalisation and elastic modulus. The mechanical properties of these DX microgels can be controlled by their composition. In the previous work (Liu, R.; Milani, A. H.; Freemont, T. J.; Saunders, B. R. *Manuscript submitted to Soft Matter* 2011) the maximum G' achieved was 2,800 Pa. An improvement of elastic modulus by about a factor of 4.5 compared to the previous method was found for the DX AEM50-M-EGD microgel. However, these DX microgels are more brittle, with a yield strain that decreased by about a factor of 2. This is most likely because of reduced overlap between the aggregates due to the more hydrophobic microgel particle peripheries. Future work will involve washing the M-EGD microgels with ethyl acetate prior to functionalisation in order to increase the swelling and overlap during double crosslinking. We expect the technique to apply well to the AEM-E-BDD microgels and this is currently under being studied. A successful result will show that the technique is widely applicable to RCOOH containing microgels.

Example 6—Cross-Linking of the Vinyl-Grafted Microgel Particles by UV Irradiation 2.5 ml of poly(MMA/MAA/EGDMA)-GMA microgel (16 wt. %) was added to a mixture of 0.2 ml of Irgacure 2959 (10 wt. % in ethanol), 0.5 ml of aqueous 2 M NaOH and 0.8 ml of DI water by stirring. The final pH was maintained between 7.5 and 8.5. The dispersion was exposed to UV light for 2.5 hours.

Characterisation (i) Variation of (a) G' and Tan δ as Well as (b) γ* with Microgel Particle Volume Fraction for Doubly Cross-Linked 2BG Microgel.

The results are shown in FIG. 16. To convert to wt % multiply $\phi_p$ by 100. The double cross-linking was performed at using UV irradiation using Microgel 2BG using the method described in Example 6.

Example 7—Cross-Linking of Vinyl-Grafted Microgel Particles by Formation of an Interpenetrating Polymer Network Three Methods were Used:
Method A:
The microgel added first. Typically, the system contained 10 wt. % microgel and 10 wt. % PEGDMA550, a mixture of 0.2 ml of ammonium persulfate solution (10 wt. % in water), 0.5 ml of aqueous 2 M NaOH was added to a mixture of 2.5 ml of poly(MMA/MAA/EGDMA)-GMA microgel (16 wt. %), 0.36 ml of PEGDMA550 and 0.44 ml of DI water by stirring. The final weak gel like mixture was held in a water bath and allowed to react at the desired temperature.

Method B:
Cross-linker added first. In this case 2.5 ml of poly(MMA/MAA/EGDMA)-GMA microgel (16 wt. %) was added to a pre-prepared mixture of 0.2 ml of ammonium persulfate solution (10 wt. % in water), 0.5 ml of aqueous 2 M NaOH, 0.36 ml of PEGDMA550 and 0.34 ml of DI water by stirring. Before the microgel was added the mixture of all of the other materials were mixed for half a minute. The final liquid like mixture was held in a water bath and allowed to react at the desired temperature.

When required, accelerator, TEMED, was added to the mixture of ammonium persulfate and NaOH solution before microgel or PEGDMA was added within Method 6A and Method 6B. The addition of TEMED decreased the cross-linking time and enabled a temperature of 37° C. to be used.

Figure 17:
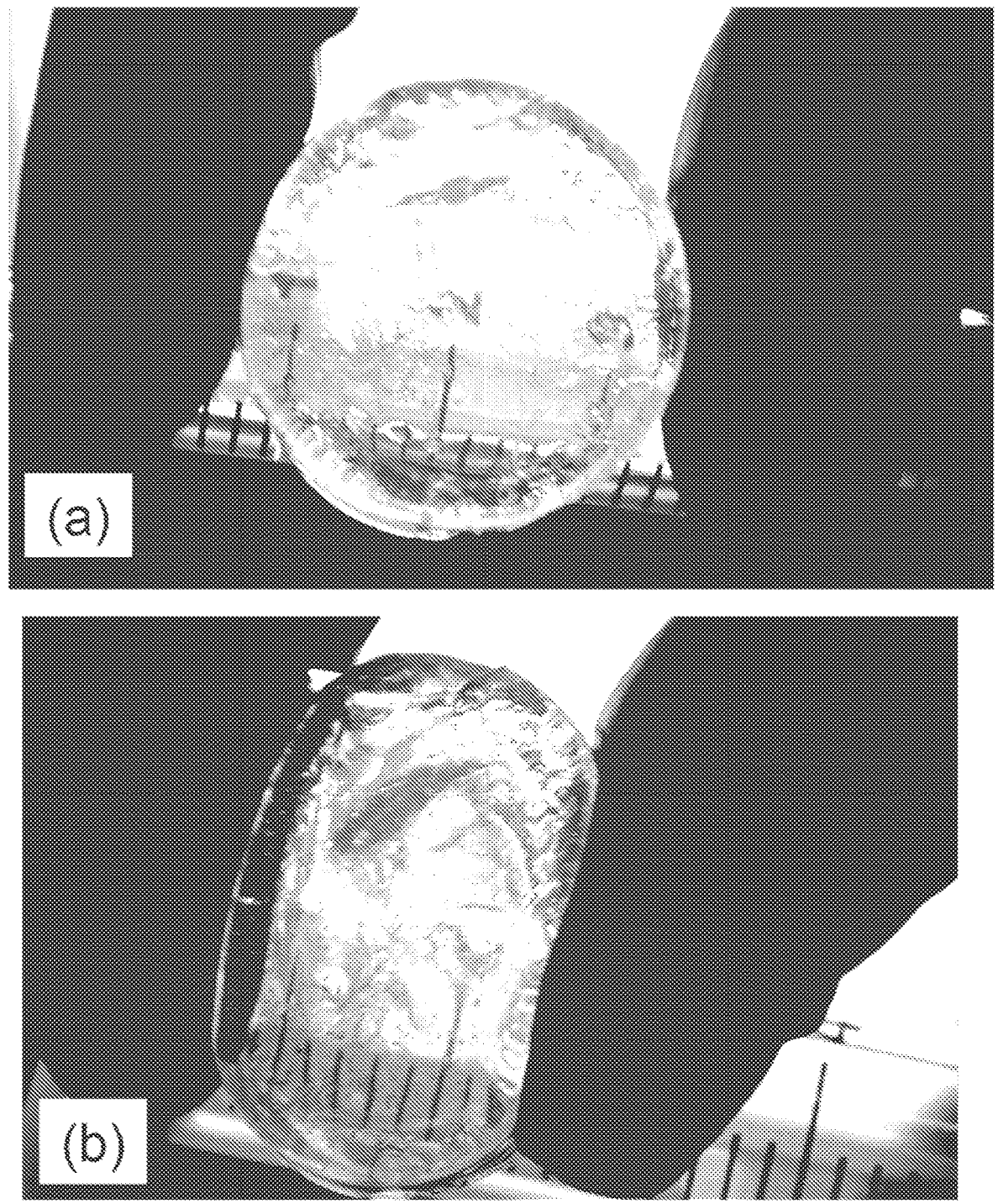

Method C: UV-Irradiation
In the UV-light initiation case 2.5 ml of poly(MMA/MAA/EGDMA)-GMA microgel (16 wt. %) was added to a mixture of 0.2 ml of Irgacure 2959 solution (10 wt. % in ethanol), 0.5 ml of aqueous 2 M NaOH, 0.36 ml of PEGDMA550 and 0.44 ml of DI water by stirring. Before the microgel was added the mixture of all of the other materials were mixed for half a minute. The final weak gel like mixture was placed under UV light for 3 hours Characterisation
A cross-linked microgel composition of the invention formed by the method of Example 7, Method B (and in the presence of TEMED) is shown in FIG. 17. The material was prepared using 10 wt % PEGDMA550 and 10 wt. % microgel 2BG. The gel was prepared at 37° C. The scale bar is in centimeters.

Variation of (a) G' and Tan δ as Well as (b) γ* with Wt. % of PEGDMA550 Used to Prepare Doubly Cross-Linked Microgels.

Figure 18:
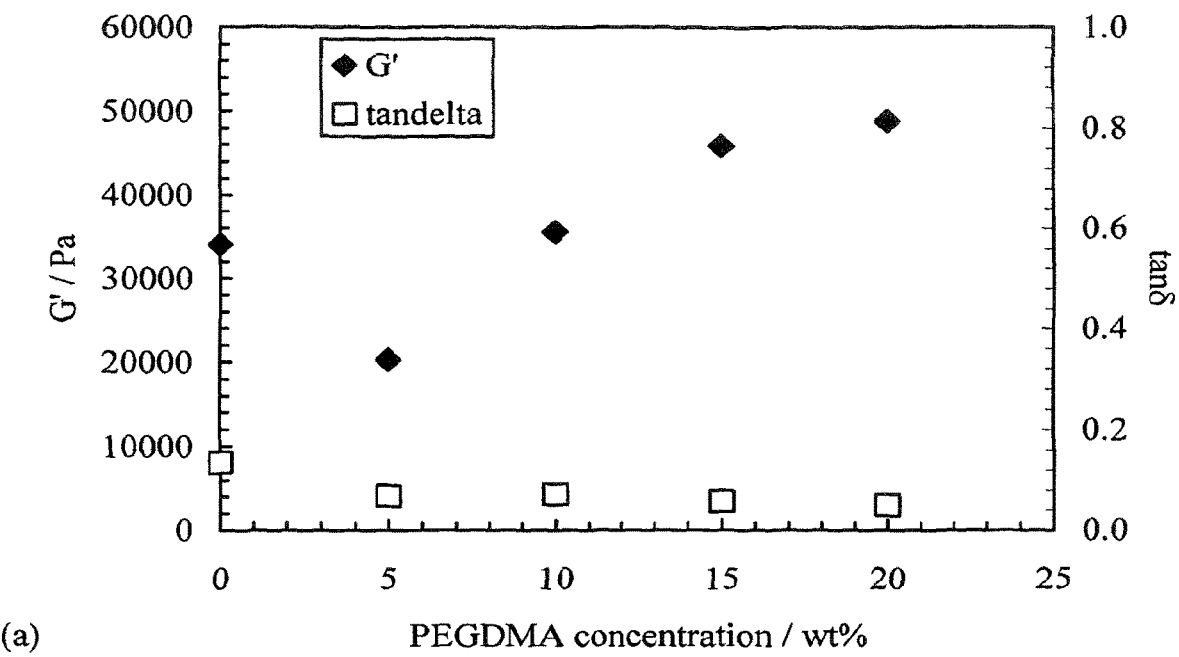
Figure 18:
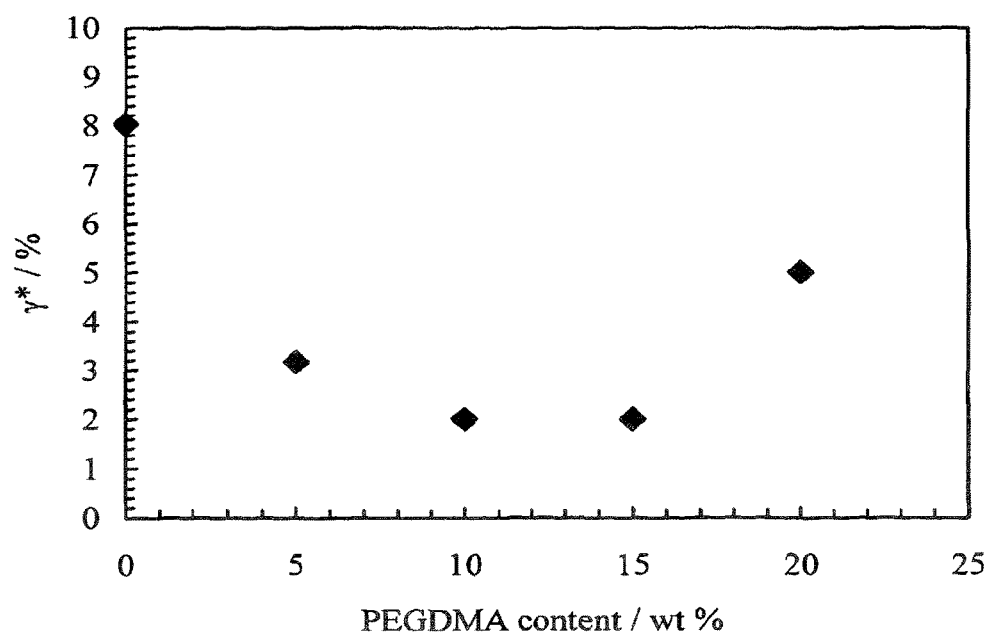

The total concentration of Microgel 2BG and PEGDMA550 was 20 wt. %. It should be noted that the PEGDMA550 only system did not form a space-filling gel; whereas, the other systems did. The doubly cross-linked microgels were prepared using UV cross-linking using the process described in Example 4, Method C. The results are shown in FIG. 18.

The invention claimed is:
1. A method of treating damaged or degenerated soft tissue in a subject, the method comprising administering by injection, to the damaged or degenerated soft tissue or into a joint containing the damaged or degenerated soft tissue, a plurality of pH-responsive microgel particles and one or more cross-linking reactants, at least one of which is a free-radical initiator;

wherein each pH-responsive microgel particle comprises a plurality of vinyl-containing moieties grafted onto the surface of the microgel particles, wherein each vinyl containing moiety is a group of the formula L-B, wherein L is a bond or linking group and B is a group comprising a vinyl functional group, the pH-responsive microgel particles having a capacity to undergo a pH-triggered transition from a collapsed configuration into a swollen configuration in response to a pH change from a pH between 5.0 to 6.6 to a pH between 6.6 and 8; and wherein the pH-responsive microgel particles are administered at a pH between 6.6 and 8 to the damaged or degenerated soft tissue or into the joint containing the damaged or degenerated soft tissue, wherein in situ adjacent microgel particles are covalently bound together via free radical reactions between vinyl groups of the vinyl-containing moieties grafted onto the surface of the microgel particles to form doubly cross-linked microgel particles.

2. The method of claim 1, wherein the microgel particles comprise:

a co-polymerised polymer particle defined by formula I:

$$Poly(HM\text{-}co\text{-}P\text{-}co\text{-}X) \qquad (I)$$

wherein:

P is a pH-responsive co-monomer;

X is a functional cross-linking co-monomer; and

HM is a hydrophobic co-monomer; and a plurality of vinyl-containing moieties grafted onto the surface of the microgel particles, wherein each vinyl containing moiety is a group of the formula L-B, wherein L is a bond or linking group, and B is a group comprising a vinyl functional group.

3. The method of claim 2, wherein the microgel particles comprise poly (methylmethacrylate/methacrylic acid/ethyleneglycol dimethacrylate).

4. The method of claim 1, wherein the vinyl-containing moieties of formula -L-B are grafted to the surface of the microgel particles via coupling glycidyl methacrylate to carboxylic acid groups on the microgel surface.

5. The method of claim 1, wherein the free-radical initiator has the general formula $[M]S_2O_8^{2-}$, wherein M is a cation.

6. The method of claim 5, wherein the one or more cross-linking reactants further comprises an accelerator.

7. The method of claim 6, wherein the accelerator is ascorbic acid.

8. The method of claim 1, wherein a physiologically acceptable buffer solution is co-administered with the pH-responsive microgel particles.

9. The method of claim 8, wherein the physiologically acceptable buffer solution and microgel particles are mixed together to swell just prior to administration.

10. The method of claim 1, wherein the damaged or degenerated soft tissue or the joint containing the damaged or degenerated soft tissue is selected from the group consisting of intervertebral discs, nucleus pulposus (NP) of intervertebral discs, articular joints, articular elbow joints, articular knee joints, articular hip joints, articular wrist joints, articular shoulder joints, articular ankle joints, joints present in a finger, and joints present in a thumb.

11. The method of claim 1, wherein the method is performed to repair and/or replace damaged or degenerated soft tissue.

12. The method of claim 1, wherein the pH-responsive microgel particles are present at a concentration of 10-20 wt % when administered to the damaged or degenerated soft tissue or the joint containing the damaged or degenerated soft tissue.

13. The method of claim 1, wherein the pH-responsive microgel particles are in a swollen configuration at the physiological pH of the damaged or degenerated soft tissue or joint containing the damaged or degenerated soft tissue.

14. The method of claim 1 wherein the free-radical initiator is ammonium persulfate.

15. A method of treating a damaged or degenerated nucleus pulposus in a subject, the method comprising administering by injection, to the damaged or degenerated nucleus pulposus, a plurality of pH-responsive microgel particles and one or more cross-linking reactants, at least one of which is a free-radical initiator;

wherein each pH-responsive microgel particle comprises a plurality of vinyl-containing moieties grafted onto the surface of the microgel particles, wherein each vinyl containing moiety is a group of the formula -L-B, wherein L is a bond or linking group and B is a group comprising a vinyl functional group; and the pH-responsive microgel particles are further characterized by a capacity to undergo a pH-triggered transition from the collapsed configuration into the swollen configuration in response to a pH change from a pH between 5.0 to 6.6 to a pH between 6.6 and 8;

wherein the pH-responsive microgel particles are administered at a pH between 6.6 and 8 to the damaged or degenerated nucleus pulposus wherein in situ adjacent microgel particles are covalently bound together via free radical reactions between vinyl groups of the vinyl-containing moieties grafted onto the surface of the microgel particles to form doubly cross-linked microgel particles.

16. The method of claim 15, wherein a physiologically acceptable buffer solution is co-administered with the pH-responsive microgel particles, and the physiologically acceptable buffer solution and microgel particles are mixed together to swell just prior to administration.

17. The method of claim 15, wherein the microgel particles comprise poly (methylmethacrylate/methacrylic acid/ethyleneglycol dimethacrylate).

18. The method of claim 15, wherein the free-radical initiator has the general formula $[M]S_2O_8^{2-}$, wherein M is a cation selected from the group consisting of $K^+$, $Na^+$ and $NH_4^+$.

19. The method of claim 15, wherein the one or more cross-linking reactants further comprise ascorbic acid.

20. A method of treating a damaged or degenerated nucleus pulposus in a subject, the method comprising administering by injection, to the damaged or degenerated nucleus pulposus, a plurality of pH-responsive microgel particles, ascorbic acid, and a free-radical initiator having the general formula $[M]S_2O_8^{2-}$, wherein M is a cation selected from the group consisting of $K^+$, $Na^+$ and $NH_4^+$;

wherein each pH-responsive microgel particle comprises poly (methylmethacrylate/methacrylic acid/ethyleneglycol dimethacrylate) and a plurality of vinyl-containing moieties grafted onto the surface of the microgel particles, wherein each vinyl containing moiety is a group of the formula -L-B, wherein L is a bond or linking group and B is a group comprising a vinyl functional group; and the pH-responsive microgel particles are further characterized by a capacity to undergo a pH-triggered transition from the collapsed configuration into the swollen configuration in response to a pH change from a pH between 5.0 to 6.6 to a pH between 6.6 and 8;

wherein the pH-responsive microgel particles are mixed together with a physiologically acceptable buffer solution just prior to their co-administration, at a pH between 6.6 and 8, to the damaged or degenerated nucleus pulposus wherein in situ adjacent microgel particles are covalently bound together via free radical reactions between vinyl groups of the vinyl-containing moieties grafted onto the surface of the microgel particles to form doubly cross-linked microgel particles.

* * * * *